United States Patent
Erdman

(10) Patent No.: US 11,007,235 B2
(45) Date of Patent: May 18, 2021

(54) CANINE MICROBE PREPARATIONS FOR INCREASING OXYTOCIN

(71) Applicant: Susan E. Erdman, Hopkinton, MA (US)

(72) Inventor: Susan E. Erdman, Hopkinton, MA (US)

( * ) Notice: Subject to any disclaimer, the term of this patent is extended or adjusted under 35 U.S.C. 154(b) by 121 days.

(21) Appl. No.: 15/630,787

(22) Filed: Jun. 22, 2017

(65) Prior Publication Data
US 2017/0368112 A1 Dec. 28, 2017

Related U.S. Application Data

(60) Provisional application No. 62/353,954, filed on Jun. 23, 2016.

(51) Int. Cl.
- A01N 63/00 (2020.01)
- A61K 35/747 (2015.01)
- C07K 1/14 (2006.01)

(52) U.S. Cl.
CPC .............. *A61K 35/747* (2013.01); *C07K 1/14* (2013.01)

(58) Field of Classification Search
USPC ....................................................... 424/93.45
See application file for complete search history.

(56) References Cited

U.S. PATENT DOCUMENTS

| | | |
|---|---|---|
| 2015/0196608 A1 | 7/2015 | Chen et al. |
| 2015/0250835 A1 | 9/2015 | Huang et al. |

OTHER PUBLICATIONS

Varian et al. Journal of Probiotic and Health vol. 4, issue 3, Jun. 10, 2016 (Year: 2016).*
Erdman et al. Benef Microbes. Jun. 1, 2014; 5(2), 109-119. (Year: 2014).*
Poutahidis et al. ( PLoS One, vol. 8, issue 10, pp. 1-17, Oct. 2013. (Year: 2013).*
Levkovich T, Poutahidis T, Smillie C, Varian BJ, Ibrahim YM, et al. (2013) Probiotic Bacteria Induce a 'Glow of Health'. PLoS One 8 (1) (Year: 2013).*
Adams, "The Probiotic Paradox: Live and Dead Cells are Biological Response Modifiers," *Nutrition Research Reviews*, 23:37-46, (2010).
Dommels, et al., "Survival of Lactobacillus reuteri DSM 17938 and Lactobacillus rhamnosus GG in the Human Gastrointestinal Tract with Daily Consumption of a Low-Fat Probiotic Spread$^V$," *Applied and Environmental Microbiology*, 75(19):6198-6204, (Oct. 2009).
Erdman, et al., "Probiotic 'Glow of Health': It's More Than Skin Deep," *Benef. Microbes*, 5(2):109-119, (Jun. 1, 2014).
Fak, et al., "Lactobacillus reuteri Prevents Diet-Induced Obesity, but not Atherosclerosis, in a Strain Dependent Fashion in Apoie -/- Mice," *PLoS One*, 7(10):1-8, (Oct. 2012).
Hsieh, et al., "Heat-Killed and Live Lactobacillus reuteri GMNL-263 Exhibit Similar Effects on Improving Metabolic Functions in High-Fat Diet-Induced Obese Rats," *Food Funct.*, 7:2374-2388, (2016).
Jankowski, et al., "Oxytocin and Cardioprotection in Diabetes and Obesity," *BMC Endocrine Disorders*, 16(34):1-9, (2016).
Lakritz, et al., "Beneficial Bacteria Stimulate Host Immune Cells to Counteract Dietary and Genetic Predisposition to Mammary Cancer in Mice," *International Journal of Cancer*, 135:529-540, (2014).
Levkovich, et al., "Probiotic Bacteria Induce a 'Glow of Health,'" *PLoS One*, 8(1):1-11, (Jan. 2013).
Naito, et al., "Beneficial Effect of Oral Administration of Lactobacillus casei Strain Shirota on Insulin Resistance in Diet-Induced Obesity Mice," *Journal of Applied Microbiology*, 110:650-657, (2011).
Project No. 5P30ES002109-37, "MIT Center for Environmental Health Sciences," Project Start Date, Apr. 1, 1997, 4 pages.
Project No. 1R01CA108854-01A1, "Role of IL10 and TGFB1 in Colon Cancer," Project Start Date, Aug. 1, 2005, 2 pages.
Project No. 4U0CA164337-05, "GI Tract Dysbiosis and Breast Cancer," Project Start Date, Sep. 26, 2012, 2 pages.
Poutahidis, et al., "Dietary Microbes Modulate Transgenerational Cancer Risk," *Cancer Research*, 75(7):1197-1204, (Apr. 1, 2015).
Poutahidis, et al., "Microbial Reprogramming Inhibits Western Diet-Associated Obesity," *PLoS One*, 8(7):1-11, (Jul. 2013).
Poutahidis, et al., "Probiotic Microbes Sustain Youthful Serum Testosterone Levels and Testicular Size in Aging Mice," *PLoS One*, 9(1):1-12, (Jan. 2014).
Poutahidis, et al., "Microbial Symbionts Accelerate Wound Healing via the Neuropeptide Hormone Oxytocin," *PLoS One*, 8(10):1-17, (Oct. 2013).
Sanchez, et al., "Effect of Lactobacillus Rhamnosus CGMCC1.3724 Supplementation on Weight Loss and Maintenance in Obese Men and Women," *British of Nutrition*, 111:1507-1519, (2014).
Saulnier, et al., "Exploring Metabolic Pathway Reconstruction and Genome-Wide Expression Profiling in Lactobacillus reuteri to Define Functional Probiotic Features," *PLoS One*, 6(4):1-14, (Apr. 2011).
Ting, et al., "Supplementary Heat-Killed Lactobacillus reuteri GMNL-263 Ameliorates Hyperlipidaemic and Cardiac Apoptosis in High-Fat Diet-Fed Hamsters to Maintain Cardiovascular Function," *British Journal of Nutrition*, 114:706-712, (2015).

(Continued)

*Primary Examiner* — Jana A Hines
*Assistant Examiner* — Khatol S Shahnan Shah
(74) *Attorney, Agent, or Firm* — Morse, Barnes-Brown & Pendleton, P.C.; Sean D. Detweiler, Esq.; Stanley F. Chalvire, Esq.

(57) ABSTRACT

The inventions disclosed herein relate to the findings that *L. reuteri* bacteria isolated from dog saliva is capable of modulating a subject's body weight. In certain aspects, the inventions disclosed herein relate to the findings that *L. reuteri* species isolated from dog saliva elevates a subject's oxytocin levels in blood plasma and surprisingly, the killed (lysed) bacteria was sufficient to achieve the observed effects.

15 Claims, 16 Drawing Sheets
Specification includes a Sequence Listing.

(56) References Cited

OTHER PUBLICATIONS

Ting, et al., "Heat Killed Lactobacillus reuteri GMNL-263 Reduces Fibrosis Effects on the Liver and Heart in High Fat Diet-Hamsters via TGF-β Suppression," *Int. J. Mol. Sci.*, 16:25881-25896, (2015).
Varian, et al., "Beneficial Bacteria Stimulate Youthful Thyroid Gland Activity," *Journal of Obesity & Weight Loss Therapy*, 4(2):1-8, (2014).
Varian, et al., "Beneficial Dog Bacteria Up-Regulate Oxytocin and Lower Risk of Obesity," *Journal of Probiotics & Health*, 4(3):1-9, (2016).
Varian, et al., "Microbial Lysate Upregulates Host Oxytocin," *Brain Behav. Immun.*, 61:36-49, (Mar. 2017).
Varian, et al., "Beneficial Bacterial Inhibit Cachexia," *Oncotarget*, 7(11):11803-11816, (Feb. 25, 2016).
International Search Report from PCT/US2017/038841, dated Oct. 2, 2017.

\* cited by examiner

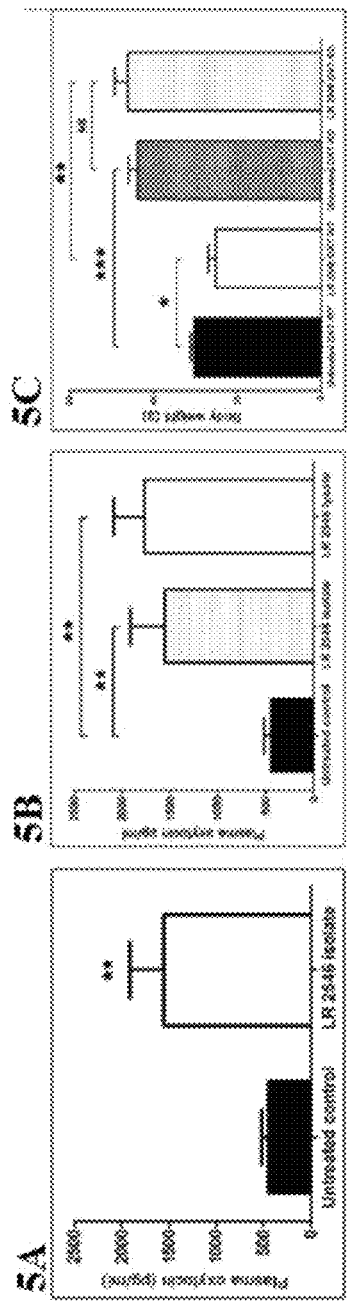
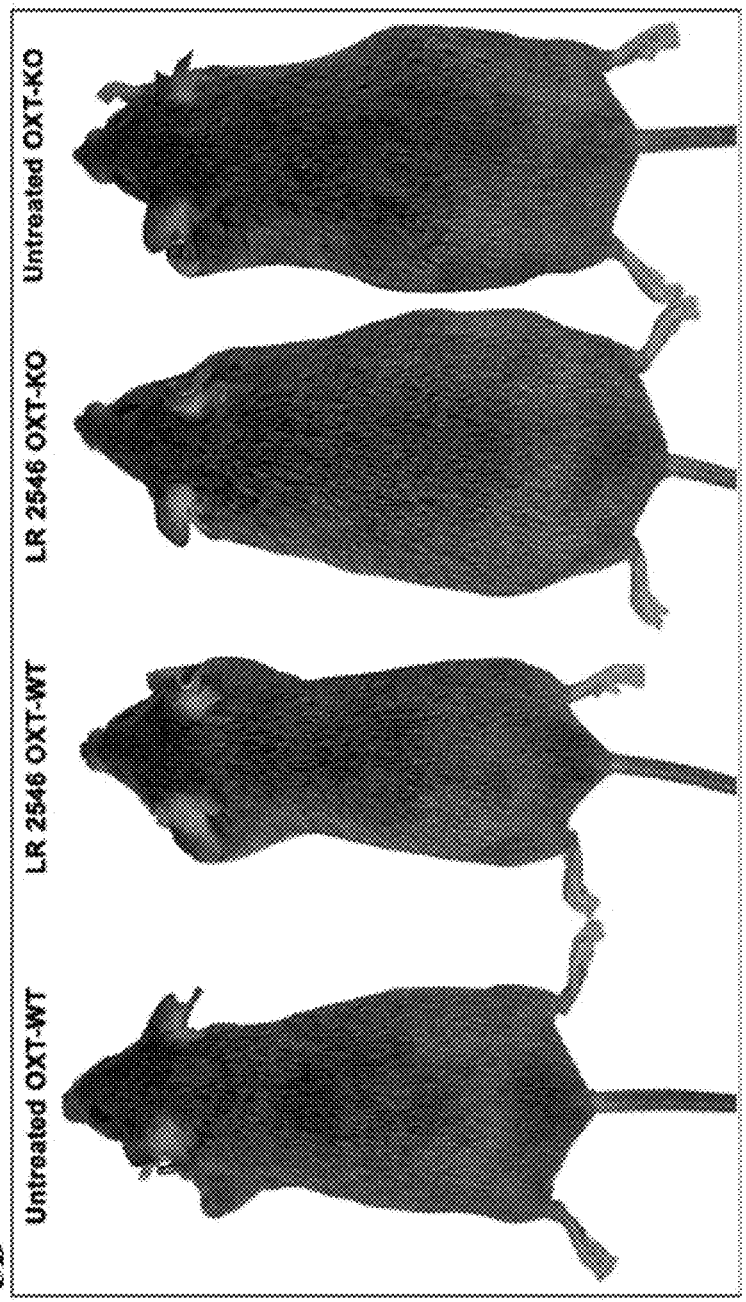
FIGS. 5A-5D

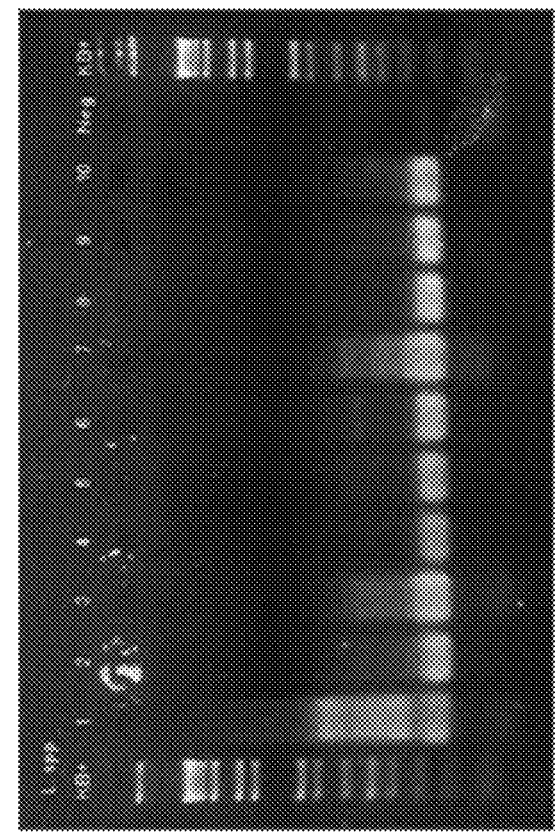
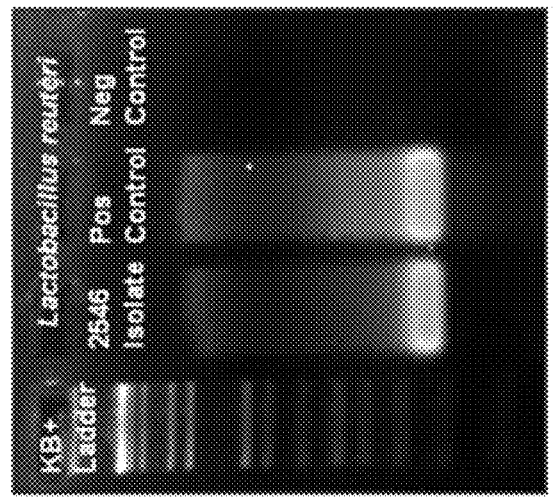
| Positive Biochemical Tests in the API 50 CHL V5.2 | | |
|---|---|---|
| LARA | GLU | LAC | RAF |
| RIB | MDG | MEL |
| GAL | MAL | SAC |
| Significant taxa | % ID |
|---|---|
| Lactobacillus fermentum | 85.2 |
| Lactobacillus buchneri | 13.5 |
| Lactobacillus brevis 2 | 1.2 |
*FIGS. 6A-6D*

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: LactoF primer

<400> SEQUENCE: 1
tggaaacagr tgctaatacc g                                              21

<210> SEQ ID NO 2
<211> LENGTH: 20
<212> TYPE: DNA
<213> ORGANISM: Artificial
<220> FEATURE:
<223> OTHER INFORMATION: LactoR primer

<400> SEQUENCE: 2
gtccattgtg gaagattccc                                                20

<210> SEQ ID NO 3
<211> LENGTH: 21
<212> TYPE: DNA
<213> ORGANISM: Artificial
<220> FEATURE:
<223> OTHER INFORMATION: L-reu-1 primer

<400> SEQUENCE: 3
cagacaatct ttgattgttt a                                              21

<210> SEQ ID NO 4
<211> LENGTH: 21
<212> TYPE: DNA
<213> ORGANISM: Artificial
<220> FEATURE:
<223> OTHER INFORMATION: L-REU-4 primer

<400> SEQUENCE: 4
gtctgttggt ttgggctctt c                                              21
```

CANINE MICROBE PREPARATIONS FOR INCREASING OXYTOCIN

RELATED APPLICATIONS

This application claims the benefit of U.S. Provisional Application No. 62/353,954, filed Jun. 23, 2016. The entire teachings of the above application are incorporated herein by reference.

GOVERNMENT SUPPORT

This invention was made with government support under grants P30-ES002109, R01-CA108854 and U01-CA164337 awarded by the National Institutes of Health. The government has certain rights in the invention.

BACKGROUND OF THE INVENTION

Pets are often considered to be part of the family. Cohabitating with dogs, in particular, has many benefits to humans associated with physical, psychological and social wellbeing [1]. One benefit of human co-habitation with dogs is a more slender physique [2]. This observation is important in the context of the growing obesity epidemic, which has impacted over 78 million adults and 12.5 million children and adolescents in the U.S. in 2009-2010 [3]. In the face of this growing obesity epidemic [3], there is relative inefficiency of existing weight loss strategies. Although a clear relationship between dog ownership and lower risk of obesity exists, study designs have been unable to show a specific link with the hypothesis of increased activity levels due to humans taking more walks or playing with pet dogs [4]. Alternatively, environmental exposures involving pet dogs have been proposed. An understanding of mechanisms through which environmental factors influence obesity is important to develop future interventions [5].

One possible link between dogs and humans is exchange of microbiota. The close cohabitation of dogs and humans may facilitate the transfer of various infectious agents between these species. Lower prevalence of allergic diseases among those living on farms or with pets during childhood support this concept [6-13]. Indeed, this idea coined the "hygiene hypothesis" theory is based on associations between the decrease in beneficial microbial burdens and the increase in the development of allergies, autoimmune disease and generalized immune dysfunction in modernized societies. A relevant study showed that household dogs may disseminate *Lactobacillus johnsonii* in household dust that lower risk of asthma and other inflammatory disorders in cohabitating humans [14].

The neuropeptide hormone oxytocin is pivotal in the canine-human bond, with studies showing that humans experience higher levels of oxytocin during interactions with pet dogs [15,16]. Importantly, oxytocin has also been convincingly linked with protection from obesity [17-23]. While the nonapeptide oxytocin is historically recognized for its role in parturition [24] and lactation [25] it has gained more recent attention for its apparent effects on prosocial behavior [26,27] and therapeutic potential in the treatment of autism spectrum disorder (ASD) [26,27], schizophrenia [26,28] and obesity [17-23]. A large number of ongoing investigations in humans list oxytocin as the focus in studies on caloric intake, gastric emptying, or obesity, as displayed in the ClinicalTrials.gov registry, National Institutes of Health. Specifically, studies show oxytocin has roles in reducing food intake and body weight in diet-induced obesity [17,19,21-23] in genetically obese rodent models [18,20,21], highlighting potential downstream central nervous system and peripheral mechanisms. It was also shown that intranasal administration of oxytocin in humans lowers caloric intake and has beneficial metabolic effects, resulting in a shift from carbohydrate to fat utilization and improved insulin sensitivity [29]. Recognizing that oxytocin is important in the mother-infant bond, it was earlier found that ingested *L. reuteri* ATCC 6475 bacteria extracted from human milk serve to up-regulate systemic oxytocin levels in mouse models by a vagus nerve-dependent mechanism [30]. Knowing that oxytocin levels increase in humans after contact with dogs [15], the inventor tested whether exposure to *L. reuteri* bacteria extracted from dog saliva, similar to bacteria collected from human milk, may similarly modulate oxytocin levels and convey benefits of more slender physique and overall good health.

SUMMARY OF THE INVENTION

The inventions disclosed herein are based upon the finding that *Lactobacillus reuteri* (e.g., *L. reuteri* isolate 2546 from dog saliva) fed to C57BL/6 mice led to higher plasma levels of oxytocin. In addition, mice consuming canine-borne *L. reuteri* exhibited less age-associated weight gain when compared with matched untreated controls, in an oxytocin-dependent manner. Taken together, the studies disclosed herein raise the possibility that microbiota shared between species not only convey mutual survival benefits, but also serve to strengthen the human-animal bond.

In certain aspects, the inventions disclosed herein relate to methods of promoting weight loss in a subject (e.g., a human subject), wherein such methods comprise a step of administering an effective amount of a composition to the subject and thereby promoting weight loss in the subject, wherein the composition comprises *L. reuteri* bacteria (e.g., a killed or lysed *L. reuteri* bacteria).

Also disclosed are methods of treating obesity in a subject (e.g., a mammalian subject), wherein the methods comprise a step of administering an effective amount of a composition to the subject and thereby treating the obesity, wherein the composition comprises *L. reuteri* bacteria (e.g., *L. reuteri* bacteria isolated from canine saliva).

In some embodiments, the inventions disclosed herein relate to methods of increasing plasma oxytocin concentration in a subject (e.g., a human subject), wherein such methods comprise a step of administering an effective amount of a composition to the subject and thereby increasing plasma oxytocin concentration in the subject, wherein the composition comprises *L. reuteri* bacteria (e.g., a sterile *L. reuteri* bacteria).

In some aspects of any of the foregoing methods the *L. reuteri* bacteria is isolated from dog saliva. In some aspects of any of the foregoing methods the *L. reuteri* bacteria comprises *L. reuteri* isolate 2546. In some embodiments of any of the foregoing methods the *L. reuteri* bacteria comprises *L. reuteri* ATCC 6475. Alternatively, in other embodiments of any of the foregoing methods the *L. reuteri* bacteria do not comprise *L. reuteri* ATCC 6475.

In certain aspects, the *L. reuteri* bacteria are grown aerobically. For example, in certain embodiments, *L. reuteri* bacteria isolated from canine saliva may be cultivated in classical media, individual colonies selected and grown aerobically on a plate (e.g., a sheep blood agar plate).

In any of the embodiments disclosed herein, the *L. reuteri* bacteria are live. Conversely, in any of the embodiments disclosed the *L. reuteri* bacteria is killed (e.g., lysed) and/or sterile. For example, prior to administration of the composition to the subject in accordance with any of the methods disclosed herein, the *L. reuteri* bacteria contained in such composition may be lysed, killed and/or sterile (Varian, et al., Brain, Behavior, and Immunity 2017, 61: 36-49, the entire teachings of which are incorporated herein by reference).

In certain aspects, the compositions disclosed herein (e.g., a composition comprising the fractionated *L. reuteri* lysate) are administered orally. In some embodiments, the compositions disclosed herein are administered intranasally. In yet other embodiments, the compositions disclosed herein are administered parenterally. In still other embodiments, the compositions disclosed herein are administered enterally.

In some aspects of any of the foregoing, the composition further reduces the subject's abdominal fat weight. In some embodiments of any of the foregoing methods, the composition reduces the subject's subcutaneous fat. In still other embodiments of any of the foregoing, the composition reduces the subject's blood neutrophils. In some embodiments of any of the foregoing, the composition promotes lean muscle formation. In some embodiments of any of the foregoing, the compositions promote hair growth. In yet other embodiments of any of the foregoing, the compositions promote wound healing. In some embodiments of any of the foregoing, the composition increases thymus gland size. In still other embodiments of any of the foregoing, the composition reduces levels of stress biomarker hormone corticosterone.

In certain aspects, the *L. reuteri* is isolated. In some embodiments, the *L. reuteri* has been modified (e.g., relative to its native or naturally-occurring state). For example, in certain aspects, the *L. reuteri* has been killed (e.g., lysed) and/or has been rendered sterile.

In certain aspects of the inventions disclosed herein, the *L. reuteri* bacteria have been lysed, for example, lysed by sonication. In certain embodiments, the *L. reuteri* bacteria have been lysed by sonication at about 20 kHz. In certain aspects, the *L. reuteri* bacteria have been lysed by sonication at an amplitude of about 30% intensity. In certain aspects, the *L. reuteri* bacteria have been lysed by sonication in an ice water bath for about 25 minutes. For example, in some embodiments, the *L. reuteri* bacteria may be sonicated in cycles (e.g., for one minute on, followed by one minute off over about 25 minutes).

Also disclosed herein are methods of preparing a lysate of *L. reuteri*. In certain aspects, *L. reuteri* (e.g., *L. reuteri* isolated from the saliva of a dog) may be lysed by sonication at about 20 kHz, at an amplitude of about 30% intensity, in an ice water bath for about 25 minutes. In some embodiments, the *L. reuteri* bacteria may be sonicated in cycles (e.g., for one minute on, followed by one minute off over about 25 minutes).

In certain aspects, the bacterial lysates prepared in accordance with the present inventions may be further fractionated (e.g., to remove bacterial fragments). Accordingly, also disclosed herein are methods of fractionating a lysate of *L. reuteri*. For example, in certain aspects, a bacterial lysate may be subjected to centrifuge (e.g., the sonicated bacterial lysate may be subject to centrifuge for about 15 minutes at about 4,000 rpm). In some embodiments, the lysate may be further passed through a 0.2 μm filter to remove whole bacteria and large fragments contained in the lysate, thereby producing a soluble supernatant comprising the lysed *L. reuteri* bacteria.

In certain aspects, such soluble supernatant comprising the fractionated lysate of the *L. reuteri* bacteria may be administered to a subject in accordance with the methods disclosed herein, or alternatively may be included as a component of the compositions disclosed herein. For example, in certain embodiments, one or more of the compositions disclosed herein may comprise a soluble supernatant comprising the lysed *L. reuteri* bacteria, or a soluble fraction of the *L. reuteri* lysate prepared in accordance with the present inventions. The above discussed, and many other features and attendant advantages of the present inventions will become better understood by reference to the following detailed description of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2D shows that the abdominal fat of control mice had readily recognizable crown-like structure [CLS] lesions that often coalesce to form sizable pyogranulomatous lesions. By contrast, CLS were rare in *L. reuteri*-treated mice. The analysis of histomorphometrical counts of CLS in the abdominal fat of mice shows that the anti-inflammatory effect of probiotic treatment is statistically significant. Hematoxylin and Eosin. Scale bars: 100 μm. Numbers on the y-axis of bar graphs correspond to the mean±SEM of the parameters assessed; ***$p<0.0001$.

FIGS. 5A-5D illustrate that the health benefits of oral *L. reuteri* 2546 consumption depend on oxytocin. Short and long term consumption of *L. reuteri* 2546 cells, whether live (FIG. 5A) or killed (FIG. 5B), upregulate plasma oxytocin levels at statistically significant levels. FIG. 5C shows that using oxytocin-deficient mice and their wild-type controls, the present inventors found that the statistically significant effect of probiotics in reducing body weight of mice is negated in the absence of oxytocin. FIG. 5D shows whole mouse body representative images that are provided for a side-by-side comparison. Shown are oxytocin-deficient and wild-type mice that were either treated with *L. reuteri* or remained untreated. Note that the *L. reuteri* treatment correlates with a slender phenotype in wild-type, but not oxytocin-deficient mice. Numbers on the y-axis of bar graphs correspond to the mean±SEM of the parameters assessed, p<0.001, *p<0.0001.

FIGS. 6A-6D confirm the presence of *L. reuteri* in the oral cavity of dogs. By using generic PCR primers, the present inventors found evidence of *Lactobacillus* species in the oral cavity of eight [8/8] pet dogs examined (FIG. 6A). FIGS. 6B-D illustrate that based upon colony growth properties, and microscopic morphology of short rod-forming chains, a tractable Gram-positive rod isolate was confirmed to be *L. reuteri* based on the composite of gram stain/morphology, biochemical tests, and molecular tests.

FIG. 7A illustrates subgross microscopy of formalin-fixed, paraffinized wounded skin at 6 days after full thickness skin excision. The margins of wounds are outlined with yellow color. The wound area in outbred Swiss mice was significantly smaller in the *L. reuteri*-treated (n=10) mouse group compared to untreated controls (n=10). FIG. 7B illustrates that the histopathology of wounds (n=10 per group) at the same timepoint reflects the more rapid wound healing rate observed in mice consuming *L. reuteri*. The representative untreated mouse wound shown here had a clear epidermal gap (note the double-headed yellow arrow pointing to epidermal edges), edematous wound bed and retained scab. By contrast, the wound of an *L. reuteri*-treated mouse given for side-by-side comparison is completely covered with epidermis, has mature collagen in the wound bed and lacks a scab. The *L. reuteri* effect on wound re-epithelization is statistically significant. Hematoxylin and Eosin (FIG. 7B). Scale bars: 1000 μm (a) and 500 μm (b). Numbers on the y-axis of bar graphs correspond to the mean±SEM of the parameter assessed; **p<0.001.

FIG. 8A shows the wound area of human subjects consuming *L. reuteri* (BioGaia Protectis DSM 17938 chewable 100 million CFU) was significantly smaller compared to the placebo-treated (Nature Made chewable Vitamin C 60 mg) controls at three days after wounding. Biopsies were performed at Massachusetts Institute of Technology Institute for Medical Engineering and Science (IMES) Clinical Research Center (CRC). Numbers on the y-axis of the bar graph correspond to the mean±SEM of wound area; N=7 per treatment; * p=0·037; Mann-Whitney U. FIG. 8B demonstrates that to assess wound area, human skin wounds were photographed under standardized conditions. The wound margins were outlined and then the subscribed area was measured in each image. Results were recorded in mm² using a standard scale originally contained in the images. FIG. 8C provides representative images of skin wounds showing features of size and morphology from placebo (upper row) and *L. reuteri*-treated (bottom row) individuals. The wounds of subjects consuming *L. reuteri* have a smaller size than those of the placebo group, compared here at day 3 post-biopsy. Bar=1 mm.

FIG. 11A provides representative photomicrographs depicting oxytocin-ir neurons in the caudal PVN of mice treated with normal drinking water (Untreated N=9), or live *L. reuteri* (N=8), or lysed *L. reuteri* (N=10). The numerical value in the bottom right corner of top plates represents the distance (in millimeters) posterior to bregma for the rostral, intermediate and caudal PVN. FIG. 11B shows average number of oxytocin-ir cells observed in the rostral, intermediate, and caudal PVN of mice treated with normal drinking water (Untreated), live *L. reuteri*, or lysed *L. reuteri*. *p<0.05 (Tukey post hoc tests following one-way ANOVA).

FIG. 12A shows standard wound healing assay results in C57BL/6 mice, confirming that sonication-killed *L. reuteri* consumption is associated with accelerated wound closure. Comparing the size of yellow color-outlined wounds at 6 days post infliction, which are placed side-by-side according to treatment, revealed that the beneficial effects of lysed *L. reuteri* reached particularly high levels of statistical significance (FIGS. 12B and 12C). The increased occurrence of early wound scab detachment at 6 days post-biopsy reflected the faster healing rate conferred by both probiotic and postbiotic *L. reuteri* treatments (Control N=9, *L. reuteri* N=8, Lysed *L. reuteri* N=10). Scale bars: 1000 μm (a). Numbers on the y-axis of bar graphs correspond to the mean±SEM of the parameter assessed;
*p<0.05, ***p<0.0001.

FIG. 16A provides representative photomicrographs depicting oxytocin-ir neurons in the rostral, intermediate, and caudal PVN of mice treated with normal drinking water (Untreated N=9), or live *L. reuteri* (N=8), or lysed *L. reuteri* (N=10). The numerical value in the bottom right corner of top plates represents the distance (in millimeters) posterior to bregma for the rostral, intermediate and caudal PVN. FIG. 16B shows the average number of oxytocin-ir cells observed in the rostral, intermediate, and caudal PVN of mice treated with normal drinking water (Untreated), live *L. reuteri*, or lysed *L. reuteri*. *$p<0.05$ (Tukey post hoc tests following one-way ANOVA).

DETAILED DESCRIPTION OF THE INVENTION

Figure 1:
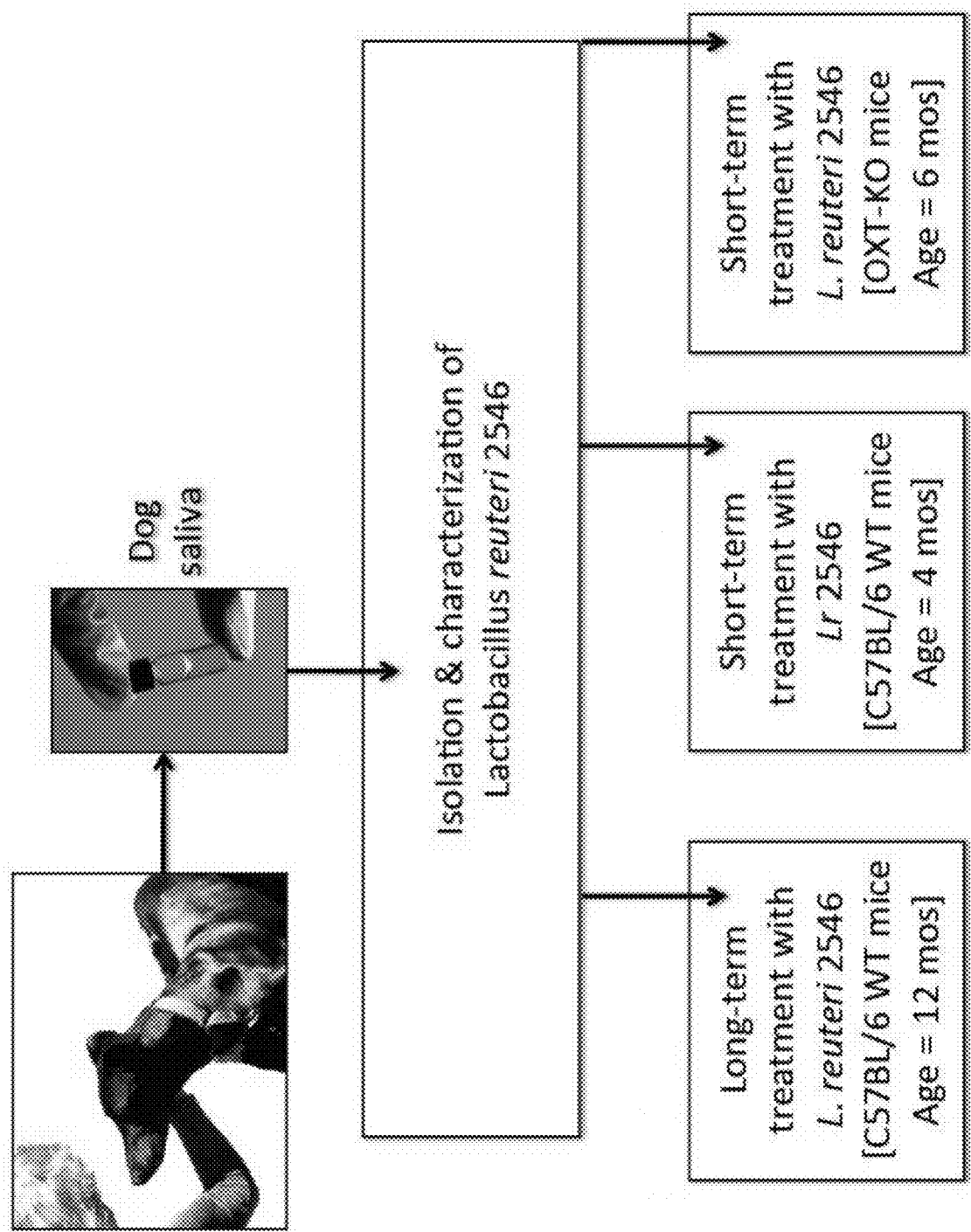
FIG. 1 depicts an experimental overview. Canine *L. reuteri* 2546 was isolated from pet dog saliva, and then fed to mice in their drinking water. Wild type [wt] C57BL/6 mice consuming *L. reuteri* 2546 for long-term or short-term intervals were examined for body weight, inflammatory indices, and plasma oxytocin levels. A final experiment tested the hypothesis of whether oxytocin was necessary for slenderizing effects of *L. reuteri* 2546.

The present inventions relate to the findings that bacteria isolated from dog saliva modulated recipient host body weight. The present inventors found that a *Lactobacillus* species isolated from dog saliva led to lower body weight when fed to C57BL/6 wild type mice (Varian, et al., *J. Prob. Health,* 2016 4(3):1-9, the entire teachings of which are incorporated herein by reference). Mice consuming the canine-borne *L. reuteri* also had elevated oxytocin levels in blood plasma, and exhibited reduced body weight in an oxytocin-dependent manner. Surprisingly, killed (lysed) canine bacteria were sufficient to achieve the physiological effects. Taken together, these findings provide evidence that dog bacteria modulate oxytocin levels and body weight in recipient mice, and thus may help reduce risk of obesity in individuals that cohabitate with pet dogs.

In some aspects, any of the compositions disclosed herein comprise bacteria, for example, *L. reuteri* bacteria. In certain aspects, the *L. reuteri* bacterial species is isolated from dog saliva. The *L. reuteri* bacteria may comprise *L. reuteri* isolate 2546 or *L. reuteri* ATCC 6475. In certain aspects, the *L. reuteri* bacteria do not comprise *L. reuteri* ATCC 6475.

In certain aspects, the *L. reuteri* bacteria are sterile bacteria (e.g., a killed or lysed bacterial strain). In certain aspects, the *L. reuteri* bacteria are killed or lysed in accordance with the methods disclosed herein. In certain aspects, the *L. reuteri* bacteria are killed or sterilized by a method that does not involve heat treatment.

The methods and compositions disclosed herein may be administered to a subject, for example, to increase plasma concentrations of oxytocin in the subject. In certain aspects, the compositions (e.g., compositions comprising killed, lysed or sterile *L. reuteri*) are administered to a subject to treat cachexia. In certain aspects, the compositions (e.g., compositions comprising killed, lysed or sterile *L. reuteri*) are administered to a subject to promote hair growth or to reduce hair loss. In some aspects, the compositions (e.g., compositions comprising killed, lysed or sterile *L. reuteri*) are administered to a subject to promote wound healing. In certain aspects, the compositions (e.g., compositions comprising killed, lysed or sterile *L. reuteri*) are administered to a subject to treat weight gain or obesity. In still other aspects, the compositions (e.g., compositions comprising killed, lysed or sterile *L. reuteri*) are administered to a subject to decrease inflammation. In certain aspects, the compositions (e.g., compositions comprising killed, lysed or sterile *L. reuteri*) are administered to a subject to increase muscle growth, and in further aspects to treat muscle wasting disorders.

The administration of the compositions (e.g., compositions comprising killed, lysed or sterile *L. reuteri*) to a subject, in some aspects, results in increased levels of a growth hormone, and in still other aspects increase the thymus gland size of the subject to whom such composition was administered. In some aspects, the administration of the compositions (e.g., compositions comprising killed, lysed or sterile *L. reuteri*) to a subject, results in improved maternal care, thereby resulting in a higher infant survival rate.

The compositions disclosed herein may be formulated for oral administration. For example, compositions comprising an effective amount of a killed, lysed or sterile *L. reuteri* may be formulated as an orally administered medical food, or as a dietary or nutritional supplement.

As used herein, the term "effective amount" means an amount of the *L. reuteri* (e.g., live or dead) sufficient to achieve a meaningful benefit to the subject (e.g., treating, modulating, curing, preventing and/or ameliorating the obesity or the underlying disease). For example, an effective amount of the compositions that are the subject of the present inventions may be generally determined based on the activity of such compositions. Generally, the amount of the *L. reuteri* administered to a subject in need thereof will depend upon the characteristics of the subject and the severity of their disease or condition. Such characteristics include the condition, general health, age, subjective symptoms, objective appearance, sex and body weight of the subject.

As used herein, a "subject" means a human or animal. Usually the animal is a vertebrate such as a primate, rodent, domestic animal or game animal. In certain embodiments, the subject is a mammal (e.g., a primate or a human). The subject may be an infant, a toddler, a child, a young adult, an adult or a geriatric. The subject may be a smoker, a former smoker or a non-smoker. In some embodiments, the subject is at risk for developing obesity.

While certain compounds, compositions and methods of the present invention have been described with specificity in accordance with certain embodiments, the following examples serve only to illustrate the methods and compositions of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one or the entire group members are present in, employed in or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1

Example 1A

To probe the roles of dog bacteria in weight gain of cohabitating animals, 12 eight-week-old C57BL/6 wt mice were randomly subdivided into groups of six mice per treatment. Mice treated with the canine isolate *L. reuteri* 2546 received it in their drinking water continuously until twelve-months-of-age. Body weight, whole blood cell counts, and body fat histology were evaluated. Terminal blood collections for mice were performed mid-day for all subjects in order to minimize variability due to Circadian rhythms. Animals were housed under 12:12 light cycle conditions and lights turned on at 7 AM.

Example 1B

To test whether oral therapy with killed [sterile] *L. reuteri* 2546 lysate was sufficient for physiological effects, the present inventor examined 18 eight-week-old C57BL/6 wild-type (wt) mice. Experimental mice were divided into groups of six (N=6/treatment group) and then received in their drinking water *L. reuteri* 2546 or lysate of *L. reuteri* 2546 starting at eight-weeks-of-age until fourteen-weeks-of-age. Body weight, whole blood cell counts, plasma oxytocin levels, and body fat histology were evaluated.

Example 1C

To test whether oxytocin is required for fat-inhibiting benefits of oral therapy with canine source *L. reuteri* 2546, the present inventor examined 16 oxytocin-wt (oxt-wt) and 16 knockout (oxt-ko) B6; 129S-Oxttm1Wsy/J mice. Experimental mice were randomly subdivided into groups of eight mice and then received in their drinking water *L. reuteri* 2546 starting at eight weeks of age for a duration of sixteen weeks.
Results
Canine Oral Bacterial Flora Includes *Lactobacillus* Species To test the hypothesis that pet dogs may harbor bacteria beneficial for human body weight control, the present inventor began by sampling canine saliva. Saliva was chosen because one fundamental aspect of the human-canine bond is the gesture of licking that spreads oral cavity microbes on the recipient's skin surface. Recognizing that *L. reuteri* ATCC 6475 bacteria collected from human milk was found to up-regulate oxytocin when fed to mouse models [30], and that oxytocin is pivotal in canine-human bonds and weight control [2,36-38], the present inventor postulated that dogs may harbor and spread similar microbes that modulate oxytocin and impart a slim physique in the recipient. To test this possibility, the present inventor first interrogated the canine oral microbiome using molecular assays and microbial culture (FIG. 1).

Using generic PCR primers to amplify all *Lactobacillus* spp in dog saliva, we found nonspecific evidence of *Lactobacillus* spp in the oral cavity samples of eight [8/8] pet dogs that were examined (FIG. 6A). Elsewhere, it has already well-established that pet dogs may disseminate organisms such as *L. johnsonii* in household dust that lower risk of asthma and other inflammatory disorders in cohabitating humans [14].

Figures 2A, 2B, 2C, 2D:
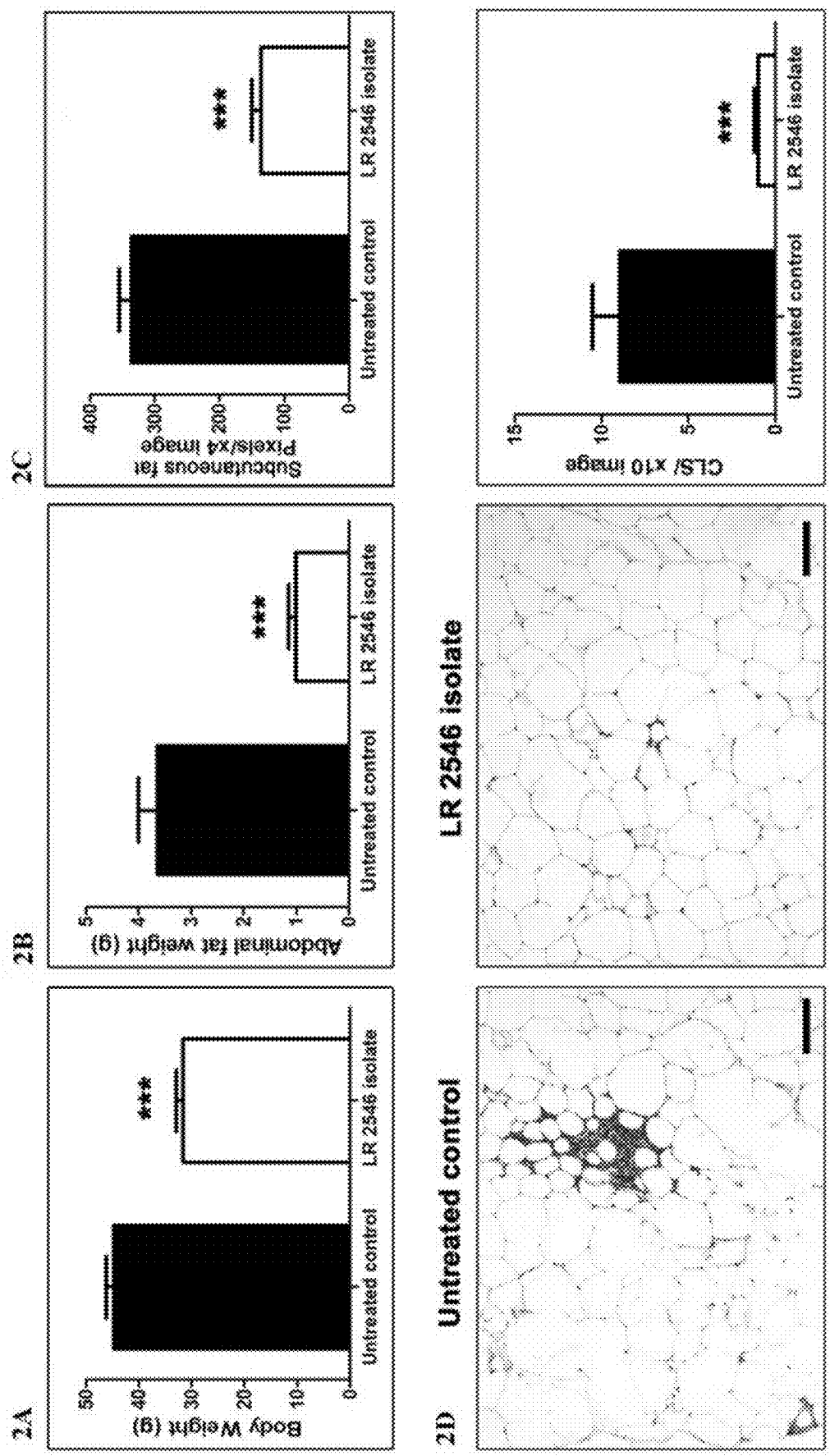
FIGS. 2A-2D demonstrate that the canine *L. reuteri* 2546 isolate recapitulates key probiotic health benefits in mice. Mice consuming *L. reuteri* 2546 for nine months had significantly (FIG. 2A) lower body weights, and reduced accumulations of (FIG. 2B) abdominal and (FIG. 2C) subcutaneous fat compared to untreated age-matched control mice.
Figure 3:
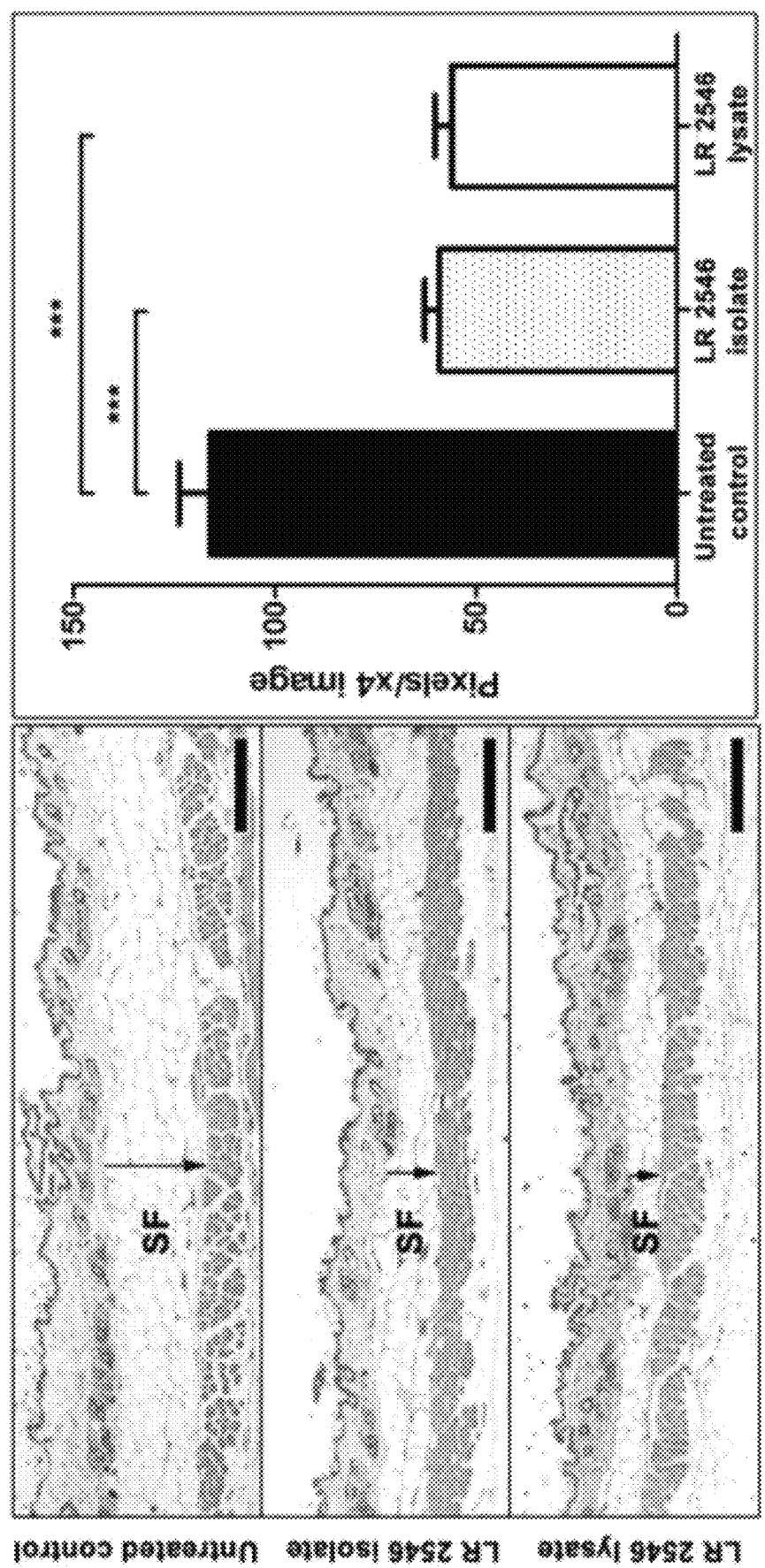
FIG. 3 demonstrates that a single month of *L. reuteri* 2546 treatment resulted in reduced subcutaneous fat in mice. The histomorphometrical assessment of subcutaneous fat thickness in mice shows that both live and killed 2546 bacterial cells when orally consumed act to reduce the thickness of the subcutaneous fat (SF) layer at statistically significant levels. Hematoxylin and Eosin. Scale bars: 250 μm. Numbers on the y-axis of bar graph corresponds to the mean±SEM of SF layer thickness measured in image pixels; ***$p<0.0001$.

To determine whether canine oral bacteria may impart health benefits such as slender physique to a cohabitating animal host, the present inventor isolated candidate *Lactobacillus* spp using standard microbiology techniques. Based upon colony growth properties, and microscopic morphology of short rods forming chains, a tractable gram-positive rod isolate was confirmed to be *L. reuteri* based on the composite of gram stain/morphology, biochemical tests, and molecular tests (FIGS. 6B-6D). Afterwards, C57BL/6 wild type mice were fed this purified microbe as a surrogate to mimic canine-human contact. The *L. reuteri* isolate 2546 was cultivated as previously described [34,35], and fed $3 \times 10^5$ CFU per day to C57BL/6 mice in their regular drinking water to test the bacteria-body weight hypothesis. Age-matched controls received regular drinking water.
Mice Exposed to Bacteria from Dog Saliva are More Slender than Controls Based on our knowledge that consumption of *Lactobacillus* ATCC 6475 was sufficient to inhibit inflammation and age-associated obesity in mouse models [39], and *Lactobacillus rhamnosus* CGMCC1.3724 stimulates weight loss in obese humans [40], the present inventor tested the microbe-obesity hypothesis using mice exposed orally to the canine-sourced *L. reuteri* 2546 and compared them with untreated control animals. After nine months of daily feeding with *L. reuteri*, the present inventor discovered that *L. reuteri* 2546-treated mice had significantly lower body weight relative to the control animals (FIG. 2A). Further, abdominal fat (FIG. 2B) and subcutaneous fat (FIG. 2C) were significantly less in mice receiving canine-sourced *L. reuteri* 2546 in drinking water.

To determine whether body fat pathology was altered by exposure to the dog microbe, the present inventor microscopically examined abdominal fat from mice of both groups. Similar to what was reported previously using a different strain of *L. reuteri* [39], the present inventor found that the canine *L. reuteri* isolate 2546 protected mice from adipose tissue lesions characteristic of obese or aged mice. The histological analysis of abdominal fat revealed that *L. reuteri* 2546-treated mice had significantly fewer "crown-like structures" (CLS), which is the typical lesion of adipocyte death-related inflammation, and focal pyogranulomatous inflammation (FIG. 2D).

Lysed (Sterile) Bacteria are Sufficient for Physiological Effects in Mice

Figures 4A, 4B, 4C:
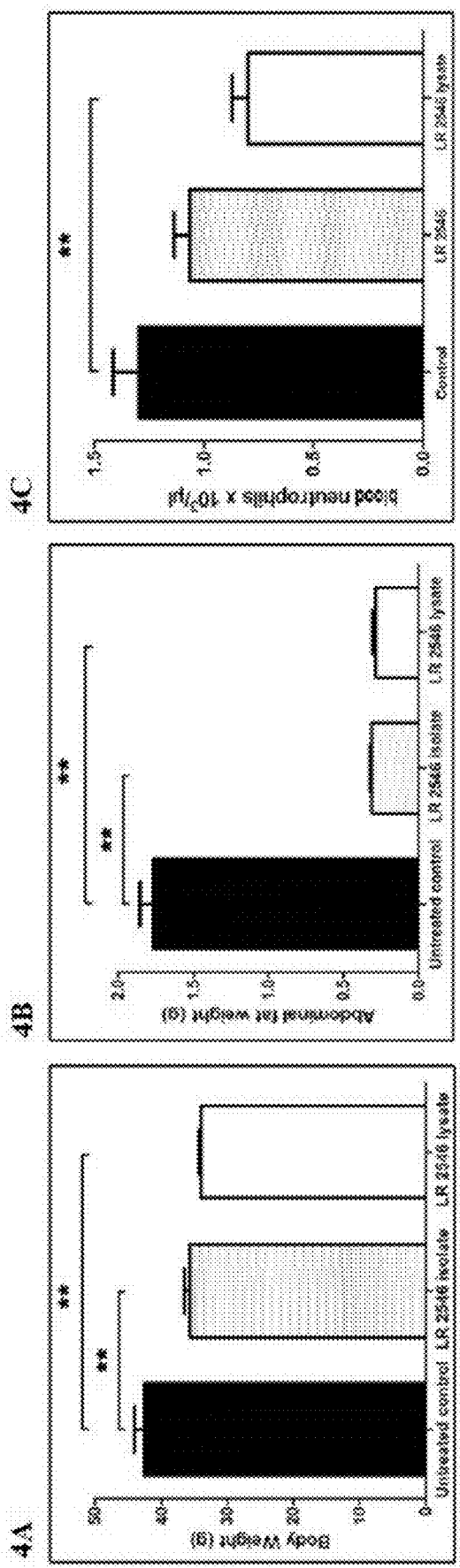
FIGS. 4A-4C illustrate that short-term treatment with *L. reuteri* 2546 contributes to slimmer phenotypes and lower systemic inflammatory tone in mice. The oral consumption of either live or lysed probiotic bacteria cells reduces the body weight (FIG. 4A), abdominal fat weight (FIG. 4B) and numbers of neutrophils in the blood of mice (FIG. 4C). Numbers on the y-axis of bar graph corresponds to the mean±SEM of SF layer thickness measured in image pixels; **$p<0.001$.

Studies involving pet dogs show reduced risk for asthma in humans due to exposure of dust when cohabitating with pet dogs [14]. To test whether living bacteria are actually required for beneficial effects, purified canine microbe 2546 was rendered sterile by lysis before being fed to mice in their drinking water for six weeks duration. Surprisingly, the present inventor found that exposure to sterile lysed forms of the same bacteria were sufficient for lower body weight and reduced subcutaneous and visceral fat (FIGS. 3 and 4A-4C). In earlier studies it was determined that routinely consuming *L. reuteri* ATCC 6475 also lowered systemic inflammatory tone [39]. To test this possibility, examination of whole blood counts revealed that circulating neutrophils were significantly fewer in mice undergoing treatment with *L. reuteri* 2546 for four weeks (FIG. 4C). The finding that lysates were sufficient for physiological effect raises the possibility that colonization with microbes or influence of microbial communities is not necessarily required for benefits shared between cohabitating hosts.

Canine Bacteria Induce Neuropeptide Hormone Oxytocin

Knowing that oxytocin inhibits weight gain in rodent models [21,41], and that oxytocin modulates appetite in human subjects [29], plasma levels of oxytocin were tested in mice of long- and short-term experiments. The present inventor found significantly elevated blood plasma oxytocin levels in C57BL/6 mice getting canine-sourced *L. reuteri* 2546 in their water, when compared with age-matched controls drinking regular water (FIGS. 5A and 5B). These observations matched earlier reports of elevated plasma oxytocin levels after feeding another *L. reuteri* isolate from human milk (ATCC 6475) that was demonstrated to improve systemic wound healing capacity [30]. Interestingly, lysed *L. reuteri* 2546 was also potent for increasing the systemic levels of plasma oxytocin in mice (FIG. 5B). Altogether, these findings suggest novel microbe-based strategies for body weight control and psychological well-being. The consistent up-regulation of oxytocin after eating *L. reuteri* 2546 led the present inventor to test whether oxytocin is required for the lowered body weight phenomenon.

Consumption of *L. reuteri* Reduces Risk for Obesity in an Oxytocin-Dependent Manner Recognizing that oxytocin inhibits weight gain in rodent models [21,41] and in humans [29], the present inventor challenged oxytocin-deficient B6; 129S-Oxttm1Wsy/J mutant mice with canine-sourced *L. reuteri* 2546 to determine whether this neurotropic hormone oxytocin was essential for *L. reuteri* 2546-induced weight control. The present inventor found that mice globally lacking oxytocin did not benefit from microbe-induced body weight effects (FIGS. 5C and 5D). This is consistent with the other data; in particular, using oxytocin-deficient B6; 129SOxttm1Wsy/J mutant mice, it was previously shown that inflammation, and specifically neutrophils, have a reciprocal relationship with oxytocin in the wound repair process [30]. The apparent requirement for oxytocin-competency in this model system led the present inventor to conclude that microbe-driven oxytocin contributed to the lean outcome of mice.

Discussion

Here the present inventor tested whether common commensal bacteria in pet dogs may help explain the leaner body weight of dog owners. Using a C57BL/6 wild type mouse model as a surrogate for human subjects, the present inventor found that mice consuming *L. reuteri* 2546 isolated from pet dog saliva exhibited less age-associated weight gain in an oxytocin-dependent manner. Interestingly, lysed (sterile) forms of the same bacteria were also sufficient to up-regulate mouse plasma oxytocin and lower circulating neutrophils, fat pathology, and body weights, suggesting future therapeutic possibilities for sterile microbial fractions in good physical and mental health. Taken together, these studies in mice provide evidence that canine microbiota may contribute to lower body weights—and simultaneously serve to strengthen the human-animal bond—due to microbe-induced activities of the hormone oxytocin.

Epidemiological data showing lower prevalence of allergic diseases among those living on farms or with pets during childhood support this beneficial microbe concept, thus sparking intense research interest in this topic [6-13]. The "hygiene hypothesis" theory is based on associations between the modern living-associated decrease in infectious agent exposures and the commensurate increase in allergies and autoimmune diseases. Earlier work from our own lab [39] and other labs [42-53] begin to connect-the-dots between microbes, inflammation, and obesity. Indeed, it was previously shown that exposure to dietary *L. reuteri* strains ATCC 6475 [39] or ATCC 4659 [53] led to less weight gain in mouse models. Another recent study showed that household dogs, specifically, may disseminate *Lactobacillus* spp in household dust that lower risk of asthma and other inflammatory disorders in cohabitating humans [14,54]. It is an attractive idea that certain microbes can be strategically applied to stimulate beneficial host pathways as a replacement for microbes lost due to antibiotics and routine sanitary practices.

At the same time that bacteria in dog saliva, or microbiota from other pet or farm animals, may have beneficial properties [55], caution is warranted involving zoonotic organisms that readily transmit diseases between species. Common examples include plague from infected fleas [56]. Also, significantly higher infection rates of Chagas disease were evident in humans who slept with their pet dog [57]. *Bartonella hensalae* infection was confirmed by serologic testing of a 50-year-old man from Japan, who lived with a dog that often licked his face [58]. *Pasteurella* sp infections have also been associated with dogs licking human faces [59,60]. Cases exist where organisms from dog saliva have identical biochemical patterns and genotypic similarities with isolates in human infections [61-63], supporting that dog saliva is the mode of bacterial transmission [64]. Thus, microbe strategies that maximize the benefits of bacteria exposures and simultaneously lower risks of zoonotic diseases are a practical goal.

These present findings linking *Lactobacillus* spp with a more slender physique are not entirely surprising since consumption of *L. reuteri* ATCC 6475 was proven sufficient to inhibit inflammation and age-associated obesity in mouse models [39]. Similar weight loss was shown in obese humans who consumed purified *L. rhamnosus* [40]. It was also previously shown that microbe-induced oxytocin modulates host immunity by inducing a more rapid return to health after injury [30]. Most notable in those earlier studies were expedited influxes of neutrophils with more rapid wound repair afterwards when treated with *L. reuteri* ATCC 6475, a phenomenon that was reliant upon oxytocin as shown in B6; 129S-Oxttm1Wsy/J mutant mice [30,65]. In those studies, central in beneficial effects of feeding *L. reuteri* ATCC 6475 was recruitment of homeostatic CD4+ CD25+Foxp3+regulatory T ($T_{reg}$) cells that are otherwise known to suppress deleterious inflammatory responses [66]. The superior physiological role of $T_{reg}$ cells is to prevent immunopathology after a host insult [67], a feature that can be utilized to host benefit in maintaining immune homeostasis. Many questions remain to be answered about the host range and other physiological properties of canine *L. reuteri* 2546.

In earlier studies, *L. reuteri* ATCC 6475-induced up-regulation of plasma oxytocin was a vagus nerve-dependent phenomenon, suggesting central nervous system (CNS) involvement [30]. Other work has shown a release of oxytocin from somatodendrites and axonal terminals within the CNS implicated in both control of energy balance the formation of prosocial behaviors [41]. Romero et al. and Nagasawa et al. [16,68] found that giving dogs exogenous oxytocin supplements causes them to display stronger social bonding behavior, both with people and other dogs. To the same extent, oxytocin has been shown to benefit antisocial behaviors in autism spectrum disorder (ASD) in humans [69,70]. Interestingly, mice eating *L. reuteri* ATCC 6475 in earlier studies were also shown to improve maternal care with higher infant survival rates [71]. Unlike the short half-life of exogenous supplements of oxytocin, the plasma elevations seen in the present mice are a consistent and reproducible effect [30], making bacteria or bacterial products a possible therapy for mental health. It remains to be proven whether microbe-induced oxytocin in these murine models originates primarily from the hypothalamus or from other peripheral sources [72-76]. Nonetheless, our results suggest that gut bacteria-induced oxytocin may explain data linking gut microbiome dysbiosis with neuropsychological disorders, including autism [77,78].

One interesting question is whether microbiota or microbe-stimulated oxytocin inhibits weight gain at the expense of host muscle mass. Indeed, emerging work shows oxytocin does exactly the opposite, that oxytocin helps build host muscle mass [79]. Feeding of a human isolate of *L. reuteri* (ATCC 6475) to mice was also shown to inhibit muscle wasting disorders, associated with an increase in growth hormone levels and also a larger thymus gland size [80]. Likewise, the same strain of *L. reuteri* ATCC 6475 was previously shown to stimulate an increase in serum thyroid hormone T4 levels in mice [81] commensurate with more slender physique. Taken together, there is precedent for microbiota, and *L. reuteri* isolates in particular, to stimulate systemic hormone secretion that re-directs energy toward muscle growth and away from fat storage.

Recognizing that bacteria from dogs and other cohabitating pet, food and fiber animals carry zoonotic risks, a potentially important finding in the present study involves benefit of exposures to lysed sterile forms of bacteria. These intriguing data also raise the possibility that colonization with live microbes or microbial communities is not required for physiological benefits, whether at an individual level or shared between cohabitating hosts. An additional benefit is that sterile extracts of microbes have fewer health risks for immune-compromised patients, lowering risk of microbial overgrowth in patients who may otherwise suffer inappropriate immune responses. Some earlier work has suggested that killed bacteria or their extracts have healthful anti-inflammatory properties, in particular during inflammatory bowel conditions [82-86]. Precise characterization of the dog bacterial extract and potential in human subjects remains to be determined. Nonetheless, these data reveal vast potential for sterile microbe extracts in good physical, social and mental health.

In conclusion, these data build upon earlier studies in mice showing that *L. reuteri* ATCC 6475 from human breast milk lowers body weight and up-regulates oxytocin levels in blood. The present inventors found that bacteria isolated from dog saliva, *L. reuteri* 2546, may regulate inflammation and host body weight involving mechanisms of oxytocin, raising interesting evolutionary cohabitation questions and therapeutic possibilities. The discovery that sterile microbial products also achieve similar benefits paves the way for novel therapeutics for good health.

Materials and Methods

Animals

C57BL/6 wild type (wt), oxytocin-wt (oxt-wt) and oxytocin knockout (oxt-ko) B6; 129S-Oxttm1Wsy/J mice (purchased initially from Jackson labs; Bar Harbor, Me.) were used in three separate experiments (FIG. 1). Mice were housed and handled in Association for Assessment and Accreditation of Laboratory Animal Care (AAALAC)-accredited facilities using techniques and diets including *Lactobacillus reuteri* as specifically approved by Massachusetts Institute of Technology's (MIT) Committee on Animal Care (CAC). Mice were housed under standard 12:12 light cycle conditions with lights on at 7 AM. Mice were fed a standard control chow Purina RMH3000.

Mice were bred in-house to achieve experimental groups. Each experiment included 5-15 animals per group with one or two replications (total N=10-30 mice examined per group) unless otherwise specified. For the initial studies, C57BL/6 wt mice received *Lactobacillus reuteri* 2546 isolated from dog saliva. To test putative roles for microbe-induced oxytocin in obesity, oxt-ko mice and their oxt-wt littermates entered experiments at eight weeks of age. At the conclusion of the study mice were euthanized with $CO_2$ overdose, and were examined as described below. Eight pet dogs served as saliva microbe donors as approved by the MIT-CAC. Saliva was collected from these dogs in the morning before feeding using sterile swabs [Puritan Sterile Polyester Tipped applicators Guilford, Me. Ref: 25-806 1PD] in 1.5 ml centrifuge tubes (Safeseal Microcentrifuge Tubes, Sorenson Bioscience Inc. Salt Lake City, Utah Cat #16070). Bacteria were purified from dog saliva as described in detail below PCR of Dog Saliva for all *Lactobacillus* Species Saliva was collected from eight pet dogs and prepared using High Pure PCR Template kit (Roche Diagnostics) was used without changes to the manufacturer's directions to isolate DNA from the canine saliva. DNA was measured using Nano Drop Spectrophotometer (Thermo Scientific). *Lactobacillus* spp PCR was performed according to the LactoF and LactoR primers (Integrated Data Technologies) described by Byun et al. [31]. LactoF: 5'-TGG AAA CAG RTG CTA ATA CCG-3' (SEQ ID NO: 1) and LactoR: 5'-GTC CAT TGT GGA AGA TTC CC-3' (SEQ ID NO: 2) with amplification. Initial denaturation was 95 degrees Celsius for 15 minutes, then with 40 cycles of Denaturing at 95 degrees Celsius for 5 seconds, then annealing at 62 degrees Celsius for 1 minute, and Extension: 72 degrees Celsius for 1 minute. A final extension at 72 degrees Celsius for 5 minutes with the resting temperature at 4 degrees Celsius until utilized for gel separation. PCR products were checked on 2% agarose gel (Sigma) using the Kb+ladder (Invitrogen 10787-018) as a molecular weight marker.

Isolation, Characterization and Confirmation of *L. reuteri* 2546

Saliva from pet dog #3 was cultivated in classical media, with bacteria isolated as previously described [32]. Subsequently, individual colonies were selected and grown on Sheep blood agar plates (Remel Blood Agar TSA w/Sheep Blood Plate, Lenera, Kans. Ref #R01202) for further characterization [32]. Isolate 2546 was found to have colony growth characteristics, microscopic morphology, and be positive for Gram stain, indicating the use of the API 50

CHL system for further identification. The identity of the bacteria was further characterized using API 50 CHL (Biomerieux, France) strips, consisting of 50 Biochemical tests to identify *Lactobacillus* and related genera, was used according to manufacturer's instructions. Specifically, the 2546 isolate was grown according to manufacturer's instructions and collected after 24 hours with a sterile swab and inoculated into the suspension medium (Biomerieux, France). Interpretation of carbohydrate fermentations were dictated by the manufacturer's instructions and analyzed with the APIweb database (Biomerieux, France). Finally, pure bacterial culture was tested for genetic identity using PCR with genus specific primers, as below.

*Lactobacillus reuteri* PCR was performed according to the L-reu-1 and L-reu-4 primers (Integrated Data Technologies) described by Dommels et al. [33]. L-reu-1: 5'-CAG ACA ATC TTT GAT TGT TTA-3' (SEQ ID NO: 3) and L-REU-4: 5'-GTC TGT TGG TTT GGG CTC TTC-3' (SEQ ID NO: 4) with Amplification of Initial denaturation 95 degrees Celsius for 5 minutes and then 35 cycles of Denaturing: 95 degrees Celsius for 1 minute, Annealing: 60 degrees Celsius for 1 minute, and Extension: 72 degrees Celsius for 1 minute. A final Extension at 72 degrees Celsius for 8 minutes with the resting temperature at 4 degrees Celsius until utilized for gel separation. PCR products were checked on 2% agarose gel (Sigma) using the Kb+ladder (Invitrogen 10787-018) as a molecular weight marker.

Production of Sterile Microbe Lysate

*L. reuteri* 2546 was cultivated using methods as previously described [34,35], confirmed for purity by morphology and gram strain, and then suspended in sterile 1×PBS and measured for concentration with a spectrophotometer. A bacteria pellet was obtained by centrifugation for 10 minutes at 14,000 rpm and then re-suspended and incubated in a Lysozyme STET buffer for 4 hours at 37 degrees Celsius. Bacteria buffer was centrifuged for 10 minutes at 7,500 rpm to obtain a pellet, that was subsequently washed 2× and then re-suspended in 1×PBS before lysing by sonication in an ice water bath at 20 kHz and the amplitude of 30% intensity for one-minute-on-then one-minute-off for 25 minutes. Lysed bacteria were then centrifuged for 15 minutes at 4,000 rpm with the supernatant being collected as the final product. The supernatant was then confirmed to be sterile using growth by the streak plate method with no growth after three days. Bacterial lysate was stored in 1 ml aliquots in a −80 degrees Celsius until use.

Special Microbial Treatments for Animals

Mice were fed standard rodent chow (RMH 3000; Purina Labs, St Louis Mo.). Subsets of animals were supplemented orally with a strain of *L. reuteri* 2546, originally isolated from dog saliva, and subsequently cultivated as described elsewhere [34,35], using a supply dosage of $3.5 \times 10^5$ organisms/mouse/day continuously in drinking water. For the initial studies, C57BL/6 wt mice received *L. reuteri* as above, or, alternatively, regular drinking water. For Example 1B, lysate was delivered at the same concentration in drinking water. For subsequent studies, oxt-ko and their littermate oxt-wt mice began drinking *L. reuteri* 2546 organisms, as above, starting at 6-8 weeks of age, and then underwent analyses at 24 weeks of age. Drinking water was replaced twice weekly to minimize variability in microbial exposure levels. Control animals received regular drinking water.

Complete Blood Cell Counts

Whole blood was collected by cardiac puncture from unconscious animals prior to necropsy and suspended in EDTA to prevent clotting. Automated neutrophil counts were then performed using mouse parameters in a HemaVet 950FS (Drew Scientific, Oxford Conn.). Terminal blood collections for mice were performed mid-day for all subjects in order to minimize variability due to Circadian rhythms.

Measurement of Plasma Oxytocin Levels

Whole blood was collected terminally by cardiac puncture under general anesthesia to obtain plasma. Blood was collected into pre-chilled 5 ml EDTA tubes with 250 KIU of aprotinin, and refrigerated until processing. Plasma was isolated by centrifugation at 1800 g, 15 minutes, 4° C., and then stored in aliquots at −70° C. Plasma was then tested commercially by an outside laboratory with internal validations (AniLytics, Inc., Gaithersburg, Md.). Euthanasia for mice was performed mid-day for all subjects (n=10 per group) to minimize variability due to Circadian rhythms.

Histopathology and Histomorphometry

Formalin-fixed tissues were embedded in paraffin, cut at 4-5 µm, and stained with hematoxylin and eosin (HE). CLS counting in abdominal fat sections and measurements of subcutaneous fat thickness were done as previously described [39]. Briefly, multiple images of comparable histological fields were taken at x10 (for crown-like structures=CLS) or x4 (subcutaneous fat) magnification. Twenty images per experimental group were randomly selected and used for assessments using the Image J image processing and analysis program (NIH, Bethesda, Md.).

Statistical Analyses

For all statistical analyses the Mann-Whitney U test (Graphpad Prism version 4.0 for windows, Graph-Pad software, San Diego, Calif., USA) was used. Effects were considered to be significant at $p<0.05$.

REFERENCES

1. Knight S, Edwards V (2008) In the company of wolves: the physical, social, and psychological benefits of dog ownership. J Aging Health 20: 437-455.
2. Coleman K J, Rosenberg D E, Conway T L, Sallis J F, Saelens B E, et al. (2008) Physical activity, weight status, and neighborhood characteristics of dog walkers. Prev Med 47: 309-312.
3. Ogden C L, Carroll M D, Kit B K, Flegal K M (2012) Prevalence of obesity in the United States, 2009-2010. NCHS Data Brief: 1-8.
4. Sirard J R, Patnode C D, Hearst M O, Laska M N (2011) Dog ownership and adolescent physical activity. Am J Prev Med 40: 334-337.
5. Booth K M, Pinkston M M, Poston W S (2005) Obesity and the built environment. J Am Diet Assoc 105: S110-117.
6. Hesselmar B, Aberg N, Aberg B, Eriksson B, Bjorksten B (1999) Does early exposure to cat or dog protect against later allergy development? Clin Exp Allergy 29: 611-617.
7. Linneberg A, Nielsen N H, Madsen F, Frolund L, Dirksen A, et al. (2001) Factors related to allergic sensitization to aeroallergens in a cross-sectional study in adults: The Copenhagen Allergy Study. Clin Exp Allergy 31: 1409-1417.
8. Kilpelainen M, Terho E O, Helenius H, Koskenvuo M (2002) Childhood farm environment and asthma and sensitization in young adulthood. Allergy 57: 1130-1135.
9. von Hertzen L, Makela M J, Petays T, Jousilahti P, Kosunen T U, et al. (2006) Growing disparities in atopy between the Finns and the Russians: a comparison of 2 generations. J Allergy Clin Immunol 117: 151-157.

10. Oryszczyn M P, Annesi-Maesano I, Charpin D, Kauffmann F (2003) Allergy markers in adults in relation to the timing of pet exposure: the EGEA study. Allergy 58: 1136-1143.
11. Simpson A, Custovic A (2005) Pets and the development of allergic sensitization. Curr Allergy Asthma Rep 5: 212-220.
12. Bufford J D, Gern J E (2007) Early exposure to pets: good or bad? Curr Allergy Asthma Rep 7: 375-382.
13. Mandhane P J, Sears M R, Poulton R, Greene J M, Lou W Y, et al. (2009) Cats and dogs and the risk of atopy in childhood and adulthood. J Allergy Clin Immunol 124: 745-750 e744.
14. Fujimura K E, Demoor T, Rauch M, Faruqi A A, Jang S, et al. (2014) House dust exposure mediates gut microbiome *Lactobacillus* enrichment and airway immune defense against allergens and virus infection. Proc Natl Acad Sci USA 111: 805-810.
15. Nagasawa M, Kikusui T, Onaka T, Ohta M (2009) Dog's gaze at its owner increases owner's urinary oxytocin during social interaction. Horm Behav 55: 434-441.
16. Nagasawa M, Mitsui S, En S, Ohtani N, Ohta M, et al. (2015) Social evolution. Oxytocin-gaze positive loop and the coevolution of human-dog bonds. Science 348: 333-336.
17. Deblon N, Veyrat-Durebex C, Bourgoin L, Caillon A, Bussier A L, et al. (2011) Mechanisms of the anti-obesity effects of oxytocin in diet-induced obese rats. PLoS One 6: e25565.
18. Kublaoui B M, Gemelli T, Tolson K P, Wang Y, Zinn A R (2008) Oxytocin deficiency mediates hyperphagic obesity of Sim1 haploinsufficient mice. Mol Endocrinol 22: 1723-1734.
19. Maejima Y, Iwasaki Y, Yamahara Y, Kodaira M, Sedbazar U, et al. (2011) Peripheral oxytocin treatment ameliorates obesity by reducing food intake and visceral fat mass. Aging (Albany N.Y.) 3: 1169-1177.
20. Maejima Y, Sedbazar U, Suyama S, Kohno D, Onaka T, et al. (2009) Nesfatin-1-regulated oxytocinergic signaling in the paraventricular nucleus causes anorexia through a leptin-independent melanocortin pathway. Cell Metab 10: 355-365.
21. Morton G J, Thatcher B S, Reidelberger R D, Ogimoto K, Wolden-Hanson T, et al. (2012) Peripheral oxytocin suppresses food intake and causes weight loss in diet-induced obese rats. Am J Physiol Endocrinol Metab 302: E134-144.
22. Zhang G, Bai H, Zhang H, Dean C, Wu Q, et al. (2011) Neuropeptide exocytosis involving synaptotagmin-4 and oxytocin in hypothalamic programming of body weight and energy balance. Neuron 69: 523-535.
23. Zhang G, Cai D (2011) Circadian intervention of obesity development via restingstage feeding manipulation or oxytocin treatment. Am J Physiol Endocrinol Metab 301: E1004-1012.
24. den Hertog C E, de Groot A N, van Dongen P W (2001) History and use of oxytocics. Eur J Obstet Gynecol Reprod Biol 94: 8-12.
25. Braude R, Mitchell K G (1952) Observations on the relationship between oxytocin and adrenaline in milk ejection in the sow. J Endocrinol 8: 238-241.
26. Striepens N, Kendrick K M, Maier W, Hurlemann R (2011) Prosocial effects of oxytocin and clinical evidence for its therapeutic potential. Front Neuroendocrinol 32: 426-450.
27. Yamasue H, Yee J R, Hurlemann R, Rilling J K, Chen F S, et al. (2012) Integrative approaches utilizing oxytocin to enhance prosocial behavior: from animal and human social behavior to autistic social dysfunction. J Neurosci 32: 14109-14117.
28. Montag C, Brockmann E M, Bayerl M, Rujescu D, Muller D J, et al. (2013) Oxytocin and oxytocin receptor gene polymorphisms and risk for schizophrenia: a case-control study. World J Biol Psychiatry 14: 500-508.
29. Lawson E A, Marengi D A, DeSanti R L, Holmes T M, Schoenfeld D A, et al. (2015) Oxytocin reduces caloric intake in men. Obesity (Silver Spring) 23: 950-956.
30. Poutahidis T, Kearney S M, Levkovich T, Qi P, Varian B J, et al. (2013) Microbial Symbionts Accelerate Wound Healing via the Neuropeptide Hormone Oxytocin. PLoS One 8: e78898.
31. Byun R, Nadkarni M A, Chhour K L, Martin F E, Jacques N A, et al. (2004) Quantitative analysis of diverse *Lactobacillus* species present in advanced dental caries. J Clin Microbiol 42: 3128-3136.
32. Holt J G K, N. R.; Sneath, P. H.; Staley, J. T.; Williams, S. T. (1994) Bergey's manual of determinative bacteriology. Baltimore, Md., USA: Williams & Wilkins.
33. Dommels Y E M, Kemperman R A, Zebregs YEMP, Draaisma R B, Jol A, et al. (2009) Survival of *Lactobacillus reuteri* DSM 17938 and *Lactobacillus rhamnosus* G G in the Human Gastrointestinal Tract with Daily consumption of a Low-Fat Probiotic Spread. Appl Environ Microbiol 75: 6198-6204.
34. Saulnier D M, Santos F, Roos S, Mistretta T A, Spinier J K, et al. (2011) Exploring metabolic pathway reconstruction and genome-wide expression profiling in *Lactobacillus reuteri* to define functional probiotic features. PLoS One 6:e18783.
35. Levkovich T, Poutahidis T, Smillie C, Varian B J, Ibrahim Y M, et al. (2013) Probiotic bacteria induce a 'glow of health'. PLoS One 8: e53867.
36. Levine G N, Allen K, Braun L T, Christian H E, Friedmann E, et al. (2013) Pet ownership and cardiovascular risk: a scientific statement from the American Heart Association. Circulation 127: 2353-2363.
37. Beetz A, Uvnas-Moberg K, Julius H, Kotrschal K (2012) Psychosocial and psychophysiological effects of human-animal interactions: the possible role of oxytocin. Front Psychol 3: 234.
38. Matchock R L (2015) Pet ownership and physical health. Curr Opin Psychiatry 28:386-392.
39. Poutahidis T, Kleinewietfeld M, Smillie C, Levkovich T, Perrotta A, et al. (2013) Microbial reprogramming inhibits Western diet-associated obesity. PLoS One 8:e68596.
40. Sanchez M, Darimont C, Drapeau V, Emady-Azar S, Lepage M, et al. (2014) Effect of *Lactobacillus rhamnosus* CGMCC1.3724 supplementation on weight loss and maintenance in obese men and women. Br J Nut 111: 1507-1519.
41. Blevins J E, Ho J M (2013) Role of oxytocin signaling in the regulation of body weight. Rev Endocr Metab Disord 14: 311-329.
42. Kallus S J, Brandt L J (2012) The intestinal microbiota and obesity. J Clin Gastroenterol 46: 16-24.
43. Fried S K, Bunkin D A, Greenberg A S (1998) Omental and subcutaneous adipose tissues of obese subjects release interleukin-6: depot difference and regulation by glucocorticoid. J Clin Endocrinol Metab 83: 847-850.
44. Weisberg S P, McCann D, Desai M, Rosenbaum M, Leibel R L, et al. (2003) Obesity is associated with macrophage accumulation in adipose tissue. J Clin Invest 112:1796-1808.

45. Turnbaugh P J, Ley R E, Mahowald M A, Magrini V, Mardis E R, et al. (2006) An obesity-associated gut microbiome with increased capacity for energy harvest. Nature 444: 1027-1031.
46. Winer S, Paltser G, Chan Y, Tsui H, Engleman E, et al. (2009) Obesity predisposes to Th17 bias. Eur J Immunol 39: 2629-2635.
47. Hooper L V, Littman D R, Macpherson A J (2012) Interactions between the microbiota and the immune system. Science 336: 1268-1273.
48. Kim S W, Park K Y, Kim B, Kim E, Hyun C K (2013) *Lactobacillus rhamnosus* G G improves insulin sensitivity and reduces adiposity in high-fat diet-fed mice through enhancement of adiponectin production. Biochem Biophys Res Commun 431: 258-263.
49. Oksaharju A, Kooistra T, Kleemann R, van Duyvenvoorde W, Miettinen M, et al. (2012) Effects of probiotic *Lactobacillus rhamnosus* G G and *Propionibacterium freudenreichii* ssp. *shermanii* J S supplementation on intestinal and systemic markers of inflammation in ApoE*3Leiden mice consuming a high-fat diet. Br J Nutr: 1-9.
50. Kang J H, Yun S I, Park H O (2010) Effects of *Lactobacillus* gasseri BNR17 on body weight and adipose tissue mass in diet-induced overweight rats. J Microbiol 48: 712-714.
51. Naito E, Yoshida Y, Makino K, Kounoshi Y, Kunihiro S, et al. (2011) Beneficial effect of oral administration of *Lactobacillus casei* strain Shirota on insulin resistance in diet-induced obesity mice. J Appl Microbiol 110: 650-657.
52. Axling U, Olsson C, Xu J, Fernandez C, Larsson S, et al. (2012) Green tea powder and *Lactobacillus plantarum* affect gut microbiota, lipid metabolism and inflammation in high-fat fed C57BL/6J mice. Nutr Metab (Lond) 9: 105.
53. Fak F, Backhed F (2012) *Lactobacillus reuteri* prevents diet-induced obesity, but not atherosclerosis, in a strain dependent fashion in Apoe−/− Mice. PLoS One 7: e46837.
54. Musso G, Gambino R, Cassader M (2010) Obesity, diabetes, and gut microbiota: the hygiene hypothesis expanded? Diabetes Care 33: 2277-2284.
55. Hart B L, Powell K L (1990) Antibacterial properties of saliva: role in maternal periparturient grooming and in licking wounds. Physiology & Behavior 48: 383-386.
56. Gould L H, Pape J, Ettestad P, Griffith K S, Mead P S (2008) Dog-associated risk factors for human plague. Zoonoses Public Health 55: 448-454.
57. Gurtler R E, Cecere M C, Rubel D N, Petersen R M, Schweigmann N J, et al. (1991) Chagas disease in northwest Argentina: infected dogs as a risk factor for the domestic transmission of *Trypanosoma cruzi*. Trans R Soc Trop Med Hyg 85: 741-745.
58. Maruyama S, Izumikawa K, Miyashita M, Kabeya H, Mikami T, et al. (2004) First isolation of *Bartonella henselae* type I from a cat-scratch disease patient in Japan and its molecular analysis. Microbiol Immunol 48: 103-109.
59. Wade T, Booy R, Teare E L, Kroll S (1999) *Pasteurella multocida* meningitis in infancy—(a lick may be as bad as a bite). European Journal of Pediatrics 158:875-878.
60. Heym B, Jouve F, Lemoal M, Veil-Picard A, Lortat-Jacob A, et al. (2006) *Pasteurella multocida* infection of a total knee arthroplasty after a "dog lick". Knee Surg Sports Traumatol Arthrosc 14: 993-997.
61. Kikuchi K, Karasawa T, Piao C, Itoda I, Hidai H, et al. (2004) Molecular confirmation of transmission route of *Staphylococcus intermedius* in mastoid cavity infection from dog saliva. J Infect Chemother 10: 46-48.
62. Kempker R, Mangalat D, Kongphet-Tran T, Eaton M (2009) Beware of the pet dog: a case of *Staphylococcus intermedius* infection. American Journal of the Medical Sciences 338: 425-427.
63. Godey B, Morandi X, Bourdiniere J, Heurtin C (1999) Beware of dogs licking ears. Lancet 354: 1267-1268.
64. Chang K, Siu L K, Chen Y H, Lu P L, Chen T C, et al. (2007) Fatal *Pasteurella multocida* septicemia and necrotizing fasciitis related with wound licked by a domestic dog. Scand J Infect Dis 39: 167-170.
65. Erdman S E, Poutahidis T (2014) Probiotic 'glow of health': it's more than skin deep. Benef Microbes 5: 109-119.
66. Sakaguchi S, Yamaguchi T, Nomura T, Ono M (2008) Regulatory T cells and immune tolerance. Cell 133: 775-787.
67. Belkaid Y, Rouse B T (2005) Natural regulatory T cells in infectious disease. Nat Immunol 6: 353-360.
68. Romero T, Nagasawa M, Mogi K, Hasegawa T, Kikusui T (2014) Oxytocin promotes social bonding in dogs. Proc Natl Acad Sci USA 111: 9085-9090.
69. Guastella A J, Hickie I B (2016) Oxytocin Treatment, Circuitry, and Autism: A Critical Review of the Literature Placing Oxytocin Into the Autism Context. Biol Psychiatry 79: 234-242.
70. Lefevre A, Sirigu A (2016) The two fold role of oxytocin in social developmental disorders: A cause and a remedy? Neurosci Biobehav Rev 63: 168-176.
71. Ibrahim Y M K, S. M.; Levkovich, T.; Springer, A.; Mirabal, S.; Poutahidis, T.; Varian, B. J.; Lakritz, J. R.; Alm, E. J.; Erdman, S. E. Maternal Gut Microbes Control Offspring Sex and Survival. Journal of Probiotics and Health 2: 6.
72. Geenen V, Legros J J, Franchimont P, Baudrihaye M, Defresne M P, et al. (1986) The neuroendocrine thymus: coexistence of oxytocin and neurophysin in the human thymus. Science 232: 508-511.
73. Landgraf R, Neumann I D (2004) Vasopressin and oxytocin release within the brain: a dynamic concept of multiple and variable modes of neuropeptide communication. Front Neuroendocrinol 25: 150-176.
74. Wathes D C, Swann R W (1982) Is oxytocin an ovarian hormone? Nature 297: 225-227.
75. Fields P A, Eldridge R K, Fuchs A R, Roberts R F, Fields M J (1983) Human placental and bovine corpora luteal oxytocin. Endocrinology 112: 1544-1546.
76. Guldenaar S E, Pickering B T (1985) Immunocytochemical evidence for the presence of oxytocin in rat testis. Cell Tissue Res 240: 485-487.
77. S M O M, Stilling R M, Dinan T G, Cryan J F (2015) The microbiome and childhood diseases: Focus on brain-gut axis. Birth Defects Res C Embryo Today 105: 296-313.
78. Matelski L, Van de Water J (2016) Risk factors in autism: Thinking outside the brain. J Autoimmun 67: 1-7.
79. Elabd C, Cousin W, Upadhyayula P, Chen R Y, Chooljian M S, et al. (2014) Oxytocin is an age-specific circulating hormone that is necessary for muscle maintenance and regeneration. Nat Commun 5: 4082.
80. Varian B J; Poutahidis, T.; Lakritz, J. R.; Levkovich, T.; Kwok, C.; Teliousis, K.; Ibrahim, Y. M.; Mirabal, S.; Erdman, S. E. (2016) Beneficial bacteria inhibit cachexia Oncotarget.

81. Varian B J, Poutahidis T, Levkovich T, Ibrahim Y M, Lakritz J R, et al. (2014) Beneficial Bacteria Stimulate Youthful Thyroid Gland Activity. J Obes Weight Loss Ther 4.
82. Troy E B, Kasper D L (2010) Beneficial effects of *Bacteroides fragilis* polysaccharides on the immune system. Front Biosci (Landmark Ed) 15: 25-34.
83. Erdman S E, Rao V P, Olipitz W, Taylor C L, Jackson E A, et al. (2010) Unifying roles for regulatory T cells and inflammation in cancer. Int J Cancer 126: 1651-1665.
84. Erdman S E (2016) Gut microbiota: Microbes offer engineering strategies to combat cancer. Nat Rev Gastroenterol Hepatol.
85. Adams C A (2010) The probiotic paradox: live and dead cells are biological response modifiers. Nutr Res Rev 23: 37-46.
86. Poutahidis T, Erdman S E (2016). Commensal bacteria modulate the tumor microenvironment. Cancer Letters.

Example 2

Example 2A

To probe the roles of a human breast and gut commensal microbe in physiology, the present inventor examined outbred stock CD-1 female mice. Females were selected to better match the human subject trial. Eight-week-old CD-1 mice were randomly subdivided into groups of ten mice per treatment (N=10 mice per group) and received in their drinking water probiotic *L. reuteri* ATCC-PTA-6475 continuously for four weeks until the end of the experiment at 12 weeks-of-age. At three weeks after the start of treatment, mice underwent the 0.2 mm skin wound procedure at six days before necropsy, an experimental duration comprised of three weeks of feeding bacteria before biopsy plus six days of wound monitoring after biopsy. Tissue collections were performed after $CO_2$ overdose and exsanguination. For complete blood counts of immune cells, whole blood was collected via cardiac puncture from unconscious mice. Blood plasma was processed immediately with a preservative and then frozen for future oxytocin and corticosterone analyses. Thymus weights were recorded upon necropsy. Tissues were collected for histology and immunohistochemistry.

Example 2B

To test whether oxytocin is required for wound healing benefits of oral therapy with gut microbes, the present inventor next examined oxytocin-wt [ot-wt] and oxytocin-knockout (ot-ko) B6; 129S-Oxttm1Wsy/J mice. Eight-week-old B6; 129S-Oxttm1Wsy/J mice were randomly subdivided into groups of eight-ten mice per treatment (N=8-10 mice per group) and received in their drinking water *L. reuteri* ATCC-PTA-6475 continuously until 12 weeks-of-age. Mice underwent the 0.2 mm skin wound procedure at six days before necropsy. Tissues were collected upon necropsy.

Example 2C

To test whether physiological effects are achievable using non-viable microbe lysates alone, C57BL/6 WT mice underwent the same assays as above. Eight week old C57BL/6 mice were randomly subdivided into groups of eight-ten mice per treatment and received in their drinking water for four weeks a postbiotic lysed *L. reuteri* ATCC-PTA-6475 continuously until 12 weeks-of-age. Mice underwent the 0.2 mm skin wound procedure at six days before necropsy, with an experimental duration comprised of three weeks of feeding bacteria before biopsy plus six days of wound repair prior to necropsy. Tissues were collected upon necropsy, as above.

Results

Oral Administration of *L. reuteri* Improves Wound Repair Capacity

It was previously shown in C57BL/6 mice that *L. reuteri* ATCC PTA 6475 in drinking water enhanced skin wound-healing capability in half the time required for matched control animals via up-regulation of the neuropeptide hormone oxytocin (Poutahidis et al., 2013a). The ability to heal flesh wounds rapidly is the hallmark of sustained good health and longevity. For this reason, the present inventor has applied host capacity to repair tissues after surgical wound infliction as a surrogate marker for overall fitness. In support of this, dietary *L. reuteri* supplementation in mouse models has also been shown to impart a wide array of phenotypes including improved maternal care, lowered risk for obesity, with multigenerational effects on behavior, infertility, and cancer risks (Table 1), supporting use of this prototype probiotic microbe in further studies.

Figures 7A, 7B:
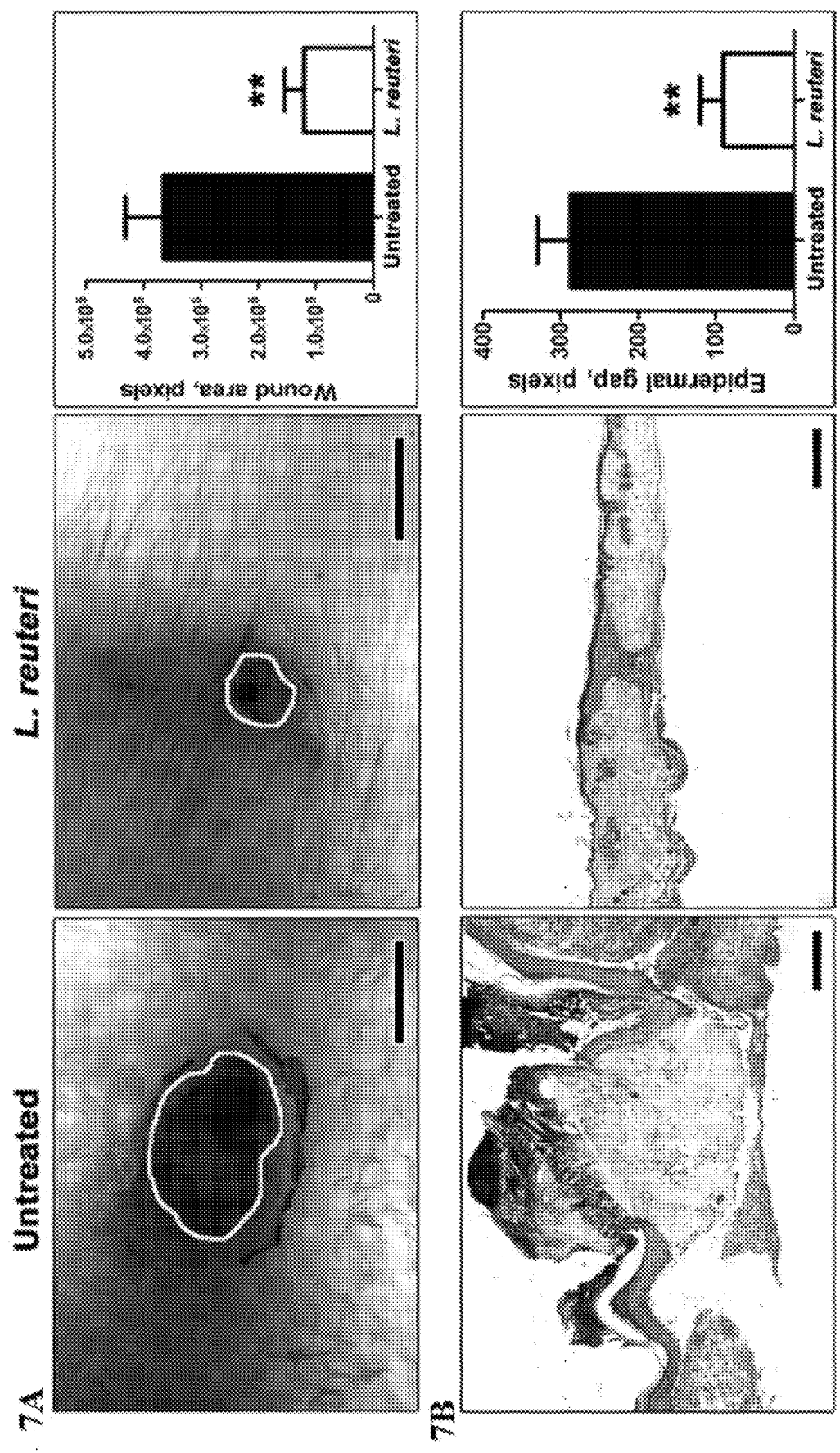
FIGS. 7A-7B demonstrate that *L. reuteri* accelerates the healing of skin wounds in mouse models.

In Example 2A, the present inventor employed a traditional skin biopsy assay in eleven-week-old outbred Swiss stock (CD-1) mice consuming *L. reuteri* to test wound healing capability as a surrogate marker for systemic resiliency and good health. Mice were drinking *L. reuteri* for three weeks prior to skin biopsy. In this case, outbred Swiss mice were selected to complement published studies in C57BL/6 mice and to overcome genetic biases imposed by inbred strains, thus broadening translational potential of the resulting data. The skin wound assay applied a standardized 2.0 millimeter full thickness excision of dorsal skin of mice, with the wound site subsequently examined microscopically at six days after biopsy. Six days was selected as most highly significant timing based upon earlier experiments showing the rate of wound healing during the first twelve days after biopsy (Poutahidis et al., 2013a). Using this approach, the present inventor found that consuming *L. reuteri* (N=10) speeds epithelial closure (p<0.005) when compared with control mice (N=10) drinking regular water (FIGS. 7A and 7B). The present inventor next tested whether human subjects were similarly susceptible to benefits of consuming probiotic *L. reuteri*.

Figure 8A:
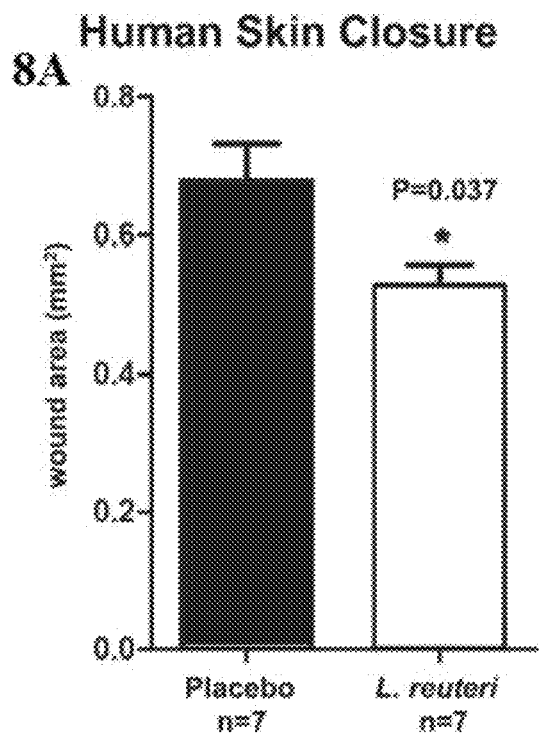
FIGS. 8A-8C demonstrates that dietary *L. reuteri* confers increased wound healing capacity in human subjects.
Figure 8B:
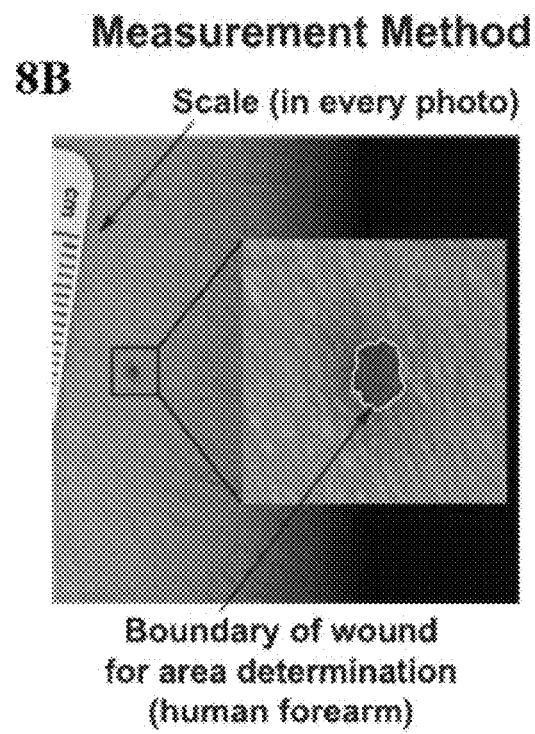
Figure 8C:
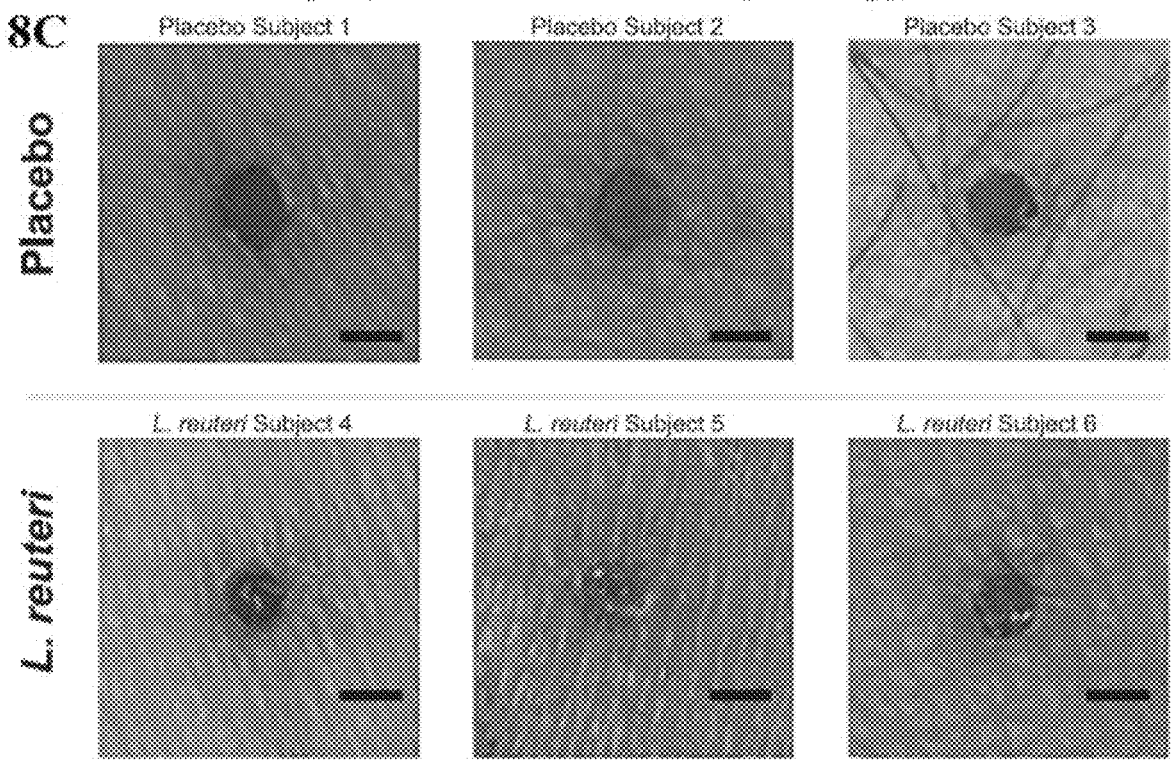

Building upon this microbe-centric wound repair paradigm, the present inventor tested in a small pilot study on human subjects whether daily consumption of probiotic *L. reuteri*, also proven therapeutic in human gastrointestinal diseases (Preidis and Versalovic, 2009), was sufficient to improve skin wound-healing, as was seen in mouse models. For this experiment, fourteen healthy female volunteer subjects in a double-blind placebo-controlled study consumed chewable *L. reuteri* DSM17938 supplements (BioGaia Protectis) or placebo 60 mg vitamin C twice daily for three weeks before undergoing a full-thickness biopsy of forearm skin at MIT's Clinical Research Center. Subjects had a mean age of 29 years (range, 19-42y) and included individuals with diverse ethnicity. Three days following biopsy, patients consuming *L. reuteri* had more rapid skin closure (N=7 per treatment; p=0.037) compared with placebo (FIG. 8A). Standardized macroscopic photography (FIG. 8B) revealed smaller wound sizes and more advanced healing in individuals after treatment with *L. reuteri* (N=7) when compared with placebo-treated controls (N=7) (FIG. 8C).

Drinking of *L. reuteri* Leads to Higher Blood Levels of Oxytocin in Mice

Figure 9A:
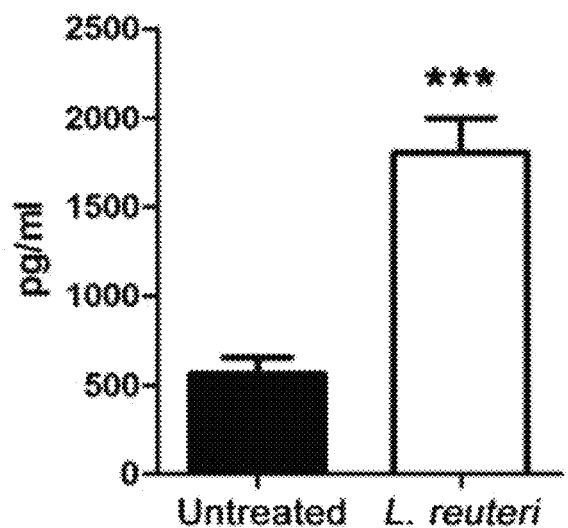
FIGS. 9A-9D demonstrate that *L. reuteri* affects hormone levels and thymus size of Swiss mice. *L. reuteri* consumption leads to statistically significant changes, including increased blood levels of oxytocin (Untreated N=10, *L. reuteri* N=10) (FIG. 9A), decreased levels of circulating corticosterone (N=10 per group) (FIG. 9B), increased thymus weight (FIG. 9C), (N=10 per group) and lower circulating neutrophil counts (N=10 per group) (FIG. 9D). Numbers on the y-axis of bar graphs correspond to the mean±SEM of the parameter assessed;  p<0.001, *p<0.0001.

Oxytocin is pivotal in normal mammalian wound healing processes (Gavrilenko et al., 2003; Gouin et al., 2010; Poutahidis et al., 2013a; Vitalo et al., 2009), and may serve to bridge bacteria-triggered behaviors and stress responses with physical fitness. Thus, the present inventor tested oxytocin levels in blood plasma of Swiss mice in Example 2A, and found significant systemic elevation of this hormone in animals drinking *L. reuteri* daily (N=10) when compared with matched untreated controls (N=10) (FIG. 9A). The microbe-enhanced skin wound repair capacity in mice was found to rely upon oxytocin when tested in a second experiment using oxytocin-knockout (ot-ko) B6; 129S-Oxttm1Wsy/J mice. By comparing wound sizes (measured microscopically in pixels) it was found that ot-wt mice consuming *L reuteri* (N=8) at 6 days-post-biopsy had smaller wounds (68464±13997 pixels; mean±SE) relative to those seen in ot-ko mice consuming *L. reuteri* (N=8) (225937±27539 pixels, p=0.0003), matching earlier findings of oxytocin-dependency in mouse models (Poutahidis et al., 2013a).

TABLE 1

| Effect | Human | Mouse | Rat |
| --- | --- | --- | --- |
| IBD/chronic colitis | | Hemarajata et al. (2013), Gao et al. (2015), Thomas et al. (2016) | Liu et al. (2010) |
| Diarrhea (various causes) | | Eaton et al. (2011), Preidis et al. (2012) | |
| *H. pylori* Gastritis | Francavilla et al. (2014) | | |
| Osteoporosis | | McCabe et al. (2013), Britton et al. (2014), Zhang et al. (2015a, b), Collins et al., 2016; | |
| Obesity | | Poutahidis et al. (2013a, b, 2014), Varian et al. (2014) | |
| Social behavior | | Ibrahim et al. (2014), Buffington et al. (2016) | |
| Muscle Wasting | | Varian et al. (2016a,b) | |
| Skin health | | Levkovich et al. (2013), Erdman and Poutahidis (2014) | |
| Hair growth | | Levkovich et al. (2013) | |
| Testicular atrophy | | Poutahidis et al. (2014) | |
| Fertility | | Ibrahim et al. (2014), Poutahidis et al. (2014, 2015) | |
| Thyroid atrophy | | Varian et al. (2014) | |
| Thymic atrophy | | Varian et al. (2016a ,b) | |
| Wound healing | | Poutahidis et al. (2013a, b), Erdman and Poutahidis (2014) | |
| Multi-generational phenotypes | | Poutahidis et al. (2015), Buffington et al. (2016) | |
| Cancer | | Lakritz et al. (2014), Poutahidis et al. (2015), Varian et al. (2016a, b) | |
| Longevity | | Ibrahim et al. (2014), Varian et al. (2016a, b) | |

Positive effects of *L. reuteri* ATCC PTA 6475 on pathological conditions studied in vivo.

Oral *L. reuteri* Down-Regulates Blood Levels of Stress Hormone Corticosterone

Figure 9B:
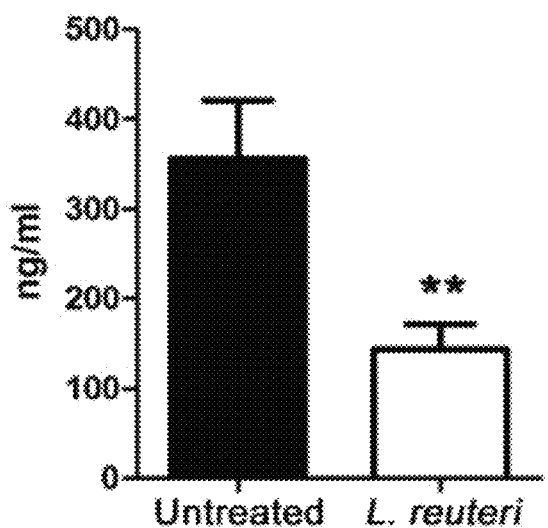

An inverse relationship exists, in general, between systemic levels of oxytocin and the stress-related hormones cortisol and corticosterone (Burkett et al., 2016; Cohen et al., 2010; Smith et al., 2016a; Stanic et al., 2016; Vilela et al., 2013; Wang et al., 2012). Finding that oral *L. reuteri* therapy increased circulating levels of oxytocin in an animal model, the present inventor theorized that *L. reuteri* associated with better maternal care and nursing behavior may also down-regulate stress levels in host animals. Indeed, it was previously shown that favorable mood rises after consuming other *Lactobacillus* sps (Bravo et al., 2011). To examine this possibility further, the present inventor examined levels of the stress biomarker hormone corticosterone in mice (N=10 per group), and found lower stress hormone levels in Swiss mice drinking *L. reuteri* (p<0.01) (FIG. 9B). Increased corticosterone levels in rodent models of stress have been linked with a decrease of thymus gland weight (Listowska et al., 2015; Monteiro et al., 2015; Rosa et al., 2014; Zivkovic et al., 2005), and premature thymic involution, leading to host animal immune dysregulation.

Thymus Gland Size is Increased after Oral Dosing with *L. reuteri*

Figure 9C:
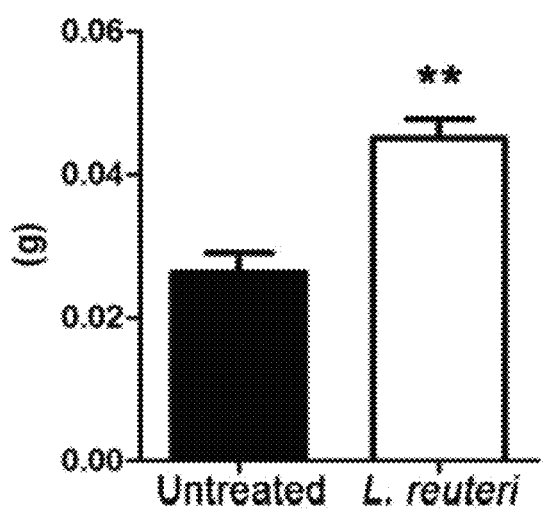

Accumulated data from animal models and human subjects shows that premature thymic involution results in T-lymphocyte deficiency and produces a wide array of detrimental outcomes linked with systemic immunodeficiency (Taub and Longo, 2005; Ventevogel and Sempowski, 2013). Knowing that oxytocin has been implicated in improved immune health (Barnard et al., 2008), and that feeding of *L. reuteri* ATCC PTA 6475 increases thymus gland size in mice (Varian et al., 2016a), the present inventor examined postmortem thymus gland weights in the same Swiss mice consuming *L. reuteri* in drinking water. We found that the thymus gland weight was significantly increased (p<0.01) in the probiotic-treated mice (N=10) when compared to age-matched control animals (N=10) (FIG. 9C).

Circulating Neutrophil Counts are Decreased in Mice Consuming *L. reuteri*

Figure 9D:
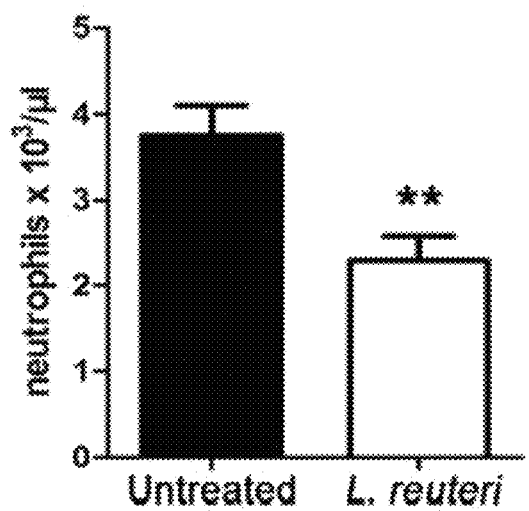

In previous studies it was shown that oral *L. reuteri* treatment also is associated with a subclinical reduction of circulating neutrophils (Varian et al., 2016a; Varian et al., 2016b). Therefore, the present inventor reasoned that blood neutrophil counts are a candidate biomarker for influences of *L. reuteri* on systemic immune status. The present inventor tested this possibility in the present experiment using outbred Swiss mice (N=10 per group) and found that probiotic treatment reduced (p<0.01) the numbers of circulating (blood) neutrophils (FIG. 9D). Lowered neutrophil counts in mice was found to rely upon oxytocin when tested in a second experiment using oxytocin-knockout (ot-ko) B6; 129S-Oxttm1Wsy/J mice. By comparing neutrophil counts (measured as cell/ul in a CBC) it was found that ot-wt mice consuming *L reuteri* (N=8) at 6 days-post-biopsy had fewer (p<0.01) neutrophils (1.586±0.122) compared to those seen in ot-ko mice drinking *L. reuteri* (N=8) (3.252±0.289), matching earlier findings of oxytocin-dependency in mouse models (Poutahidis et al., 2013a).

Figure 10A:
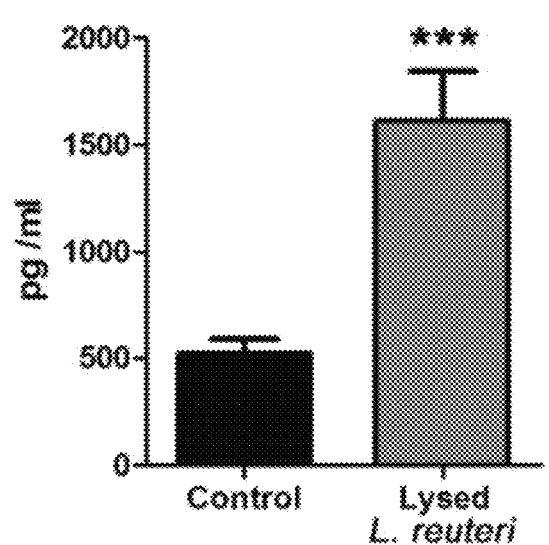
FIGS. 10A-10D demonstrate that lysed *L. reuteri* products alter blood hormone levels and thymus gland size of C57BL/6 mince. Edible sterile, lysed *L. reuteri* was sufficient to upregulate blood levels of oxytocin (Untreated N=9; Lysed *L. reuteri* N=10) (FIG. 10A), downregulate blood levels of corticosterone (Control N=9; Lysed *L. reuteri* N=10) (FIG. 10B), bestow increased thymus weight (N=8-10 per treatment group) at statistically significant levels (FIG. 10C), and lower circulating neutrophil counts (Control N=9; Lysed *L. reuteri* N=10) (FIG. 10D). Numbers on the y-axis of bar graphs correspond to the mean±SEM of the parameter assessed;
***p<0.0001.
Figure 10B:
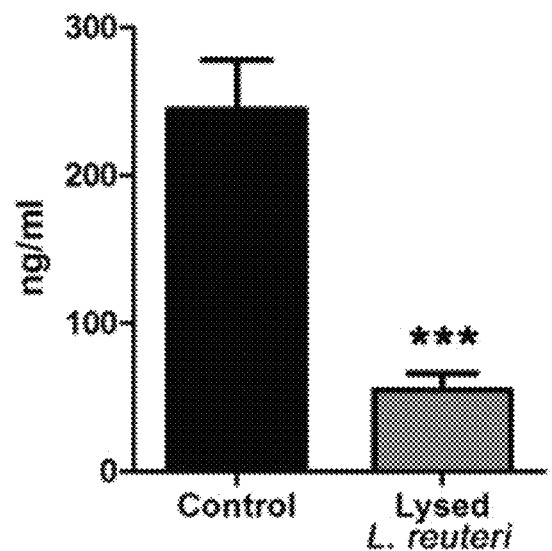
Figure 10C:
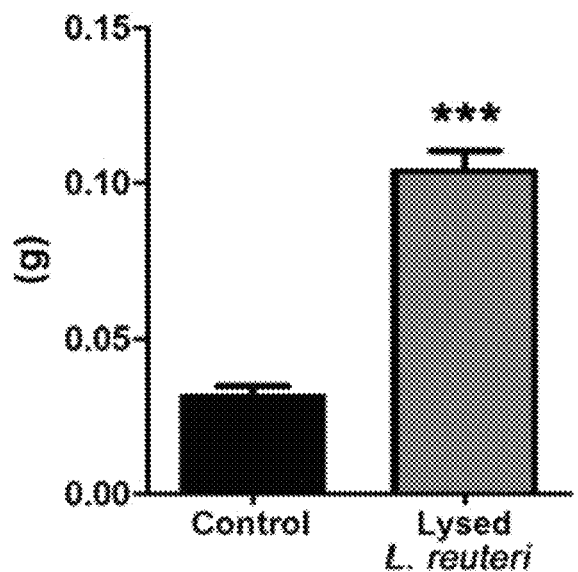
Figure 10D:
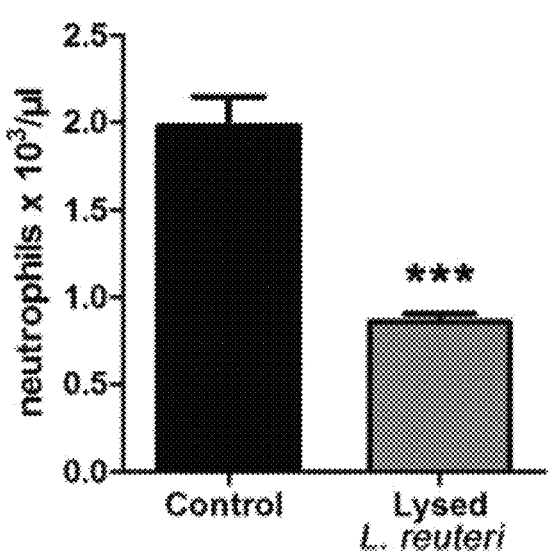

Killed Sterile *L. reuteri* Lysate is Sufficient to Elevate Plasma Oxytocin Levels Recognizing that infection with *L. reuteri* leads to higher levels of oxytocin in mice (Buffington et al., 2016; Poutahidis et al., 2013a; Varian et al., 2016b), raises many questions about probiotic organism viability requirements and interactions with other host microbes. It was earlier shown that oxytocin-mediated slenderizing effects of *L. reuteri* were achievable when using a lysed sterile *L. reuteri* preparation alone (Varian et al., 2016b). The present inventor next tested in Example 2C whether oral administration of *L. reuteri* ATCC 6475 sterile lysate alone was sufficient to raise endogenous oxytocin levels in mouse models. A soluble extract of sterile microbial lysate was prepared using sonication with repeated centrifugation, resulting in a sterile soluble fraction delivered to mice in their drinking water. Plasma oxytocin levels were then examined in twelve-week-old wild type C57BL/6 mice consuming the equivalent of $3.5 \times 10^5$ L. reuteri ATCC 6475 organisms per day added in the form of lysate to their drinking water. We found that mice drinking sterile lysate (N=10) had higher circulating levels of oxytocin measurable in blood plasma by comparison with control mice (N=9) (p<0.001) (FIG. 10A). We also found that mice consuming lysate had lower blood levels of stress hormone corticosterone (Lysed L. reuteri N=10; Control N=9) (FIG. 10B), larger thymus glands (FIG. 10C) (N=8-10 mice per group) and fewer circulating neutrophils (Lysed LR N=10; Control N=9) (FIG. 10D) when compared with untreated controls getting regular water. These data matched earlier findings using viable L. reuteri.

Figure 11A:
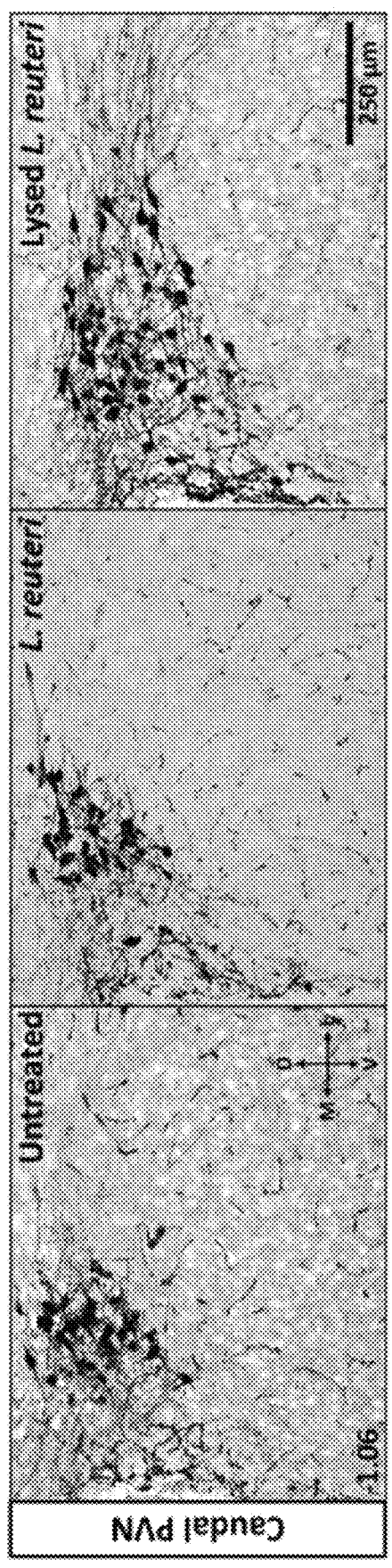
FIGS. 11A-11B demonstrate that mice treated with lysed *L. reuteri* had more oxytocin-immunoreacitve (OT-ir) neurons in the caudal PVN.
Figure 11B:
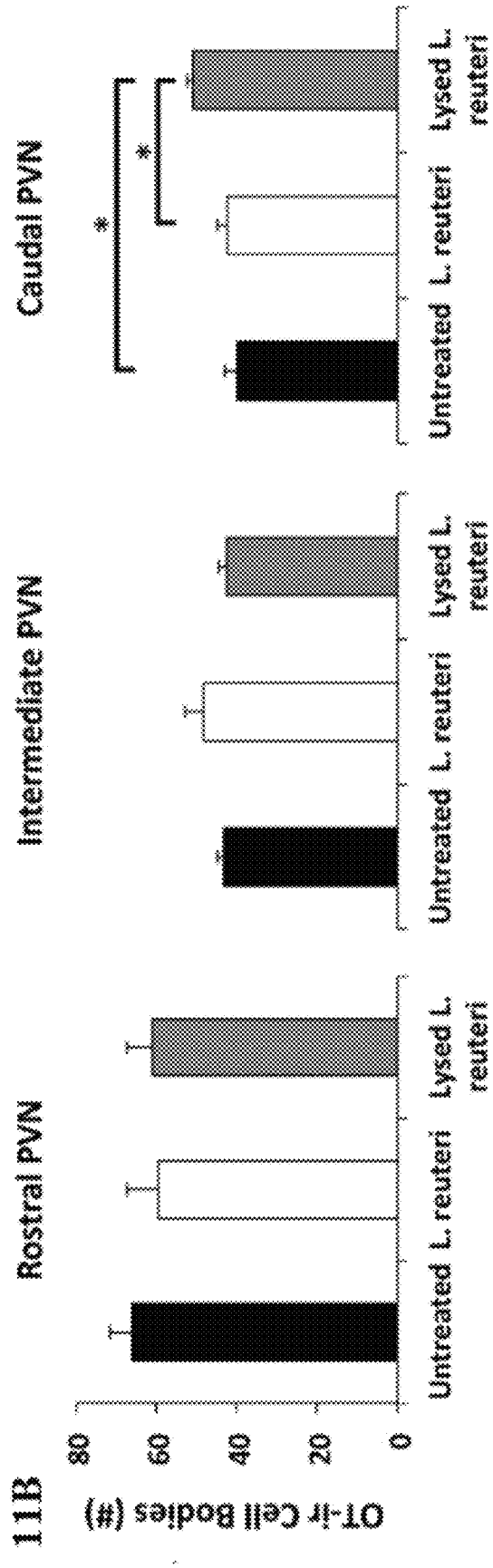

Sterile L. reuteri Lysate Increases Oxytocin-Positive Cell Counts in the Paraventricular Nucleus [PVN] of Hypothalamus To determine whether microbe treatment had an effect on the number of oxytocin-ir neurons in the PVN, mice treated with lysed L. reuteri, live L. reuteri, and untreated controls were sacrificed and their brains were immunolabeled for oxytocin-associated neurophysin (FIG. 11A). Lysed L. reuteri treated mice had more oxytocin-ir neurons in the caudal PVN compared to live L. reuteri and normal drinking water (untreated) mice (treatment effect: $F_{(2,22)}=7.61$; p=0.003; FIG. 11B). However, no microbe treatment effects were observed on the number of oxytocin-ir neurons in the rostral ($F_{(2,22)}=0.25$; p=0.78) or intermediate portions of the PVN ($F_{(2,22)}=1.26$; p=0.30; FIG. 11B).

To determine the source of systemic oxytocin elevations, and also whether lysed L. reuteri postbiotic treatment had an effect on the number of oxytocin-positive neurons in the PVN, mice treated with microbe lysate (N=10) and controls (N=9) were euthanized and their brains were immunolabeled for oxytocin (FIG. 11A) using previously published techniques (Ben-Barak et al., 1985; Franklin, 2008). Microbe lysate-treated mice had more oxytocin-immunoreactive neurons in the caudal PVN compared to those normal drinking water (control) mice ($F_{(2,22)}=7.61$; p=0.003). However, no microbe treatment effects were observed on the number of oxytocin-immunoreactive neurons in the rostral ($F_{(2,22)}=0.25$; p=0.78) or intermediate portions of the PVN ($F_{(2,22)}=1.26$; p=0.30; FIG. 5B). This showed that microbe lysate consumption stimulated oxytocin-producing cells in the hypothalamus coinciding with increased levels of plasma oxytocin in mice.

Ingestion of Microbe Lysate Conveys Increased Wound Healing Capacity

Figure 12A:
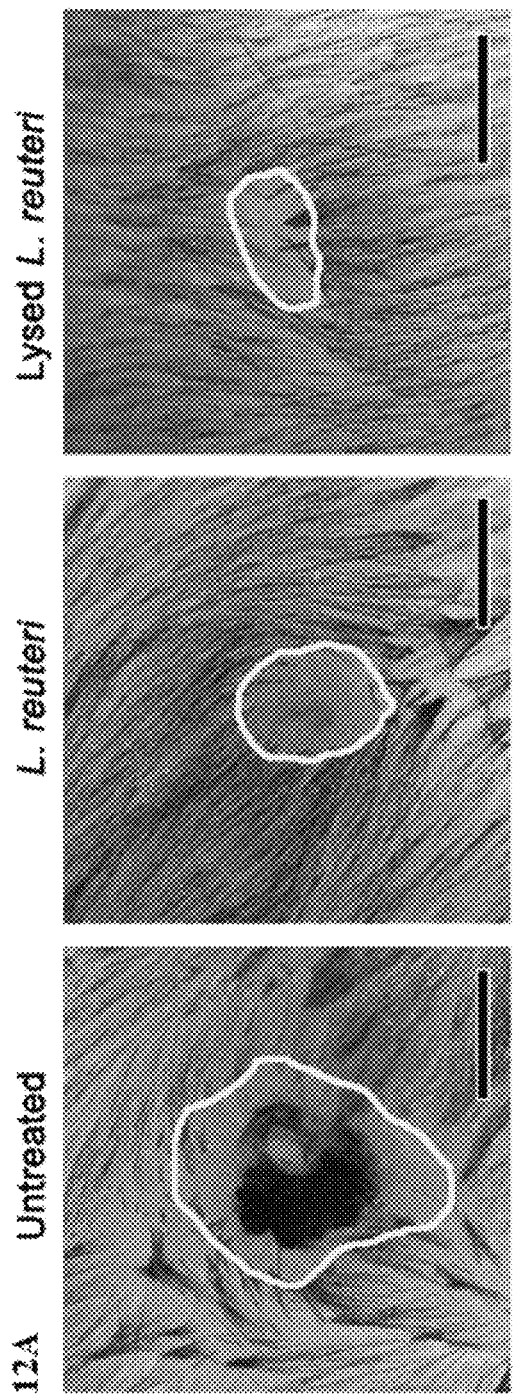
FIGS. 12A-12C demonstrate that *L. reuteri* viability is not required for the observed skin and wound healing benefits.
Figure 12B:
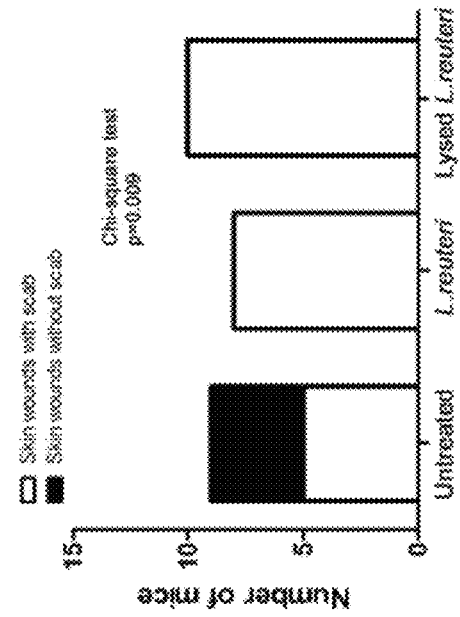
Figure 12C:
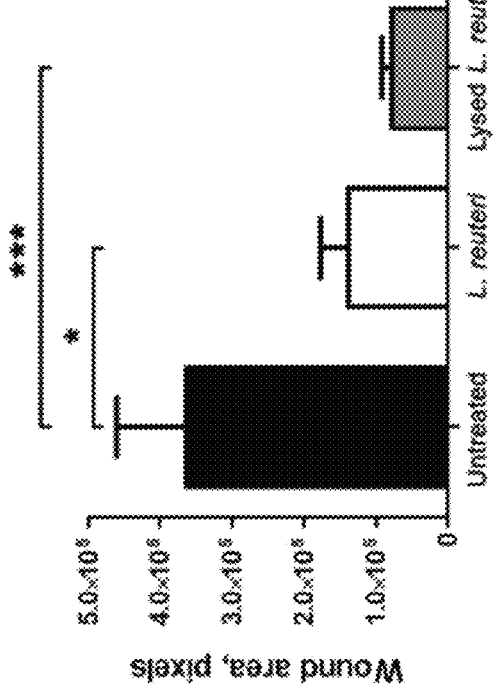
Figure 13:
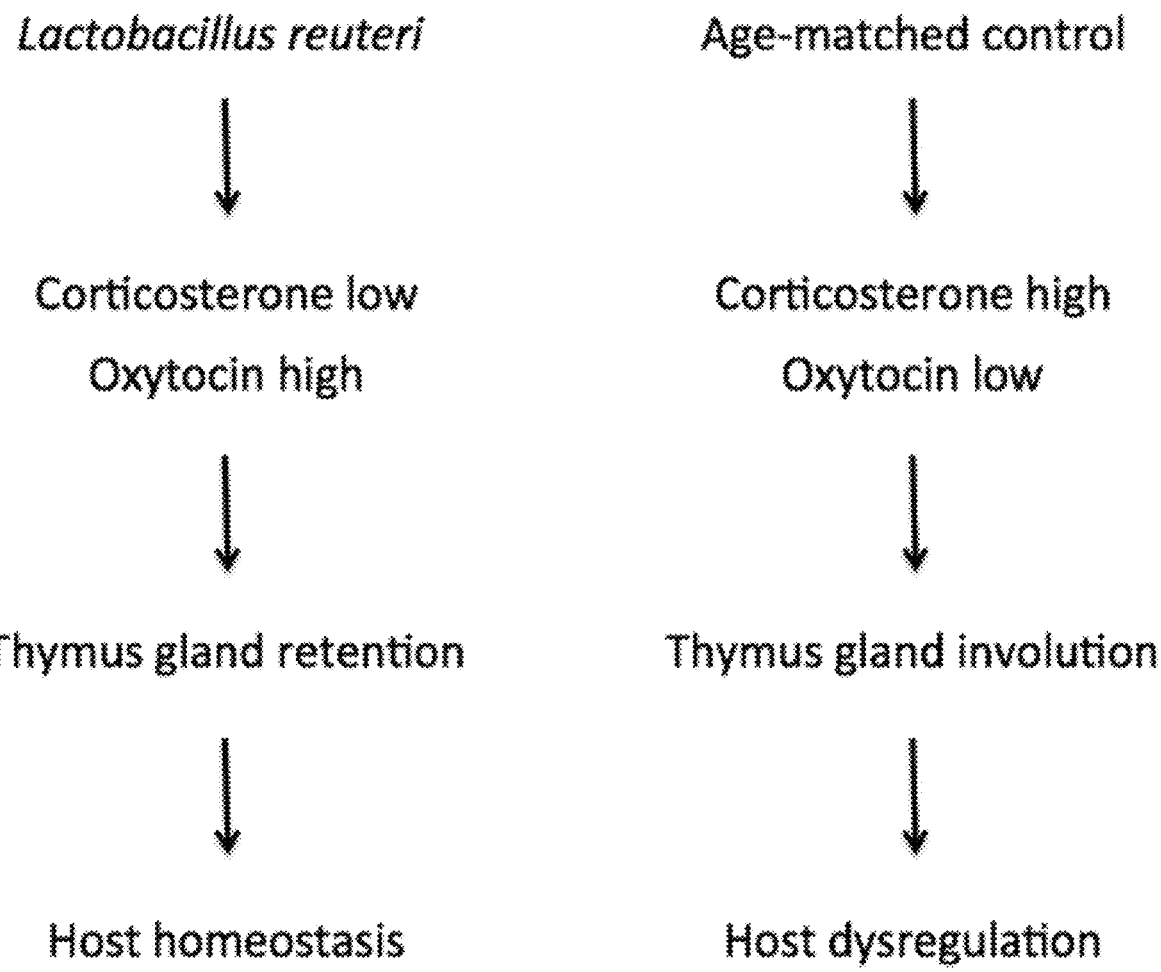
FIG. 13 depicts that *L. reuteri* modulates host animal stress hormones and immune homeostasis. Consumption of *L. reuteri* was sufficient to up-regulate oxytocin and down-regulate corticosterone levels, resulting in larger thymus gland size and immune homeostasis with improved host wound repair capacity.

Finally, to test the efficacy of lysed L. reuteri upon epithelial wound healing in the C57BL/6 mouse model, mice receiving for four weeks either live (N=8) or lysed (N=10) L. reuteri ATCC 6475 underwent the skin wound assay and were compared with untreated mice serving as controls (N=9). Examining wound areas at the sixth day after skin excision, the present inventor found that both viable and lysed L. reuteri treatments led to significant acceleration of wound closure (FIGS. 12A and 12B) compared to untreated control mice. Faster wound healing rates of pro- or postbiotic-treated mice were also characterized by more frequent detachment of wound scabs at 6 days after experimental wound induction (FIG. 12C). In summary, these data led the present inventor to propose a host stress paradigm whereby microbiota and their products modulate stress hormone levels leading to immune modulation subsequently influencing homeostasis and wound healing processes throughout the body (FIG. 13).

Discussion

Here the present inventor provides evidence that postbiotic (non-viable) preparations of L. reuteri are sufficient to elevate blood levels of oxytocin and increase the number of oxytocin-positive cells in the PVN of mice. Microbe-triggered increases in blood and brain oxytocin were associated with improved wound healing capacity, lowered blood levels of stress hormone corticosterone, plus a larger thymus gland and fewer pro-inflammatory blood neutrophils in mice consuming L. reuteri. Microbe-induced oxytocin was necessary for more proficient wound repair. Human subject findings linking L. reuteri consumption with improved wound repair capacity reinforce translational potential of the findings in mice. Finally, sterile preparations of L. reuteri lysate were sufficient for achieving health benefits in mice, suggesting that these phenomena are triggered by a bacterial component, rather than by activities or interactions of live bacteria.

The present inventor found that mice treated with L. reuteri lysate had more oxytocin immunoreactive neurons in the caudal PVN. Oxytocin produced in the PVN can be released in the brain via axonal projections, somato-dendritic release or volume transmission (Knobloch et al., 2012; Landgraf and Neumann, 2004; Ludwig and Leng, 2006) and act as a neuromodulator. Alternatively, oxytocin can be released in the periphery via axonal projections to the posterior pituitary, where it functions as hormone. Oxytocin exerts its actions through binding to the oxytocin receptor, which is widely expressed in the brain and periphery (Gimpl and Fahrenholz, 2001; Jard et al., 1987; Smith et al., 2016a; Smith et al., 2016b). This allows oxytocin to modulate a large array of physiological processes, including immune-related processes. Oxytocin-positive PVN neurons can be parvocellular or magnocellular, and both phenotypes have been observed in the caudal PVN (Eliava et al., 2016; Herman et al., 2002a; Herman et al., 2002b). Parvocellular oxytocin-positive neurons extend axonal projections throughout the brain, whereas magnocellular oxytocin-positive neurons project primarily to the periphery, but also possess collateral branches projecting to forebrain regions (Knobloch et al., 2012). This may indicate that increased oxytocin production in L. reuteri extract-treated mice could contribute to improving the observed wound healing capacity via both central and peripheral pathways.

Although speculative, an increase in oxytocin-positive PVN neurons in L. reuteri lysate-treated mice could reflect oxytocin-negative PVN neurons that are recruited to express oxytocin in response to a higher demand for oxytocin synthesis. This higher demand for oxytocin synthesis is likely a direct result of increased levels of plasma oxytocin, as was observed in L. reuteri-treated mice. It should be noted that, in addition to the PVN, oxytocin synthesized in the supraoptic nucleus (SON) might also have been affected by microbe treatment. Unfortunately, oxytocin immunoreactive cells in the SON were too dense to distinguish individually in order to quantify cell numbers. Thus, the present inventor cannot exclude the possibility that oxytocin neurons in the SON, in addition to the PVN, contributed to the increase in plasma oxytocin levels observed in mice treated with L. reuteri. This could be addressed in future studies by quantifying oxytocin mRNA expression in both the PVN and SON, which may provide additional information regarding the need for higher oxytocin synthesis in microbe lysate-treated mice.

The observation that lysed *L. reuteri* ATCC 6475 cells were comparable with their viable counterparts in conferring typical *L. reuteri*-induced health benefits in mice is important. Indeed, the ingestion of the killed form of the probiotic served to up-regulate oxytocin, down-regulate corticosterone, increase thymic mass, decrease circulating neutrophils, and accelerate skin wound healing. These findings are in accordance with the results of another recent study using a different *L. reuteri* isolated from pet dogs (Varian et al., 2016b). In that study, lysed extract of canine *L. reuteri* strain 2546 counteracted obesity and decreased blood neutrophils of mice, recapitulating earlier findings for viable *L. reuteri* ATCC PTA 6475 (Poutahidis et al., 2013b; Varian et al., 2016a; Varian et al., 2016b; Varian et al., 2014). Using oxytocin-deficient mice in that earlier study showed that the slenderizing effects of *L. reuteri* 2546 lysate depended on the hormone oxytocin (Varian et al., 2016b).

Specific bacterial components with health-promoting effects are termed 'postbiotics' and hold promise as a more precise, controlled and effective therapeutic approach compared to live probiotic cell consumption (Adams, 2010; Caselli et al., 2011; Kataria et al., 2009; Ruiz et al., 2014; Sanchez et al., 2010). The retaining of beneficial health effects and immunomodulatory properties has been described for many different postbiotic forms of *Lactobacillus* spp and other beneficial bacteria (Adams, 2010; Caselli et al., 2011; Kataria et al., 2009; Ruiz et al., 2014; Sanchez et al., 2010). Based on accumulated studies the increased value of using non-viable bacterial cells is now emerging (Adams, 2010; Kataria et al., 2009). Killed forms are considered safer than live bacteria for many reasons (Adams, 2010; Kataria et al., 2009; Ruiz et al., 2014). The identification of the biologically-active ingredients of killed bacteria is considered as a step forward in microbe-based research.

Postbiotic bacterial components with beneficial properties are enticing but remain largely uncharacterized (Adams, 2010; Caselli et al., 2011; Kataria et al., 2009; Ruiz et al., 2014; Sanchez et al., 2010). In humans, spray-dried non-viable cells of *L. reuteri* DSMZ17648 were potent enough to decrease *Helicobacter pylori* load in the stomach (Mehling and Busjahn, 2013). In addition, the capsular polysaccharide A of *Bacteroides fragilis* has been shown to have desirable immunomodulatory effects in intestinal and neuronal tissue (Surana and Kasper, 2012). Along the same lines, bacterial DNA, exopolysaccharides, bacteriocins, lipoteichoic acids and other microbial cell wall components possess promising postbiotic attributes (Adams, 2010; Caselli et al., 2011; Kataria et al., 2009; Ruiz et al., 2014; Sanchez et al., 2010; Surana and Kasper, 2012). Thus far postbiotic compounds identified for *L. reuteri* include histamine and the bifunctional dihydrofolate synthase/folylpolyglutamate synthase type 2 (folC2)-mediated folate metabolism products essential for anti-inflammatory properties (Gao et al., 2015; Thomas et al., 2016). Taken together, this suggests that *L. reuteri* possesses powerful bioactive postbiotic molecules that are worthy of further exploration and testing for pharmaceutical applications.

In the present study, lysed *L. reuteri* ATCC 6475 was not heat-treated. In other studies, heat-killed non-viable forms of *L. reuteri* GMNL-263 were potent enough to prevent weight gain in a diet-induced obesity rat model (Hsieh et al., 2016). In high-fat diet fed hamsters, the same heat-treated material reduced liver fibrosis, blood LDL-cholesterol and plasma malondialdehyde and myocardial cell apoptosis (Ting et al., 2015a; Ting et al., 2015b). A heat-killed *L. reuteri* ATCC 23272 also reduced pro-inflammatory cytokines, but was less potent than viable forms in reducing eosinophil influx and airway damage (Forsythe et al., 2007); however, killed bacteria were able to reduce visceral pain (Kamiya et al., 2006). Importantly, Buffington, et al (2016) found that heat-killed *L. reuteri* ATCC 6475 failed to up-regulate oxytocin without behavioral benefits in mice (Buffington et al., 2016). This aspect remains to be investigated further, but indirectly points to a biologically active microbial protein in modulating host oxytocin levels in the present studies.

An interesting aspect of edible bacteria-derived compounds is their multi-dimensional beneficial activities. Microbe-based therapies may promote overall health by awakening complex and multi-dimensional systematic pathways for good health that otherwise remain latent due to modernized urban life-style (Erdman and Poutahidis, 2010; Rook, 2013; Walter et al., 2011). Preliminary evidence from the present and prior studies suggests that *L. reuteri* activates diverse homeostatic pathways at the whole organism level (Erdman and Poutahidis, 2014; Ibrahim, 2014; Lakritz et al., 2014; Levkovich et al., 2013; Poutahidis et al., 2013a; Poutahidis et al., 2013b; Poutahidis et al., 2014; Poutahidis et al., 2015; Varian et al., 2016a; Varian et al., 2016b; Varian et al., 2014). These involve inter-related gut, immune, endocrine, and brain functions that confer longevity and counteract senility-associated imbalances of host inflammatory responses (Erdman and Poutahidis, 2014; Ibrahim, 2014; Lakritz et al., 2014; Levkovich et al., 2013; Poutahidis et al., 2013a; Poutahidis et al., 2013b; Poutahidis et al., 2014; Poutahidis et al., 2015; Varian et al., 2016a; Varian et al., 2016b; Varian et al., 2014). In short, these microbes restore whole body homeostasis.

Along these lines, testing the effects of bacterial products on the thymus gland, an elementary immune system organ, is very informative. Firstly, because thymus is profoundly affected by normal aging progression (Taub and Longo, 2005). Secondly, thymus gland function is clearly influenced by neuroendocrine signaling networks. Finally, there is extensive evidence in both animal models and human subjects that premature thymic involution results in T-lymphocyte deficiency and produces a wide array of detrimental outcomes linked with systemic immunodeficiency (Taub and Longo, 2005; Ventevogel and Sempowski, 2013). In the light of these facts, the finding that mice consuming lysed *L. reuteri* extract have a significantly larger thymus gland compared to their age-matched controls may be particularly important. The youthfully-sized thymus after postbiotic consumption coincided with increased oxytocin levels in CNS and blood and decreased circulating corticosterone levels.

Connections between oxytocin and normal thymus function are indeed well-documented. Oxytocin has been shown to be essential for thymic lymphocyte differentiation and selection (Hansenne et al., 2005). Furthermore, the autoimmune regulator gene/protein (Aire)—important for natural T regulatory ($T_{res}$) cell differentiation in the thymus gland (Nomura and Sakaguchi, 2007)—is induced by oxytocin in thymic epithelial cells (Hansenne et al., 2009). Oxytocin cross-talk with immune system cells happens in part via membrane oxytocin receptors that promote peripheral mononuclear cell proliferation and suppress pro-inflammatory cytokines (Wang et al., 2015). Based on both preclinical models and human studies, exogenous oxytocin treatment emerges as a novel therapy for uncontrolled inflammation and immune-mediated tissue damage (Al-Amran and Shahkolahi, 2013; Biyikli et al., 2006; Clodi et al., 2008; Iseri et al., 2005a; Petersson et al., 2001; Wang et al., 2015). Specific mechanisms in the present model, whether immune or neuronal in origin, remain to be determined.

In the present mouse model studies, live *L. reuteri* organism consumption leads to increased levels of oxytocin coincident with decreased levels of the stress-related hormone corticosterone. The present study also shows that this inverse correlation of oxytocin and corticosterone emerges in mice consuming lysed *L. reuteri*. This finding is in line with the known role of oxytocin in improving social and non-social behaviors, and dampening anxiety, stress and depression (Baribeau and Anagnostou, 2015; Carter, 2014; Feldman et al., 2016). It is also consistent with previous reports describing the oxytocin-corticosterone interplay in rodent models of both social (Burkett et al., 2016; Wang et al., 2012) and non-social-related stress (Cohen et al., 2010; Smith et al., 2016a; Stanic et al., 2016; Vilela et al., 2013). It will be interesting to investigate roles for *L. reuteri* in stress-induced corticosterone levels and animal behaviors.

Interestingly, increased corticosterone levels in rodent models of stress have been shown to correlate with a decrease of thymus gland weight (Listowska et al., 2015; Monteiro et al., 2015; Rosa et al., 2014; Zivkovic et al., 2005), although some studies suggest that this effect depends on the type of stressor and strain of mouse used (Cruz et al., 2012; Savignac et al., 2011). By contrast, stimulation of social behavior or improving sense of well-being by enrichment of caging decreased corticosterone levels while counteracting thymus shrinkage in both mice and rats (Abou-Ismail and Mahboub, 2011; Seetharaman et al., 2016; Van Loo et al., 2004). A study in genetically engineered mice has provided direct evidence linking thymus gland size and function with corticosterone (Youn et al., 2011). Specifically, Youn et al (2011) have used mice that were deficient in Bag3, a multifunctional molecule involved in cell survival, migration, chaperone regulation, and cellular protein metabolism. This mouse model has highly elevated levels of corticosterone due to adrenal gland zona *reticularis* hyperplasia co-existing with severe thymus gland atrophy. Remarkably, the premature thymic involution in this model has been shown to be due to the increased production of adrenal gland corticosterone and not due to a direct effect of Bag3 depletion in the thymus or an impaired CRH and ACTH hypothalamic-pituitary gland negative feedback signaling (Youn et al., 2011).

In previous research (Poutahidis et al., 2013a; Varian et al., 2016a; Varian et al., 2016b) and the present study we find circulating neutrophils offer an important immune cell target of the gut-immune-endocrine interactive axis that is activated by *L. reuteri* consumption. Presently we show that drinking nonviable *L. reuteri* cells is as potent as drinking live probiotics in down-regulating circulating neutrophils. Previously we have ascribed this down-regulation to potency of regulatory T cells, the peripheral induction of which is highly upregulated after *L. reuteri* consumption (Erdman and Poutahidis, 2014; Lakritz et al., 2014; Poutahidis et al., 2013a; Varian et al., 2016a). Our accumulated data (Poutahidis et al., 2013a; Varian et al., 2016a; Varian et al., 2016b) together with present findings, however, suggest that hormones such as oxytocin and corticosterone may also contribute directly to this immune-mediated phenomenon. Oxytocin's reported actions upon inflammatory processes appear to involve neutrophil homeostasis as one of its most characteristic actions (Al-Amran and Shahkolahi, 2013; Biyikli et al., 2006; Clodi et al., 2008; Iseri et al., 2005a; Petersson et al., 2001; Wang et al., 2015). Indeed, the present inventor has found that otherwise untreated oxytocin-deficient mice, which are clinically healthy and show no evidence of inflammatory disease, have a significant subclinical elevation of blood neutrophils compared to their wild-type controls [data not shown]. Lower corticosterone levels after *L. reuteri* treatment may also contribute to the downregulation of neutrophils. Increased corticosterone in mice subjected to maternal separation or social stress connects with significantly increased circulating neutrophils (Avitsur et al., 2002; Kinsey et al., 2008; Pinheiro et al., 2011; Zimecki et al., 2009). Zimacki et al (2009) have also shown that the lactoferrin-induced myelopoiesis leads to increased neutrophils in the blood of mice, and depends upon the lactoferrin-associated increase of serum corticosterone (Zimecki et al., 2009).

Although effective neutrophil-mediated responses are required for fighting infections, they are also key mediators of obesity-associated disorders, including cardiovascular disease and diabetes (FC, 2016; Manda-Handzlik and Demkow, 2015; Mayadas et al., 2014). The role of neutrophils in carcinogenesis and tumor evolution is also emerging, and a therapeutic approach of targeting tumor-associated neutrophils has been recently introduced (Coffelt S B, 2016; Gregory and Houghton, 2011; Manda-Handzlik and Demkow, 2015) (Rao et al., 2007; Rao et al., 2006) (Lakritz et al., 2015). According to a recent report the microbiota drives neutrophil aging via Toll-like receptor and myeloid differentiation factor 88, making aged neutrophils particularly effective as disease-promoting agents (Zhang et al., 2015a). In the light of this evidence, lowering the chronic systematic neutrophilic inflammatory tone without compromising ability of neutrophils to counteract pathogens may be important for human health. A previous study showing acceleration of skin wound healing using edible *L. reuteri* supplementation exemplifies such a therapeutic strategy (Poutahidis et al., 2013a). Using this mouse model, it was shown that *L. reuteri* did not compromise the beneficial acute stages of neutrophilic infiltration in the wound. Instead, it accelerated closure of the wound bed earlier in the healing process. Therefore *L. reuteri* treatment enforced the physiological balance of immune cells and orchestration of wound healing process and led to faster wound healing without compromising beneficial functions of specific immune cells including neutrophils (Poutahidis et al., 2013a).

Wound healing is an elementary biological process that includes the timely implementation of several different basic physiological phenomena (hemostasis, inflammation, extra-cellular matrix and connective tissue formation, angiogenesis, tissue remodeling). The ability to heal wounds effectively and swiftly reflects good health and fitness, and connects with youthfulness and longevity (Eming et al., 2014; Gurtner et al., 2008; Yanai et al., 2011). Therefore, the mouse skin wound healing model is an attractive platform to test the systemic health promoting effects of edible probiotic and postbiotic extract products. In the present study the present inventor demonstrates that lysed *L. reuteri* was as effective as the viable bacteria in accelerating skin wound healing in mice.

Going one step further, in the present studies the present inventor finds that human subject outcomes support benefit of *L. reuteri* with improved wound repair capacity, thus reinforcing the translational potential of findings in mice (Poutahidis et al., 2013a). Significant improvement in wound healing in just 14 patients with diverse backgrounds is exciting, and raises the question whether benefits will translate to individuals plagued with various other ailments including diabetes and heart disease. As ongoing trials begin to address these clinical implications, emerging data suggest health is indeed due largely to microbial factors that can be readily modified (Hsieh et al., 2016), that when harnessed impart resiliency typical of much younger subjects (Varian et al., 2014). Given the safety of food-grade microbes consumed in fermented beverages for thousands of years, edible bacteria and their products may offer a low-risk/high-impact remedy for trauma, elective procedures and poorly healing chronic wounds that affect millions of patients in the burgeoning health care and economic crisis.

Materials and Methods
Animal Models

Female outbred Swiss stock CD-1 female mice (Charles River, Wilmington Mass.), C57BL/6 wild type (wt), oxytocin-wt (ot-wt) and oxytocin-knockout (ot-ko) B6; 129S-Oxttm1Wsy/J mice (purchased initially from Jackson labs; Bar Harbor, Me.) were used in three separate experiments. Mice were housed and handled in Association for Assessment and Accreditation of Laboratory Animal Care (AAALAC)-accredited facilities using techniques and diets including *L. reuteri* as specifically approved by Massachusetts Institute of Technology's (MIT) Committee on Animal Care (CAC). Mice were housed under standard 12:12 light cycle conditions with lights on at 7 AM. Mice were fed a standard control chow Purina RMH3000.

Mouse models were bred in-house to achieve experimental groups. Mice were randomly assigned to experimental groups, and group housed with 4-5 mice per cage. Each experiment included 5-11 animals per group as specifically enumerated within the text. Mice received in their drinking water *L. reuteri* ATCC-PTA-6475 originally isolated from human breast milk.

*L. reuteri* Administration in Mouse Models

In each experiment, subsets of mice received in their drinking water a strain of *L. reuteri* ATCC-PTA-6475 cultivated as described elsewhere (Poutahidis et al., 2013a; Saulnier et al., 2011). Live organisms were supplied at a starting dosage of $3.5$-$5.0 \times 10^5$ organisms/mouse/day in drinking water (Lakritz et al., 2014), using oral dosage extrapolated from humans consuming daily chewable *L. reuteri* DSM17938 tablets (BioGaia Protectis). Live bacterial counts in water bottles were calculated to be $1.4 \times 10^6$ colony forming units (CFU) per mouse on day 1, $4.1 \times 10^5$ CFU on day 2, and $1.1 \times 10^5$ CFU on day 3. Fresh drinking water for both groups of animals was replaced twice weekly throughout the experiments. *L. reuteri* was detectable by PCR in feces and bowel of mice undergoing the live bacteria dosing regimen, as described in detail in Lakritz et al (2014).

Wound Repair Assay in Mice

Figure 14:
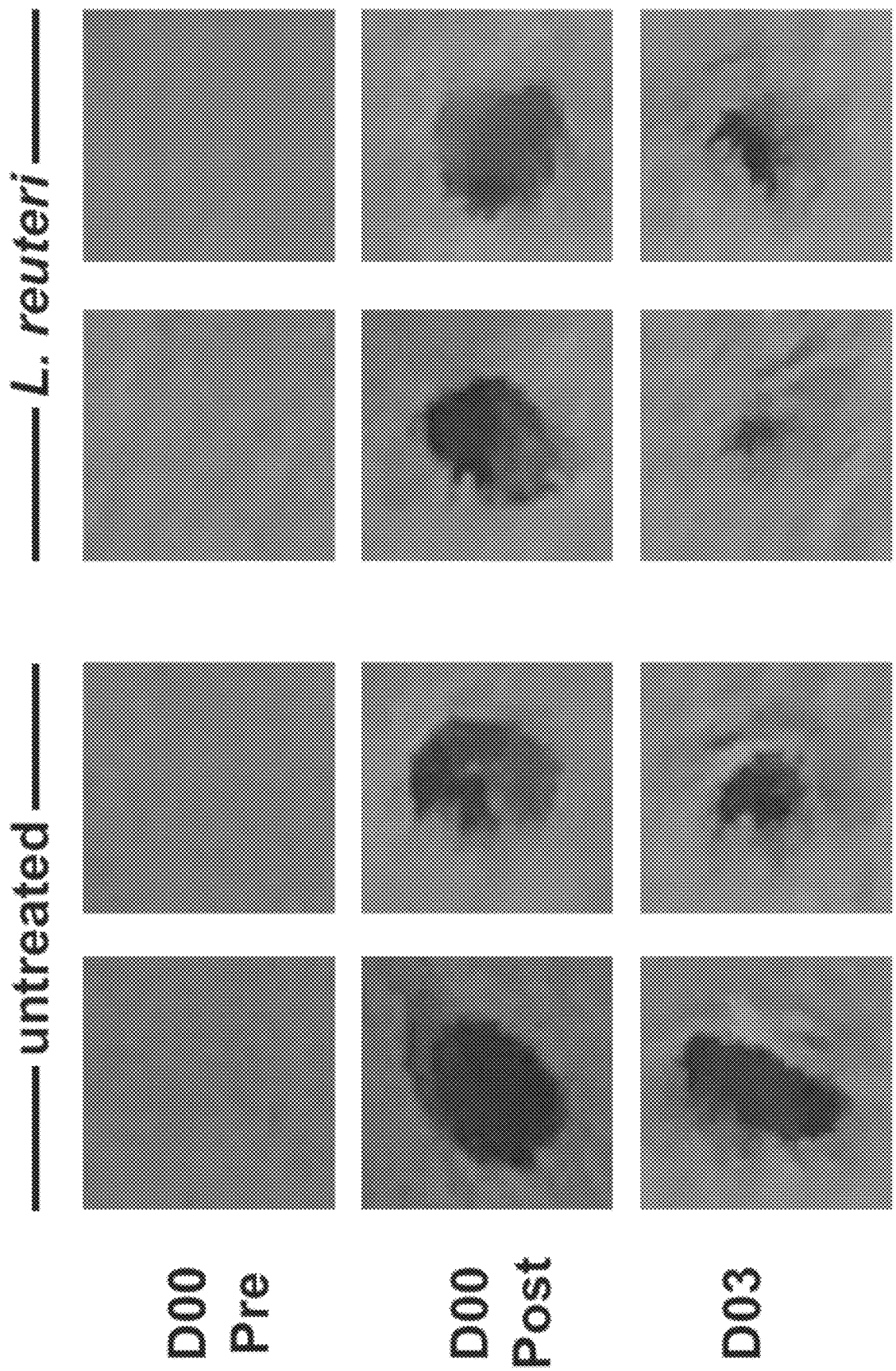
FIG. 14 demonstrates antemortem photography of representative Swiss mouse skin wounds. The skin is shown before and after the infliction of the biopsy wound. The original size of wound immediately after infliction (Day 00) was comparable between mice used for analysis. At day 3 post wounding *L. reuteri*-treated Swiss mice had smaller wounds compared to their untreated counterparts.

To test putative roles for microbes or microbe lysate-induced wound healing, as previously described in detail (Poutahidis et al., 2013a), mice underwent a standardized 2.0 mm dorsal cutaneous biopsy procedure under general inhalant isoflourane anesthesia with perioperative buprenorphine injectable analgesia. The mid-dorsal surgical procedures involved first shaving the biopsy site (FIG. 14), with alternating betadine and ethanol scrubs according to institutional policy, and finally the biopsy using a 2.0 mm cutaneous skin punch biopsy tool (Miltex Inc, York, Pa. USA). Mice were examined at six days after biopsy based upon significant differences that emerged in earlier studies (Poutahidis et al., 2013a). Mice entered experiments at eight weeks of age. Four weeks later (three weeks after start of *L. reuteri* or sham treatment plus six days of post-biopsy observation), at the conclusion of the study mice were euthanized with $CO_2$ overdose and wound areas were examined postmortem. Specifically, formalin-fixed, routinely-processed, paraffinized, flat wounded skin tissues were used for wound area measurements before being embedded in paraffin blocks. Direct microscopy with a Nikon eclipse 50i microscope and a Nikon DS-5 M-L1 digital camera was used to examine and photograph wounds in paraffinized gross skin specimens. The wound areas were subscribed and measured in images using the ImageJ image processing and analysis program (NIH, Bethesda, Md.). Results were recorded as image pixels.

Human Subject Trials

Figure 15:
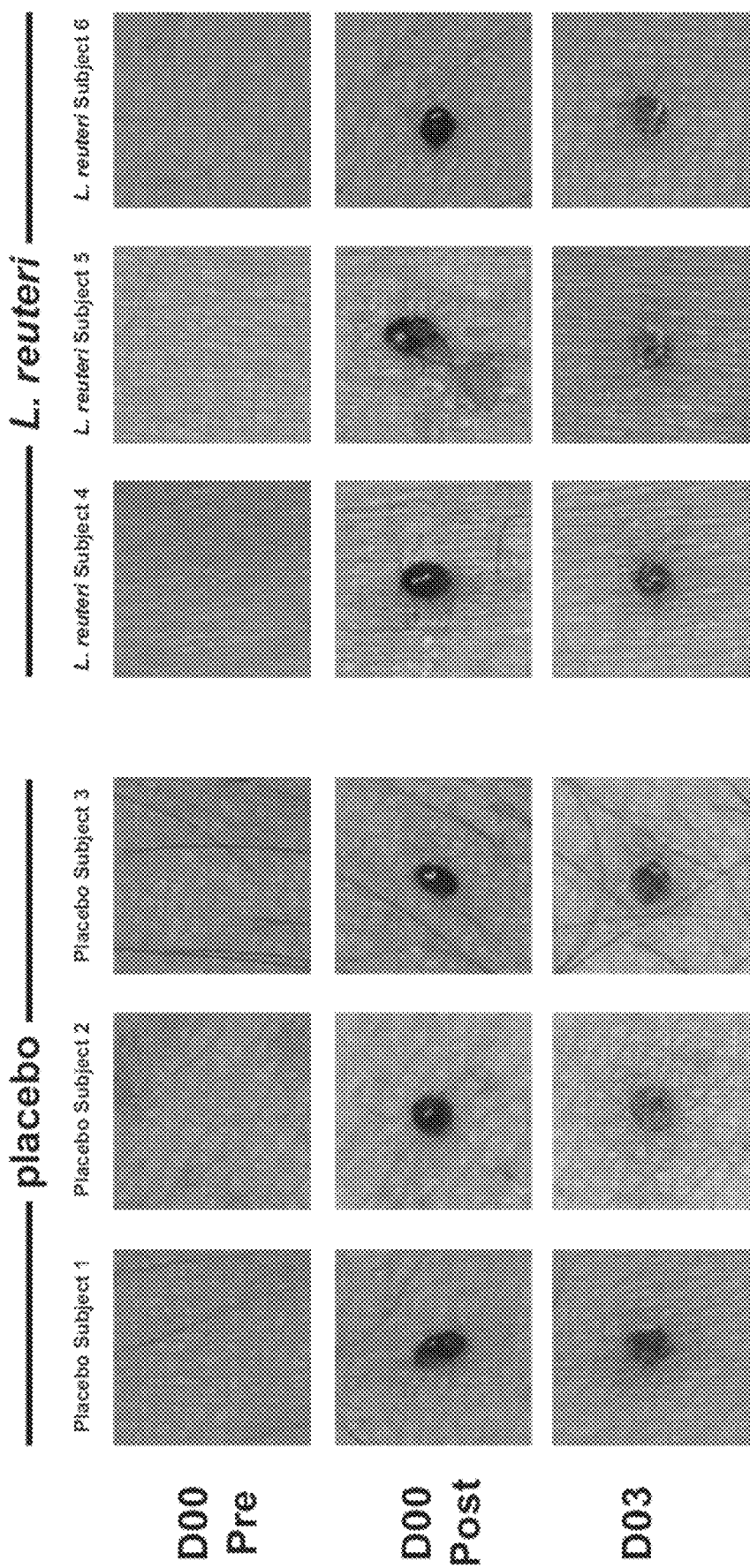
FIG. 15 shows photography of representative skin wounds upon biopsy in human subjects. Human female forearm skin is shown before and after wound infliction. The original size of wound immediately after infliction (Day 00) was comparable between human subjects of both treatment groups. At day 3 post-wounding, the *L. reuteri*-treated individuals had smaller wounds compared to their non-treated counterparts.
Figure 16A:
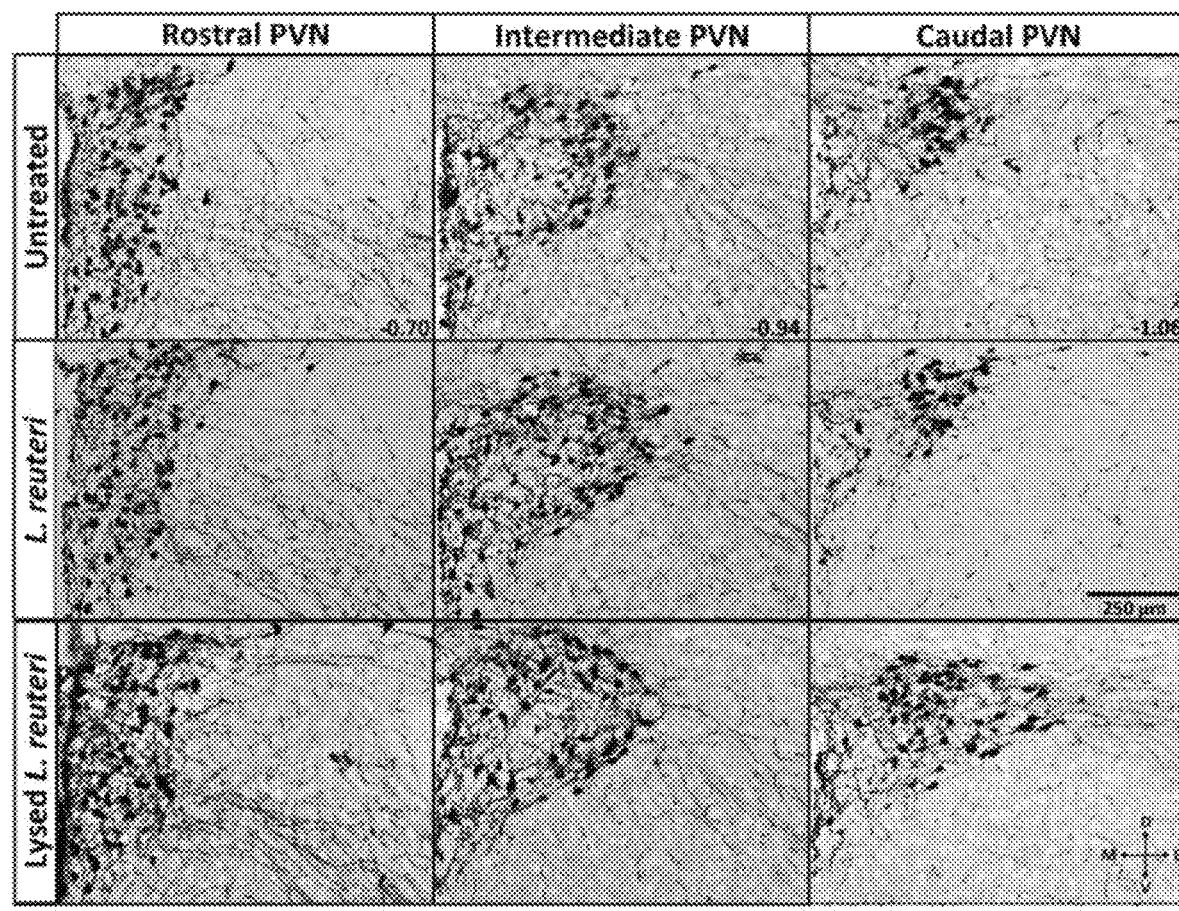
FIGS. 16A-16B demonstrate that mice treated with lysed *L. reuteri* had more oxytocin-immunoreactive (OT-ir) neurons in the caudal PVN.
Figure 16B:
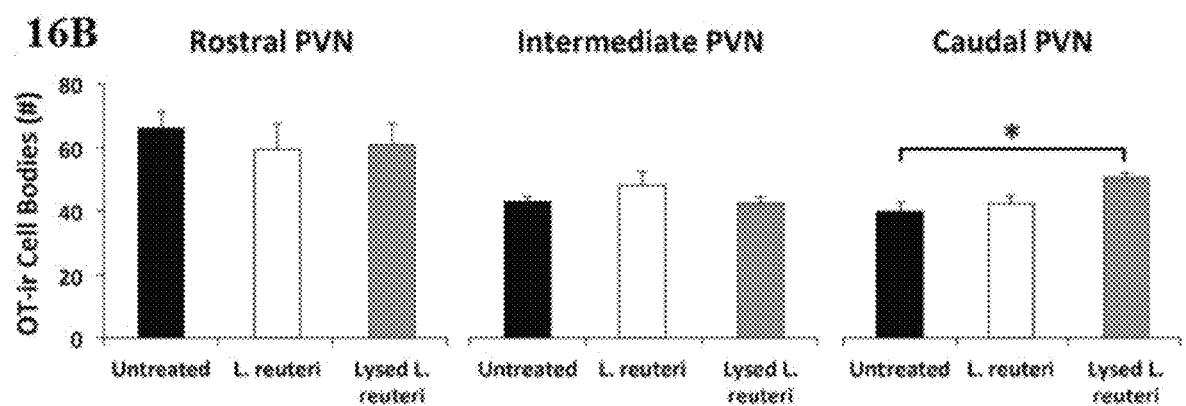

Fourteen healthy female volunteer subjects in a double blind placebo controlled study consumed chewable *L. reuteri* DSM17938 supplements (BioGaia Protectis) or placebo 60 mg vitamin C twice daily for three weeks before undergoing a full-thickness biopsy of forearm skin at MIT's Clinical Research Center. Female subjects only were selected in order to minimize differences between sexes, and to simultaneously gather data for skin appearance in females. Subjects (N=7 assigned randomly per treatment group) had a mean age of 29 years (range, 19-42y) and included individuals with diverse ethnicity (Suppl. Table 1, not included). Human skin wounds were photographed under standardized conditions at time points before and immediately after biopsy plus d3 after biopsy (FIG. 15). Individuals measuring the wounds and those collecting data were blind to the identity of experimental treatment groups.

The wound areas were subscribed (inset in FIG. 8A) and the subscribed area was measured in each image using ImageJ (NIH, Bethesda, Md.). Results were recorded in pixels, scaled and transformed in $mm^2$ using a standard scale originally contained in the images. To achieve that, wound area measurements were in pixels and then associated with the known distance of 1 mm according to the standard scale contained in the corresponding image, using the "set scale" command of ImageJ.

Production of Sterile Microbe Lysate

*L. reuteri* ATCC-PTA-6475 was cultivated using methods as previously described (Poutahidis et al., 2013a; Saulnier et al., 2011), confirmed for purity with a gram strain, and then suspended in sterile 1×PBS and measured for concentration with a spectrophotometer in order to calculate final dosages. A bacteria pellet was obtained by centrifugation for 10 minutes at 14,000 rpm and then resuspended and incubated in a Lysozyme STET buffer for 4 hours at 37 degrees Celsius. Bacteria-buffer was centrifuged for 10 minutes at 7,500 rpm to obtain a pellet, that was subsequently washed 2× and then resuspended in 1×PBS before lysing by sonication in an ice water bath at 20 kHz and the amplitude of 30% intensity for one-minute-on-then-one-minute-off for 25 minutes. Lysed bacteria was then centrifuged for 15 minutes at 4,000 rpm and passed through a 0.2 um filter to remove whole bacteria and large fragments, with the soluble supernatant being collected as the final product. The supernatant was then confirmed to be sterile using growth in anaerobic enriched thioglycollate media with Vitamin K1 and hemin (Bectin, Dickinson and Company, Sparks, Md.) and by the streak plate method on Sheep blood agar plates (Remel, Lanessa Kans.) with no growth after three days. Bacterial lysate was stored in 1 ml aliquots at −80 degrees Celsius until feeding to mice in experiments described above.

Special Microbial Treatments for Animals

Mice were fed standard rodent chow (RMH 3000; Purina Labs, St Louis Mo.). Subsets of animals were supplemented orally with intact or lysed ATCC strain of *L. reuteri* 6475 as described elsewhere (Lakritz et al., 2014; Varian et al., 2016b), using a supply dosage of $3.5 \times 10^5$ organisms/mouse/day continuously in drinking water. For Example 2A, Swiss mice received live intact *L. reuteri* organisms in drinking water. For Examples 2B and 2C, mice received *L. reuteri* as above, or, alternatively, controls received regular drinking water. For Example 2C, lysate confirmed to be sterile was delivered to C57BL/6 mice at the same concentration as live organisms in drinking water. Mice began drinking *L. reuteri* ATCC-PTA-6475 organisms, as above, starting at 8 wks of age, and then underwent skin biopsy three weeks later, followed by postmortem analyses at 12 weeks of age. Drinking water was replaced twice weekly to minimize variability in microbial exposure levels. In all cases, control animals received regular drinking water.

Determining Mass of Thymus Gland

Upon necropsy, intact mice were weighed in their entirety using a ScoutPro SP202 scale (Chaus Corporation, Pinebrook N.J.). Thymus tissue was removed and weighed separately.

Complete Blood Cell Counts

Whole blood was collected by cardiac puncture from unconscious animals upon necropsy and suspended in EDTA to prevent clotting. Automated neutrophil counts were then performed using mouse parameters in a HemaVet 950FS (Drew Scientific, Oxford Conn.). Counts were confirmed by manual reading of blood smears. Terminal blood collections for mice were performed mid-day for all subjects in order to minimize variability due to circadian rhythms.

Measurement of Plasma Oxytocin and Corticosterone Levels

Whole blood was collected terminally by cardiac puncture under general anesthesia to obtain plasma. Whole blood was collected into pre-chilled 5 ml EDTA tubes with 250 KIU of an oxytocin preservative, aprotinin, and refrigerated immediately until preparation of plasma. Plasma was isolated by centrifugation at 1800 g, 15 minutes, 4° C., and then stored in aliquots at −70° C. Plasma was then tested commercially for oxytocin and corticosterone by an outside laboratory with internal validations (AniLytics, Inc., Gaithersburg, Md.). Euthanasia for mice was performed mid-day for all subjects (n=8-10 per group) to minimize variability due to circadian rhythms.

Histopathology and Histomorphometry

Formalin-fixed tissues were embedded in paraffin, cut at 4-5 μm, and stained with hematoxylin and eosin (HE). Wound epidermal gap in histological images were measured using the ImageJ image processing and analysis program (NIH, Bethesda, Md.) as previously described (Poutahidis et al., 2013a).

Brain Tissue Collection and Immunohistochemistry for Oxytocin

Mouse brains (including skulls) were removed and fixed in 10% formalin and stored at 4° C. until further processing. Next, brains were dissected from the skull and post-fixed in 4% paraformaldehyde in 0.1M borate buffer (pH 9.5) for 48 h before cryoprotection in 30% sucrose (dissolved in basic physiologic saline; 0.9% NaCl) for 48 h. Following cryoprotection, brains were flash-frozen in cold methylbutane and stored at −45° C. Coronal (30 μm) sections were collected using a cryostat and were stored free-floating in tris-buffered saline (TBS) overnight at 4° C. The following day, tissue sections from each subject were immunolabeled for oxytocin (OT) (Ben-Barak et al., 1985; Franklin, 2008).

Oxytocin immunoreactivity (ir) was visualized using a monoclonal primary antibody provided by Dr. Harold Gainer (NINDS). This highly specific antibody was raised against mammalian oxytocin-associated neurophysins, and exhibits no cross-reactivity (Ben-Barak et al., 1985). Briefly, tissue sections were first washed in TBS, subjected to an antigen retrieval step (0.05M sodium citrate in TBS), blocked in blocking solution (20% normal goat serum (NGS), 0.3% Triton-X, 1% $H_2O_2$ in TBS), and incubated overnight at 4° C. in mouse anti-oxytocin (PS38; 1:100, 2% NGS, 0.3% Triton-X). Tissue sections were then rinsed in TBS and incubated in biotinylated secondary antibody solution (goat anti-mouse (1:500; Vector, Burlingame, Calif.), 2% NGS, 0.3% Triton-X in TBS) for 1 h. Tissue sections were incubated in avidin-biotin complex (ABC Elite Kit; Vector) for 1 h and visualized using diaminobenzadine (DAB peroxidase substrate kit; Vector). Sections were mounted on gelatin-coated slides, rinsed in 50% ethanol, air-dried and cover slipped using Permount (Fisher Scientific, Pittsburgh, Pa.).

Images were acquired under 20× magnification based on various anatomical landmarks specific to the following subregions of the hypothalamic paraventricular nucleus (PVN): rostral (−0.70 mm posterior to bregma), intermediate (−0.94 mm), and caudal (−1.06 mm), using the Mouse Brain Atlas (Franklin & Paxinos 2008) as a guide. Oxytocin-ir cell bodies were subsequently quantified from a representative tissue section in each region using the cell counter plugin in ImageJ (NIH; imagej.nih.gov/ij). Data are reported as the mean number of oxytocin-ir cell bodies per treatment in the rostral, intermediate, and caudal portions of the PVN.

Statistical Analysis

The Mann-Whitney U test was used for all statistical analyses (Graphpad Prism version 5.01 for windows, GraphPad software, San Diego, Calif., USA). The occurrence of wound scab detachment was compared between experimental groups with the Chi-square test. For analyzing oxytocin-positive cell counts, the present inventor used a one way ANOVA with a tukey post hoc test. Results are presented as the mean±standard error of the mean (SEM). Effects were considered to be significant at $p<0.05$.

REFERENCES

1. Abou-Ismail, U. A., Mahboub, H. D., 2011. The effects of enriching laboratory cages using various physical structures on multiple measures of welfare in singly-housed rats. Laboratory animals 45, 145-153.
2. Adams, C. A., 2010. The probiotic paradox: live and dead cells are biological response modifiers. Nutrition research reviews 23, 37-46.
3. Al-Amran, F., Shahkolahi, M., 2013. Oxytocin ameliorates the immediate myocardial injury in rat heart transplant through downregulation of neutrophil-dependent myocardial apoptosis. Transplant Proc 45, 2506-2512.
4. Avitsur, R., Stark, J. L., Dhabhar, F. S., Sheridan, J. F., 2002. Social stress alters splenocyte phenotype and function. J Neuroimmunol 132, 66-71.
5. Barengolts, E., 2016. Oxytocin—an Emerging Treatment for Obesity and Dysglycemia: Review of Randomized Controlled Trials and Cohort Studies. Endocrine practice: official journal of the American College of Endocrinology and the American Association of Clinical Endocrinologists.
6. Baribeau, D. A., Anagnostou, E., 2015. Oxytocin and vasopressin: linking pituitary neuropeptides and their receptors to social neurocircuits. Frontiers in neuroscience 9, 335.
7 Barnard, A., Layton, D., Hince, M., Sakkal, S., Bernard, C., Chidgey, A., Boyd, R., 2008. Impact of the neuroendocrine system on thymus and bone marrow function. Neuroimmunomodulation 15, 7-18.
8. Bartz, J., Simeon, D., Hamilton, H., Kim, S., Crystal, S., Braun, A., Vicens, V., Hollander, E., 2011. Oxytocin can hinder trust and cooperation in borderline personality disorder. Social cognitive and affective neuroscience 6, 556-563.
9. Ben-Barak, Y., Russell, J. T., Whitnall, M. H., Ozato, K., Gainer, H., 1985. Neurophysin in the hypothalamo-neurohypophysial system. I. Production and characterization of monoclonal antibodies. J Neurosci 5, 81-97.
10. Biyikli, N. K., Tugtepe, H., Sener, G., Velioglu-Ogunc, A., Cetinel, S., Midillioglu, S., Gedik, N., Yegen, B. C., 2006. Oxytocin alleviates oxidative renal injury in pyelonephritic rats via a neutrophil-dependent mechanism. Peptides 27, 2249-2257.
11. Blevins, J. E., Baskin, D. G., 2015. Translational and therapeutic potential of oxytocin as an anti-obesity strategy: Insights from rodents, nonhuman primates and humans. Physiol Behav 152, 438-449.
12. Bravo, J. A., Forsythe, P., Chew, M. V., Escaravage, E., Savignac, H. M., Dinan, T. G., Bienenstock, J., Cryan, J. F., 2011. Ingestion of *Lactobacillus* strain regulates emotional behavior and central GABA receptor expression in a mouse via the vagus nerve. Proc Natl Acad Sci USA 108, 16050-16055.
13. Britton, R. A., Irwin, R., Quach, D., Schaefer, L., Zhang, J., Lee, T., Parameswaran, N., McCabe, L. R., 2014. Probiotic *L. reuteri* treatment prevents bone loss in a menopausal ovariectomized mouse model. J Cell Physiol 229, 1822-1830.
14. Buffington, S. A., Di Prisco, G. V., Auchtung, T. A., Ajami, N. J., Petrosino, J. F., Costa-Mattioli, M., 2016. Microbial Reconstitution Reverses Maternal Diet-Induced Social and Synaptic Deficits in Offspring. Cell 165, 1762-1775.
15. Burkett, J. P., Andari, E., Johnson, Z. V., Curry, D. C., de Waal, F. B., Young, L. J., 2016. Oxytocin-dependent consolation behavior in rodents. Science 351, 375-378.
16. Carter, C. S., 2014. Oxytocin pathways and the evolution of human behavior. Annual review of psychology 65, 17-39.
17. Caselli, M., Vaira, G., Calo, G., Papini, F., Holton, J., Vaira, D., 2011. Structural bacterial molecules as potential candidates for an evolution of the classical concept of probiotics. Advances in nutrition 2, 372-376.
18. Clodi, M., Vila, G., Geyeregger, R., Riedl, M., Stulnig, T. M., Struck, J., Luger, T. A., Luger, A., 2008. Oxytocin alleviates the neuroendocrine and cytokine response to bacterial endotoxin in healthy men. Am J Physiol Endocrinol Metab 295, E686-691.
19. Coffelt S B, W. M., de Visser K E, 2016. Neutrophils in cancer: neutral no more. Nature Reviews Cancer 16, 16.
20. Cohen, H., Kaplan, Z., Kozlovsky, N., Gidron, Y., Matar, M. A., Zohar, J., 2010. Hippocampal microinfusion of oxytocin attenuates the behavioural response to stress by means of dynamic interplay with the glucocorticoid-catecholamine responses. J Neuroendocrinol 22, 889-904.
21. Colaianni, G., Sun, L., Zaidi, M., Zallone, A., 2014. Oxytocin and bone. Am J Physiol Regul Integr Comp Physiol 307, R970-977.
22. Collins, F. L., Irwin, R., Bierhalter, H., Schepper, J., Britton, R. A., Parameswaran, N., McCabe, L. R., 2016. *Lactobacillus reuteri* 6475 Increases Bone Density in Intact Females Only under an Inflammatory Setting. PLoS One 11, e0153180.
23. Costa, A., Rossi, E., Scicchitano, B. M., Coletti, D., Moresi, V., Adamo, S., 2014. Neurohypophyseal Hormones: Novel Actors of Striated Muscle Development and Homeostasis. European journal of translational myology 24, 3790.
24. Cruchet, S., Furnes, R., Maruy, A., Hebel, E., Palacios, J., Medina, F., Ramirez, N., Orsi, M., Rondon, L., Sdepanian, V., Xochihua, L., Ybarra, M., Zablah, R. A., 2015. The use of probiotics in pediatric gastroenterology: a review of the literature and recommendations by Latin-American experts. Paediatric drugs 17, 199-216.
25. Cruz, F. C., Marin, M. T., Leao, R. M., Planeta, C. S., 2012. Behavioral and neuroendocrine effects of the exposure to chronic restraint or variable stress in early adolescent rats. Int J Dev Neurosci 30, 19-23.
26. De Dreu, C. K., Greer, L. L., Van Kleef, G. A., Shalvi, S., Handgraaf, M. J., 2011. Oxytocin promotes human ethnocentrism. Proc Natl Acad Sci USA 108, 1262-1266.
27. Dinan, T. G., Stanton, C., Cryan, J. F., 2013. Psychobiotics: a novel class of psychotropic. Biol Psychiatry 74, 720-726.
28. Donaldson, Z. R., Young, L. J., 2008. Oxytocin, vasopressin, and the neurogenetics of sociality. Science 322, 900-904.
29. Elabd, C., Cousin, W., Upadhyayula, P., Chen, R. Y., Chooljian, M. S., Li, J., Kung, S., Jiang, K. P., Conboy, I. M., 2014. Oxytocin is an age-specific circulating hormone that is necessary for muscle maintenance and regeneration. Nature communications 5, 4082.
30. Eliava, M., Melchior, M., Knobloch-Bollmann, H. S., Wahis, J., da Silva Gouveia, M., Tang, Y., Ciobanu, A. C., Triana del Rio, R., Roth, L. C., Althammer, F., Chavant, V., Goumon, Y., Gruber, T., Petit-Demouliere, N., Busnelli, M., Chini, B., Tan, L. L., Mitre, M., Froemke, R. C., Chao, M. V., Giese, G., Sprengel, R., Kuner, R., Poisbeau, P., Seeburg, P. H., Stoop, R., Charlet, A., Grinevich, V., 2016. A New Population of Parvocellular Oxytocin Neurons Controlling Magnocellular Neuron Activity and Inflammatory Pain Processing. Neuron 89, 1291-1304.
31. Eming, S. A., Martin, P., Tomic-Canic, M., 2014. Wound repair and regeneration: mechanisms, signaling, and translation. Sci Transl Med 6, 265 sr266.
32. Erdman, S. E., Poutahidis, T., 2010. Cancer inflammation and regulatory T cells. Int J Cancer 127, 768-779.
33. Erdman, S. E., Poutahidis, T., 2014. Probiotic 'glow of health': it's more than skin deep. Benef Microbes 5, 109-119.
34. Fak, F., Backhed, F., 2012. *Lactobacillus reuteri* prevents diet-induced obesity, but not atherosclerosis, in a strain dependent fashion in Apoe-/- Mice. PLoS One 7, e46837.
35. FC, P., 2016. The role of inflammation in cardiovascular diseases: the predictive value of neutrophil-lymphocyte ratio as a marker in peripheral arterial disease. Journal of Therapeutics and Clinical Risk Management 12, 10.
36. Feldman, R., Monakhov, M., Pratt, M., Ebstein, R. P., 2016. Oxytocin Pathway Genes: Evolutionary Ancient System Impacting on Human Affiliation, Sociality, and Psychopathology. Biol Psychiatry 79, 174-184.
37. Forsythe, P., Inman, M. D., Bienenstock, J., 2007. Oral treatment with live *Lactobacillus reuteri* inhibits the allergic airway response in mice. Am J Respir Crit Care Med 175, 561-569.
38. Franklin, K. B. J. P., G., 2008. The Mouse Brain in Stereotaxic Coordinates. Gulf Professional Publishing, San Diego, Calif.
39. Gao, C., Major, A., Rendon, D., Lugo, M., Jackson, V., Shi, Z., Mori-Akiyama, Y., Versalovic, J., 2015. Histamine H2 Receptor-Mediated Suppression of Intestinal Inflammation by Probiotic *Lactobacillus reuteri*. mBio 6, e01358-01315.

40. Gavrilenko, V. G., Esipov, V. K., Sivozhelezov, K. G., 2003. [Morphological characteristic of wound healing process in patients with diabetic purulent-necrotic foot lesion treated with oxytocin]. Morfologiia 124, 24-27.
41. Gimpl, G., Fahrenholz, F., 2001. The oxytocin receptor system: structure, function, and regulation. Physiological reviews 81, 629-683.
42. Gouin, J. P., Carter, C. S., Pournajafi-Nazarloo, H., Glaser, R., Malarkey, W. B., Loving, T. J., Stowell, J., Kiecolt-Glaser, J. K., 2010. Marital behavior, oxytocin, vasopressin, and wound healing. Psychoneuroendocrinology 35, 1082-1090.
43. Gregory, A. D., Houghton, A. M., 2011. Tumor-associated neutrophils: new targets for cancer therapy. Cancer Res 71, 2411-2416.
44. Griet, M., Zelaya, H., Mateos, M. V., Salva, S., Juarez, G. E., de Valdez, G. F., Villena, J., Salvador, G. A., Rodriguez, A. V., 2014. Soluble factors from *Lactobacillus reuteri* CRL1098 have anti-inflammatory effects in acute lung injury induced by lipopolysaccharide in mice. PLoS One 9, e110027.
45. Gurtner, G. C., Werner, S., Barrandon, Y., Longaker, M. T., 2008. Wound repair and regeneration. Nature 453, 314-321.
46. Hansenne, I., Louis, C., Martens, H., Dorban, G., Charlet-Renard, C., Peterson, P., Geenen, V., 2009. Aire and Foxp3 expression in a particular microenvironment for T cell differentiation. Neuroimmunomodulation 16, 35-44.
47. Hansenne, I., Rasier, G., Pequeux, C., Brilot, F., Renard, C., Breton, C., Greimers, R., Legros, J. J., Geenen, V., Martens, H. J., 2005. Ontogenesis and functional aspects of oxytocin and vasopressin gene expression in the thymus network. J Neuroimmunol 158, 67-75.
48. Herman, J. P., Cullinan, W. E., Ziegler, D. R., Tasker, J. G., 2002a. Role of the paraventricular nucleus microenvironment in stress integration. Eur J Neurosci 16, 381-385.
49. Herman, J. P., Tasker, J. G., Ziegler, D. R., Cullinan, W. E., 2002b. Local circuit regulation of paraventricular nucleus stress integration: glutamate-GABA connections. Pharmacology, biochemistry, and behavior 71, 457-468.
50. Hsieh, F. C., Lan, C. C., Huang, T. Y., Chen, K. W., Chai, C. Y., Chen, W. T., Fang, A. H., Chen, Y. H., Wu, C. S., 2016. Heat-killed and live *Lactobacillus reuteri* GMNL-263 exhibit similar effects on improving metabolic functions in high-fat diet-induced obese rats. Food Funct 7, 2374-2388.
51. Ibrahim, Y. M. K., S. M.; Levkovich, T.; Springer, A.; Mirabal, S.; Poutahidis, T.; Varian, B. J.; Lakritz, J. R.; Alm, E. J.; Erdman, S. E., 2014. Maternal Gut Microbes Control Offspring Sex and Survival. Journal of Probiotics and Health 2, 6.
52. Iniesta, M., Herrera, D., Montero, E., Zurbriggen, M., Matos, A. R., Marin, M. J., Sanchez-Beltran, M. C., Llama-Palacio, A., Sanz, M., 2012. Probiotic effects of orally administered *Lactobacillus reuteri*-containing tablets on the subgingival and salivary microbiota in patients with gingivitis. A randomized clinical trial. Journal of clinical periodontology 39, 736-744.
53. Iseri, S. O., Sener, G., Saglam, B., Gedik, N., Ercan, F., Yegen, B. C., 2005a. Oxytocin ameliorates oxidative colonic inflammation by a neutrophil-dependent mechanism. Peptides 26, 483-491.
54. Iseri, S. O., Sener, G., Saglam, B., Gedik, N., Ercan, F., Yegen, B. C., 2005b. Oxytocin protects against sepsis-induced multiple organ damage: role of neutrophils. J Surg Res 126, 73-81.
55. Jard, S., Barberis, C., Audigier, S., Tribollet, E., 1987. Neurohypophyseal hormone receptor systems in brain and periphery. Prog Brain Res 72, 173-187.
56. Kamiya, T., Wang, L., Forsythe, P., Goettsche, G., Mao, Y., Wang, Y., Tougas, G., Bienenstock, J., 2006. Inhibitory effects of *Lactobacillus reuteri* on visceral pain induced by colorectal distension in Sprague-Dawley rats. Gut 55, 191-196.
57. Kataria, J., Li, N., Wynn, J. L., Neu, J., 2009. Probiotic microbes: do they need to be alive to be beneficial? Nutr Rev 67, 546-550.
58. Kelly, J. R., Clarke, G., Cryan, J. F., Dinan, T. G., 2016. Brain-gut-microbiota axis: challenges for translation in psychiatry. Ann Epidemiol 26, 366-372.
59. Kinsey, S. G., Bailey, M. T., Sheridan, J. F., Padgett, D. A., 2008. The inflammatory response to social defeat is increased in older mice. Physiol Behav 93, 628-636.
60. Knobloch, H. S., Charlet, A., Hoffmann, L. C., Eliava, M., Khrulev, S., Cetin, A. H., Osten, P., Schwarz, M. K., Seeburg, P. H., Stoop, R., Grinevich, V., 2012. Evoked axonal oxytocin release in the central amygdala attenuates fear response. Neuron 73, 553-566.
61. Lakritz, J. R., Poutahidis, T., Levkovich, T., Varian, B. J., Ibrahim, Y. M., Chatzigiagkos, A., Mirabal, S., Alm, E. J., Erdman, S. E., 2014. Beneficial bacteria stimulate host immune cells to counteract dietary and genetic predisposition to mammary cancer in mice. Int J Cancer 135, 529-540.
62. Lakritz, J. R., Poutahidis, T., Mirabal, S., Varian, B. J., Levkovich, T., Ibrahim, Y. M., Ward, J. M., Teng, E. C., Fisher, B., Parry, N., Lesage, S., Alberg, N., Gourishetti, S., Fox, J. G., Ge, Z., Erdman, S. E., 2015. Gut bacteria require neutrophils to promote mammary tumorigenesis. Oncotarget 6, 9387-9396.
63. Landgraf, R., Neumann, I. D., 2004. Vasopressin and oxytocin release within the brain: a dynamic concept of multiple and variable modes of neuropeptide communication. Frontiers in neuroendocrinology 25, 150-176.
64. Lee, J., Yang, W., Hostetler, A., Schultz, N., Suckow, M. A., Stewart, K. L., Kim, D. D., Kim, H. S., 2016. Characterization of the anti-inflammatory *Lactobacillus reuteri* BM36301 and its probiotic benefits on aged mice. BMC Microbiol 16, 69.
65. Lefevre, A., Sirigu, A., 2016. The two fold role of oxytocin in social developmental disorders: A cause and a remedy? Neurosci Biobehav Rev 63, 168-176.
66. Leng, G., Ludwig, M., 2016. Intranasal Oxytocin: Myths and Delusions. Biol Psychiatry 79, 243-250.
67. Levkovich, T., Poutahidis, T., Smillie, C., Varian, B. J., Ibrahim, Y. M., Lakritz, J. R., Alm, E. J., Erdman, S. E., 2013. Probiotic bacteria induce a 'glow of health'. PLoS One 8, e53867.
68. Listowska, M., Glac, W., Grembecka, B., Grzybowska, M., Wrona, D., 2015. Changes in blood CD4+T and CD8+T lymphocytes in stressed rats pretreated chronically with desipramine are more pronounced after chronic open field stress challenge. J Neuroimmunol 282, 54-62.
69. Liu, Y., Fatheree, N. Y., Mangalat, N., Rhoads, J. M., 2012. *Lactobacillus reuteri* strains reduce incidence and severity of experimental necrotizing enterocolitis via modulation of TLR4 and NF-kappaB signaling in the intestine. Am J Physiol Gastrointest Liver Physiol 302, G608-617.
70. Livingston, M., Loach, D., Wilson, M., Tannock, G. W., Baird, M., 2010. Gut commensal *Lactobacillus reuteri* 100-23 stimulates an immunoregulatory response. Immunology and cell biology 88, 99-102.

71. Ludwig, M., Leng, G., 2006. Dendritic peptide release and peptide-dependent behaviours. Nat Rev Neurosci 7, 126-136.
72. Manda-Handzlik, A., Demkow, U., 2015. Neutrophils: The Role of Oxidative and Nitrosative Stress in Health and Disease. Adv Exp Med Biol 857, 51-60.
73. Martin-Cabezas, R., Davideau, J. L., Tenenbaum, H., Huck, O., 2016. Clinical efficacy of probiotics as an adjunctive therapy to non-surgical periodontal treatment of chronic periodontitis: a systematic review and meta-analysis. Journal of clinical periodontology 43, 520-530.
74. Mayadas, T. N., Cullere, X., Lowell, C. A., 2014. The multifaceted functions of neutrophils. Annu Rev Pathol 9, 181-218.
75. Mehling, H., Busjahn, A., 2013. Non-viable *Lactobacillus reuteri* DSMZ 17648 (Pylopass) as a new approach to *Helicobacter pylori* control in humans. Nutrients 5, 3062-3073.
76. Monteiro, S., Roque, S., de Sa-Calcada, D., Sousa, N., Correia-Neves, M., Cerqueira, J. J., 2015. An efficient chronic unpredictable stress protocol to induce stress-related responses in C57BL/6 mice. Frontiers in psychiatry 6, 6.
77. Nehls, M., Pfeifer, D., Schorpp, M., Hedrich, H., Boehm, T., 1994. New member of the winged-helix protein family disrupted in mouse and rat nude mutations. Nature 372, 103-107.
78. Nomura, T., Sakaguchi, S., 2007. Foxp3 and Aire in thymus-generated Treg cells: a link in self-tolerance. Nat Immunol 8, 333-334.
79. Petersson, M., Wiberg, U., Lundeberg, T., Uvnas-Moberg, K., 2001. Oxytocin decreases carrageenan induced inflammation in rats. Peptides 22, 1479-1484.
80. Pinheiro, M. L., Ferraz-de-Paula, V., Ribeiro, A., Sakai, M., Bernardi, M. M., Palermo-Neto, J., 2011. Long-term maternal separation differentially alters serum corticosterone levels and blood neutrophil activity in A/J and C57BL/6 mouse offspring. Neuroimmunomodulation 18, 184-190.
81. Poutahidis, T., Kearney, S. M., Levkovich, T., Qi, P., Varian, B. J., Lakritz, J. R., Ibrahim, Y. M., Chatzigiagkos, A., Alm, E. J., Erdman, S. E., 2013a. Microbial Symbionts Accelerate Wound Healing via the Neuropeptide Hormone Oxytocin. PLoS One 8, e78898.
82. Poutahidis, T., Kleinewietfeld, M., Smillie, C., Levkovich, T., Perrotta, A., Bhela, S., Varian, B. J., Ibrahim, Y. M., Lakritz, J. R., Kearney, S. M., Chatzigiagkos, A., Hafler, D. A., Alm, E. J., Erdman, S. E., 2013b. Microbial reprogramming inhibits Western diet-associated obesity. PLoS One 8, e68596.
83. Poutahidis, T., Springer, A., Levkovich, T., Qi, P., Varian, B. J., Lakritz, J. R., Ibrahim, Y. M., Chatzigiagkos, A., Alm, E. J., Erdman, S. E., 2014. Probiotic microbes sustain youthful serum testosterone levels and testicular size in aging mice. PLoS One 9, e84877.
84. Poutahidis, T., Varian, B. J., Levkovich, T., Lakritz, J. R., Mirabal, S., Kwok, C., Ibrahim, Y. M., Kearney, S. M., Chatzigiagkos, A., Alm, E. J., Erdman, S. E., 2015. Dietary microbes modulate transgenerational cancer risk. Cancer Res 75, 1197-1204.
85. Preidis, G. A., Versalovic, J., 2009. Targeting the human microbiome with antibiotics, probiotics, and prebiotics: gastroenterology enters the metagenomics era. Gastroenterology 136, 2015-2031.
86. Qiao, Y., Sun, J., Xia, S., Li, L., Li, Y., Wang, P., Shi, Y., Le, G., 2015. Effects of different *lactobacillus reuteri* on inflammatory and fat storage in high-fat diet-induced obesity mice model. Journal of Functional Foods 14, 424-434.
87. Rao, V. P., Poutahidis, T., Fox, J. G., Erdman, S. E., 2007. Breast cancer: should gastrointestinal bacteria be on our radar screen? Cancer Res 67, 847-850.
88. Rao, V. P., Poutahidis, T., Ge, Z., Nambiar, P. R., Horwitz, B. H., Fox, J. G., Erdman, S. E., 2006. Proinflammatory CD4+CD45RB(hi) lymphocytes promote mammary and intestinal carcinogenesis in Apc(Min/+) mice. Cancer Res 66, 57-61.
89. Romano, R., Palamaro, L., Fusco, A., Giardino, G., Gallo, V., Del Vecchio, L., Pignata, C., 2013. FOXN1: A Master Regulator Gene of Thymic Epithelial Development Program. Front Immunol 4, 187.
90. Rook, G. A., 2013. Regulation of the immune system by biodiversity from the natural environment: an ecosystem service essential to health. Proc Natl Acad Sci USA 110, 18360-18367.
91. Rosa, E. F., Alves, G. A., Luz, J., Silva, S. M., Suchecki, D., Pesquero, J. B., Aboulafia, J., Nouailhetas, V. L., 2014. Activation of HPA axis and remodeling of body chemical composition in response to an intense and exhaustive exercise in C57BL/6 mice. Physiological research/Academia Scientiarum Bohemoslovaca 63, 605-613.
92. Ruiz, L., Hevia, A., Bernardo, D., Margolies, A., Sanchez, B., 2014. Extracellular molecular effectors mediating probiotic attributes. Fems Microbiol Lett 359, 1-11.
93. Sanchez, B., Urdaci, M. C., Margolies, A., 2010. Extracellular proteins secreted by probiotic bacteria as mediators of effects that promote mucosa-bacteria interactions. Microbiology 156, 3232-3242.
94. Saulnier, D. M., Santos, F., Roos, S., Mistretta, T. A., Spinler, J. K., Molenaar, D., Teusink, B., Versalovic, J., 2011. Exploring metabolic pathway reconstruction and genome-wide expression profiling in *Lactobacillus reuteri* to define functional probiotic features. PLoS One 6, e18783.
95. Savignac, H. M., Finger, B. C., Pizzo, R. C., O'Leary, O. F., Dinan, T. G., Cryan, J. F., 2011. Increased sensitivity to the effects of chronic social defeat stress in an innately anxious mouse strain. Neuroscience 192, 524-536.
96. Schreiber, O., Petersson, J., Phillipson, M., Perry, M., Roos, S., Holm, L., 2009. *Lactobacillus reuteri* prevents colitis by reducing P-selectin-associated leukocyte- and platelet-endothelial cell interactions. Am J Physiol Gastrointest Liver Physiol 296, G534-542.
97. Seetharaman, S., Fleshner, M., Park, C. R., Diamond, D. M., 2016. Influence of daily social stimulation on behavioral and physiological outcomes in an animal model of PTSD. Brain and behavior 6, e00458.
98. Seijkens, T., Kusters, P., Chatzigeorgiou, A., Chavakis, T., Lutgens, E., 2014. Immune cell crosstalk in obesity: a key role for costimulation? Diabetes 63, 3982-3991.
99. Sherwin, E., Rea, K., Dinan, T. G., Cryan, J. F., 2016. A gut (microbiome) feeling about the brain. Curr Opin Gastroenterol 32, 96-102.
100. Simon, M. C., Strassburger, K., Nowotny, B., Kolb, H., Nowotny, P., Burkart, V., Zivehe, F., Hwang, J. H., Stehle, P., Pacini, G., Hartmann, B., Holst, J. J., MacKenzie, C., Bindels, L. B., Martinez, I., Walter, J., Henrich, B., Schloot, N. C., Roden, M., 2015. Intake of *Lactobacillus reuteri* improves incretin and insulin secretion in glucose-tolerant humans: a proof of concept. Diabetes care 38, 1827-1834.
101. Smith, A. S., Tabbaa, M., Lei, K., Eastham, P., Butler, M. J., Linton, L., Altshuler, R., Liu, Y., Wang, Z., 2016a.

Local oxytocin tempers anxiety by activating GABAA receptors in the hypothalamic paraventricular nucleus. Psychoneuroendocrinology 63, 50-58.

102. Smith, C. J., Poehlmann, M. L., Li, S., Ratnaseelan, A. M., Bredewold, R., Veenema, A. H., 2016b. Age and sex differences in oxytocin and vasopressin V1a receptor binding densities in the rat brain: focus on the social decision-making network. Brain Struct Funct.

103. Stanic, D., Plecas-Solarovic, B., Petrovic, J., Bogavac-Stanojevic, N., Sopic, M., Kotur-Stevuljevic, J., Ignjatovic, S., Pesic, V., 2016. Hydrogen peroxide-induced oxidative damage in peripheral blood lymphocytes from rats chronically treated with corticosterone: The protective effect of oxytocin treatment. Chemico-biological interactions 256, 134-141.

104. Sun, L., Tamma, R., Yuen, T., Colaianni, G., Ji, Y., Cuscito, C., Bailey, J., Dhawan, S., Lu, P., Calvano, C. D., Zhu, L. L., Zambonin, C. G., Di Benedetto, A., Stachnik, A., Liu, P., Grano, M., Colucci, S., Davies, T. F., New, M. I., Zallone, A., Zaidi, M., 2016. Functions of vasopressin and oxytocin in bone mass regulation. Proc Natl Acad Sci USA 113, 164-169.

105. Surana, N. K., Kasper, D. L., 2012. The yin yang of bacterial polysaccharides: lessons learned from *B. fragilis* PSA. Immunol Rev 245, 13-26.

106. Tamma, R., Colaianni, G., Zhu, L. L., DiBenedetto, A., Greco, G., Montemurro, G., Patano, N., Strippoli, M., Vergari, R., Mancini, L., Colucci, S., Grano, M., Faccio, R., Liu, X., Li, J., Usmani, S., Bachar, M., Bab, I., Nishimori, K., Young, L. J., Buettner, C., Iqbal, J., Sun, L., Zaidi, M., Zallone, A., 2009. Oxytocin is an anabolic bone hormone. Proc Natl Acad Sci USA 106, 7149-7154.

107. Taub, D. D., Longo, D. L., 2005. Insights into thymic aging and regeneration. Immunol Rev 205, 72-93.

108. Thomas, C. M., Saulnier, D. M., Spinler, J. K., Hemarajata, P., Gao, C., Jones, S. E., Grimm, A., Balderas, M. A., Burstein, M. D., Morra, C., Roeth, D., Kalkum, M., Versalovic, J., 2016. FolC2-mediated folate metabolism contributes to suppression of inflammation by probiotic *Lactobacillus reuteri*. MicrobiologyOpen.

109. Ting, W. J., Kuo, W. W., Hsieh, D. J., Yeh, Y. L., Day, C. H., Chen, Y. H., Chen, R. J., Padma, V. V., Chen, Y. H., Huang, C. Y., 2015a. Heat Killed *Lactobacillus reuteri* GMNL-263 Reduces Fibrosis Effects on the Liver and Heart in High Fat Diet-Hamsters via TGF-beta Suppression. Int J Mol Sci 16, 25881-25896.

110. Ting, W. J., Kuo, W. W., Kuo, C. H., Yeh, Y. L., Shen, C. Y., Chen, Y. H., Ho, T. J., Viswanadha, V. P., Huang, C. Y., 2015b. Supplementary heat-killed *Lactobacillus reuteri* GMNL-263 ameliorates hyperlipidaemic and cardiac apoptosis in high-fat diet-fed hamsters to maintain cardiovascular function. Br J Nutr 114, 706-712.

111. Van Loo, P. L., Van der Meer, E., Kruitwagen, C. L., Koolhaas, J. M., Van Zutphen, L. F., Baumans, V., 2004. Long-term effects of husbandry procedures on stress-related parameters in male mice of two strains. Laboratory animals 38, 169-177.

112. Varian, B. J., Goureshetti, S., Poutahidis, T., Lakritz, J. R., Levkovich, T., Kwok, C., Teliousis, K., Ibrahim, Y. M., Mirabal, S., Erdman, S. E., 2016a. Beneficial bacteria inhibit cachexia. Oncotarget 7, 11803-11816.

113. Varian, B. J., Levkovich, T., Poutahidis, T., Ibrahim, Y. M., Perrotta, A., Alm, E. J., Erdman, S. E., 2016b. Beneficial Dog Bacteria Up-Regulate Oxytocin and Lower Risk of Obesity. Journal of Probiotics & Health 4, 1-9.

114. Varian, B. J., Poutahidis, T., Levkovich, T., Ibrahim, Y. M., Lakritz, J. R., Chatzigiagkos, A., Scherer-Hoock, A., Alm, E. J., Erdman, S. E., 2014. Beneficial Bacteria Stimulate Youthful Thyroid Gland Activity. Journal of Obesity and Weight Loss Therapy 4, 1-8.

115. Ventevogel, M. S., Sempowski, G. D., 2013. Thymic rejuvenation and aging. Curr Opin Immunol 25, 516-522.

116. Vilela, F. C., Antunes-Rodrigues, J., Elias, L. L., Giusti-Paiva, A., 2013. Corticosterone synthesis inhibitor metyrapone preserves changes in maternal behavior and neuroendocrine responses during immunological challenge in lactating rats. Neuroendocrinology 97, 322-330.

117. Vitalo, A., Fricchione, J., Casali, M., Berdichevsky, Y., Hoge, E. A., Rauch, S. L., Berthiaume, F., Yarmush, M. L., Benson, H., Fricchione, G. L., Levine, J. B., 2009. Nest making and oxytocin comparably promote wound healing in isolation reared rats. PLoS One 4, e5523.

118. Walter, J., Britton, R. A., Roos, S., 2011. Host-microbial symbiosis in the vertebrate gastrointestinal tract and the *Lactobacillus reuteri* paradigm. Proc Natl Acad Sci USA 108 Suppl 1, 4645-4652.

119. Wang, J., Tai, F., Yan, X., Yu, P., 2012. Paternal deprivation alters play-fighting, serum corticosterone and the expression of hypothalamic vasopressin and oxytocin in juvenile male mandarin voles. Journal of comparative physiology. A, Neuroethology, sensory, neural, and behavioral physiology 198, 787-796.

120. Wang, P., Yang, H. P., Tian, S., Wang, L., Wang, S. C., Zhang, F., Wang, Y. F., 2015. Oxytocin-secreting system: A major part of the neuroendocrine center regulating immunologic activity. J Neuroimmunol 289, 152-161.

121. Yanai, H., Budovsky, A., Tacutu, R., Fraifeld, V. E., 2011. Is rate of skin wound healing associated with aging or longevity phenotype? Biogerontology 12, 591-597.

122. Youn, D. Y., Yoon, J. S., Kim, Y. K., Yeum, C. E., Lee, S. B., Youn, H. J., Tsujimoto, Y., Lee, J. H., 2011. Deletion of the bis gene results in a marked increase in the production of corticosterone that is associated with thymic atrophy in mice. Am J Physiol Endocrinol Metab 301, E223-231.

123. Zhang, D., Chen, G., Manwani, D., Mortha, A., Xu, C., Faith, J. J., Burk, R. D., Kunisaki, Y., Jang, J. E., Scheiermann, C., Merad, M., Frenette, P. S., 2015a. Neutrophil ageing is regulated by the microbiome. Nature 525, 528-532.

124. Zhang, J., Motyl, K. J., Irwin, R., MacDougald, O. A., Britton, R. A., McCabe, L. R., 2015b. Loss of Bone and Wnt10b Expression in Male Type 1 Diabetic Mice Is Blocked by the Probiotic *Lactobacillus reuteri*. Endocrinology 156, 3169-3182.

125. Zhang, Z., Burnley, P., Coder, B., Su, D. M., 2012. Insights on FoxN1 biological significance and usages of the "nude" mouse in studies of T-lymphopoiesis. International journal of biological sciences 8, 1156-1167.

126. Zimecki, M., Artym, J., Kocieba, M., 2009. Endogenous steroids are responsible for lactoferrin-induced myelopoiesis in mice. Pharmacological reports: PR 61, 705-710.

127. Zivkovic, I. P., Rakin, A. K., Petrovic-Djergovic, D. M., Kosec, D. J., Micic, M. V., 2005. Exposure to forced swim stress alters morphofunctional characteristics of the rat thymus. J Neuroimmunol 160, 77-86.

What is claimed is:

1. A method of increasing plasma oxytocin concentration in a subject, wherein the method comprises administering an effective amount of a composition to the subject and thereby increasing plasma oxytocin concentration in the subject, wherein the composition comprises a lysate, wherein the lysate comprises killed *Lactobacillus reuteri* bacteria, and wherein the *L. reuteri* bacteria comprises *L. reuteri* isolate 2546.

2. The method of claim 1, wherein the subject is a mammal.

3. The method of claim 1, wherein the *L. reuteri* bacteria is isolated from dog saliva.

4. The method of claim 1, wherein the *L. reuteri* bacteria comprises *L. reuteri* ATCC 6475.

5. The method of claim 1, wherein the composition is administered orally.

6. The method of claim 1, herein the composition reduces the subject's subcutaneous fat.

7. The method of claim 1, wherein the composition reduces the subject's blood neutrophils.

8. The method of claim 1, wherein the composition promotes lean muscle formation.

9. The method of claim 1, wherein the composition promotes hair growth.

10. The method of claim 1, wherein the composition promotes wound healing.

11. The method of claim 1, wherein the *L. reuteri* bacteria are lysed by sonication to produce the lysate.

12. The method of claim 11, wherein the lysate is passed through a 0.2 μm filter to remove whole bacteria, thereby producing a soluble supernatant comprising the lysed *L. reuteri* bacteria.

13. The method of claim 12, wherein the lysate comprises the soluble supernatant.

14. A method of increasing plasma oxytocin concentration in a subject, wherein the method comprises administering an effective amount of a composition to the subject and thereby increasing plasma oxytocin concentration in the subject, wherein the composition comprises a lysate, wherein the lysate comprises killed *Lactobacillus reuteri* bacteria, and wherein the *L. reuteri* bacteria is isolated from dog saliva.

15. A method of increasing plasma oxytocin concentration in a human subject, wherein the method comprises administering an effective amount of a composition to the subject and thereby increasing plasma oxytocin concentration in the subject, wherein the composition comprises a lysate, wherein the lysate comprises killed *Lactobacillus reuteri* bacteria, and wherein the *L. reuteri* bacteria comprises *L. reuteri* isolate 2546.

* * * * *